United States Patent [19]

Brois et al.

[11] Patent Number: 4,851,524

[45] Date of Patent: Jul. 25, 1989

[54] AMINE-TREATED THIO-BIS-(ALKYL LACTONE ACID) AND THIO-BIS-(HYDROCARBYL DIACID) MATERIALS, ADDITIVES FOR LUBRICATING COMPOSITIONS

[75] Inventors: Stanley J. Brois, Westfield; Antonio Gutierrez, Mercerville, both of N.J.

[73] Assignee: Exxon Research and Engineering Company, Florham Park, N.J.

[21] Appl. No.: 802,594

[22] Filed: Nov. 27, 1985

Related U.S. Application Data

[60] Division of Ser. No. 415,980, Sep. 8, 1982, abandoned, which is a division of Ser. No. 243,781, Mar. 6, 1981, abandoned, which is a continuation of Ser. No. 67,546, Aug. 17, 1979, abandoned, which is a continuation-in-part of Ser. No. 817,217, Jul. 20, 1977, Pat. No. 4,174,322, and a continuation-in-part of Ser. No. 806,326, Jun. 13, 1977, Pat. No. 4,176,514, which is a division of Ser. No. 726,206, Sep. 24, 1976, Pat. No. 4,062,786.

[51] Int. Cl.$^4$ ................... C07D 257/02; C07D 259/00
[52] U.S. Cl. ..................................... 540/474; 540/470; 540/467; 540/465
[58] Field of Search ................................ 540/470, 474

[56] References Cited

U.S. PATENT DOCUMENTS

| | | | |
|---|---|---|---|
| 4,062,786 | 12/1977 | Brois et al. | 252/51.5 |
| 4,123,373 | 10/1978 | Brois et al. | 252/48.6 |
| 4,167,514 | 9/1979 | Brois et al. | 260/343.5 |
| 4,174,322 | 11/1979 | Brois et al. | 548/237 |
| 4,174,428 | 11/1979 | Tabashi et al. | 540/460 |
| 4,221,720 | 9/1980 | Brois et al. | 260/343.6 |
| 4,239,636 | 12/1980 | Brois et al. | 252/48.6 |
| 4,292,184 | 9/1981 | Brois et al. | 252/46.3 |
| 4,302,395 | 11/1981 | Brois et al. | 260/343.6 |
| 4,391,981 | 7/1983 | Brois et al. | 549/252 |
| 4,417,062 | 11/1983 | Brois et al. | 549/320 |
| 4,568,756 | 2/1986 | Brois et al. | 549/267 |
| 4,637,886 | 1/1987 | Brois et al. | 252/51.5 |

FOREIGN PATENT DOCUMENTS 0184068 9/1985 Japan ................... 540/460

*Primary Examiner*—David B. Springer
*Attorney, Agent, or Firm*—F. T. Johmann; M. B. Kapustij

[57] ABSTRACT

Thio-bis-(hydrocarbyl substituted diacid materials), such as thio-bis-(polyalkyl lactone acid) and/or their precursors, the adducts of sulfur chloride and unsaturated diacid materials, e.g., 4,8-bis-polyalkyl-4, 8-dichloro-6-thiaundecane-1,2,10,11-tetracarboxylic acid bis-anhydride and especially their dehydrochlorinated analogs, when treated with an amine preferably polyalkylene polyamines such as tetraethylene pentamine, directly or in the presence of a metal template reagent, yield aminated thio-bis-(alkyl lactone acid) and thio-bis-(hydrocarbyl diacid) materials or their metal complexes which can be characterized in part, as macrocyclic and/or macrocyclic-like amide and/or imide structures, are useful as stable additives in lubricating compositions, e.g., as varnish inhibiting dispersants and/or inhibitors for lubricating oils and fuels.

3 Claims, No Drawings

AMINE-TREATED THIO-BIS-(ALKYL LACTONE ACID) AND THIO-BIS-(HYDROCARBYL DIACID) MATERIALS, ADDITIVES FOR LUBRICATING COMPOSITIONS

CROSS-REFERENCE TO RELATED APPLICATIONS

This application is a divisional of U.S. Ser. No. 415,980, filed 9/8/82 abandoned which is a division of Ser. No. 243,781, filed 3/16/81, abandoned, which is a continuation of Ser. No. 67,546 filed 8/17/79, abandoned which is a continuation-in-part of U.S. Pat. application Ser. No. 817,217, filed July 20, 1977, U.S. 4,174,322 and U.S. Pat. application Ser. No. 806,326 filed June 13, 1977, U.S. 4,167,514, which in turn is a division of Ser. No. 726,206 filed Sept. 24, 1976, U.S. 4,062,786.

BACKGROUND OF THE INVENTION AND PRIOR ART

The present invention concerns amine-treated thio-bis-(alkyl lactone acid) and thio-bis-(hydrocarbyl diacid) materials, their metal complexes, their method of preparation and their utility, preferably, in hydrocarbon fuel and lubricating systems, as stable sludge dispersants, varnish inhibitors, lubricity agents, and antioxidants.

During the past decade, ashless sludge dispersants have become increasingly important, primarily in improving the performance of lubricants and gasoline, in keeping the engine clean of deposits, and permitting extended crankcase oil drain periods. One category of ashless dispersants concerns acylated nitrogen-containing compounds which can be prepared via the acylation of polyalkylene polyamines, e.g., tetraethylenepentamine, with such acylating reagents as: (i) polyalkenyl succinic anhydrides as taught in U.S. Pat. Nos. 3,172,892, 3,219,666, and 3,272,746; (ii) chlorinated alkenyl succinic acid derivatives as taught in U.S. Pat. No. 3,996,240; (iii) halolactone acid derivatives as featured in U.S. Pat. No. 3,620,977; and (iv) simple lactone acids as taught in U.S. Pat. Nos. 3,200,075, 3,261,782, 3,487,452, 3,734,865, 3,936,472, 4,132,531 and British Pat. No. 1,420,962. However, dispersants of this category are susceptible to oxidative degradation especially under high severity conditions engendered by elevated oil temperatures and extended drain intervals. Such dispersants tend to break down and promote sludge and deposit formation. Besides instability problems, the inherent limitations in sludge binding properties of this class of dispersants tend to diminish their potency as the severity of operating conditions increases.

In the prior art, several attempts were made to stabilize dispersants of category (i) by incorporating, for example, sulfur into the molecule as taught in U.S. Pat. Nos. 3,309,316, 3,390,086 and 3,470,098. Because of the nature of the synthetic pathways selected in these prior studies, however, the sulfur that was incorparated into such dispersants was unstably bonded and as a consequence, tended to promote sludge and varnish formation.

The present invention by virtue of new synthetic approaches, overcomes the shortcomings of the prior art by designing novel, aminated thio-bis-(polyalkyl lactone acid) and thio-bis-(hydrocarbyl diacid) materials with enhanced stability and potency. The stabilization of these novel dispersant systems may be related to the introduction of stable mono- and disulfide functionality which imparts to these systems enhanced antioxidant properties. The enhanced potency may be ascribable to the macrocyclic and/or macrocyclic-like configurations assumed by the polar sullfur and nitrogen (heteroatom) functionality in some of the dispersant molecules. Such circular-like arrangements of ligands endow these novel systems with remarkable binding and/or chelation properties and in some instances, inclusion properties, making these dispersant systems uniquely effective even under high severity conditions.

It is a further object of this invention to provide novel and improved dispersant systems based on host guest chemistry wherein the polar head of the host molecule (dispersant) assumes or is capable of assuming a macrocyclic-like configuration so that the resulting circular-like array of heteroatoms (e.g. sulfur, oxygen and nitrogen), on the polar head effectively binds guest ions and molecules, including metals and sludge components, within the cyclic-like structure, or between host molecules to form a sandwich-like structure with guest molecules in the middle.

SUMMARY OF THE INVENTION

It has now been discovered that hydrocarbon-substituted thioethers, which feature, in part, vicinal lactone and amide and/or imide functions, can be arranged in macrocyclic or macrocyclic-like configuration using novel synthetic methods whereby a highly stable additive of enhanced dispersancy, enhanced viscosity properties, and antioxidant properties can be realized. One important member of this novel class of macrocyclic and macrocyclic-like additives can be represented as amide, and/or imide derivatives of 6,6'-thio-bis(4,5,6-trisubstituted-3,5-carbolactonehexanoic acid) as illustrated in Formula Ia:

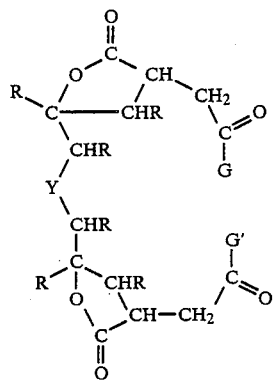

wherein R is selected from the group consisting of hydrogen, hydrocarbyl and substituted hydrocarbyl containing from 1 to 10,000, preferably 12 to 200, carbons with the restriction that at least one R has at least about 4 carbons; Y, the bridging or coupling element, is selected from the group consisting of S (thio), S-S (dithio), S=O (sulfinyl), $SO_2$ (sulfonyl), Se (seleno), S—$(CH_2)_z$S— where z is a number of from 2 to 10; and, G and G' each represent the same or a different nitrogen-containing functional group,

with A and A' being represented by hydrogen and/or a $C_1$ to $C_{100}$ hydrocarbyl substituent and particularly a polyalkylene polyamine substituent. Useful amine reagents which engender amide and/or imide groups include ammonia, monoamines, polyamines, polyoxyalkylene amines and macrocyclic amines. The amines can be primary or secondary and are preferably polyamines such as polyalkylene amines, their hydroxyl-containing derivatives, polyoxyalkylene polyamines and macrocyclic polyamines.

Typically, G represents a nitrogen-containing function; G' is usually the same as G; however, G' may also be selected from an assortment of oxy-functional groups including hydroxyl, alkoxy, aryloxy, and $-OH \cdot HNA_2$. Such combinations of oxy- and nitrogen-containing functionality ofttimes endow these additives with multifunctional properties.

In some cases, depending upon stoichiometry, the nature of the reactants, and the mode of synthesis, G+G' together can represent a linking group such as imino

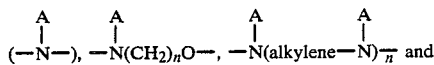

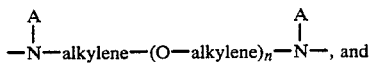

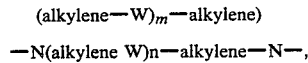

where n=1 to 20, m=0–10 and the alkylene groups may be straight or branched chains and will contain from 2 to 8 carbon atoms and usually 2 to 4 carbons; and W represents a hetero function such as O, S, or N-A. Such linking groups create equimolar [one mole of thio-bis(acylating agent) to one mole of of amine (1:1)] macrocyclic ring structures of varying sizes and composition depending upon the nature of the thio-bis(acylating reagent) and the amine reagent. Sometimes, G and G' may bond to another molecule of thio-bis(acylating agent) e.g., thio-bis(lactone acid) in which instance, two acylating reactants essentially combine with two moles of amine (2:2) to yield structurally larger macrocyclic species of doubled molecular weight. Furthermore, equimolar condensation products of thio-bis-(acylating agent) and amine are capable of forming, under suitable reaction conditions, even larger macrocyclic structures, e.g., (3:3), (4:4), etc. Usually, mixtures of linear and cyclic amide and/or imide oligomers are formed, and the ratio of cyclic to linear oligomers is a sensitive function of reaction conditions, and the nature of the reactants and the presence of a template reagent (e.g. metal ion); however, with a judicious choice of experimental conditions, one can achieve a suitable mix of cyclic and linear amide and/or imide products (or metal comlexes) for specific end uses.

Other members of this novel calss of macrocyclic and macrocyclic-like additives can be represented as amide, and/or imide derivatives of (i) thio-bis(alkene diacid) as depicted in Formulas Ib and Ic where J+L together represents a pi ($\pi$) bond; (ii) thio-bis(alkane diacid) as featured in Ib and Ic where J and L are both hydrogen; (iii) thio-bis-(hydroxy-or chloro- alkane diacid) as illustrated by Ib and Ic wherein J corresponds to OH or Cl and L is hydrogen (H).

In Formula Ic, A+A' together can (like G+G') represent a linking group such as alkylene,

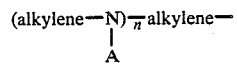

and -alkylene-(O-alkylene)$_n$. R,Y,G,G',A,A' and n were defined earlier.

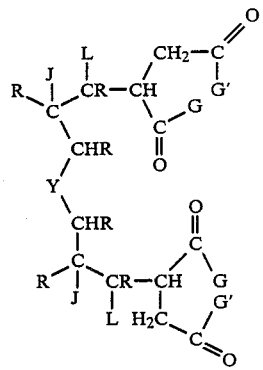

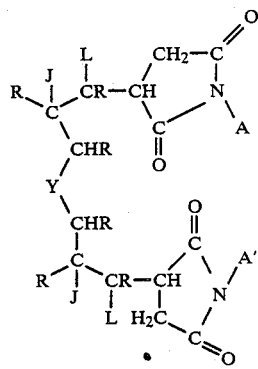

It is noteworthy that the presence of a metal ion such as copper, iron, nickel, cobalt, or zinc, in catalytic or stoichimetric amounts during amidation or sulfur bridging, tends to increase the yield of macrocycles over the products of competing linear polymerizations, a phenomenon known as the template effect. In such cases, the formation of macrocycles are presumably mediated via the template action of these metals. Obviously, such metal ion assisted cyclizations provide a variety of useful cyclic ligands and their complexes for additive applications. In such cases, the metal ion species, depending upon its effective size and the nature of the polyamine, forms a template about which the polyamine and thio-bis-(acylating agent) can react to form 1:1, 2:2, and 3:3 and larger macrocycles in substantial yields. The ability to control the mode of reaction with certain ions provides a convenient and novel approach to tailoring the composition of aminated products to meet specific viscosity and performance requirements.

Preferred herein are aminated mono- and dithio-bis-(alkyl lactone acid) materials of number average molecular weight (Mn) ranging from about 400 to about 140,000 prepared by the reaction of a thio-bis-(alkyl lactone carboxylic acid) or a dehydrochlorinated $S_xCl_2$-olefin diacid adduct wherein x is 1 or 2, with a polyamine such as tetraethylenepentamine,at about 20°–240° C. or preferably 50°–180° C. with or without a promoter, until the amidation and/or imidation processes are complete by IR analysis.

These novel compounds described above are effective as dispersants, inhibitors, antiwear and/or lubricity additives which are particularly useful in lubricating oil compositions and are also useful as additives in distillate fuel compositions and gasoline as well as synthetic lubricating oils and automatic transmission fluids. Thus, it is within the scope of this invention to dissolve a small but at least an effective amount of said compounds of the invention in a major proportion of a hydrocarbon material to provide useful hydrocarbon compositions. These preferred hydrocarbnon soluble compounds have at least 4 carbons in the substantially saturated aliphatic hydrocarbyl groups with preferrably one carboxylic acid group of each terminal dicarboxylic acid function converted into a lactone ring and the other carboxylic acid group converted into an amide and/or imide as a result of the reaction of at least an equivalent amount of said thio-bis-(hydrocarbyl substituted diacid material), including both the diacid and anhydride, and a molar amount of an amine or polyamine having about 2 to 20 nitrogen functions and containing a total of 2 to 100 carbons.

The novel amine-treated thio-bis-(alkyl lactone acid) or thio-bis(hydrocarbyl diacid) materials of the present invention can be prepared by heating together thio-bis-(alkyl lactone acids or esters), or dehydrochlorinated $YCl_2$-polyalkene diacid or anhydride adducts (Y having the meaning previously given) with 0.5–2 moles of amine via the (i) conventional method or by a (ii) template procedure. The latter option involves reactions in the presence of a metal ion which presumably induces the reaction of condensing functional groups within its coordination sphere (template effect) so as to generate macrocyclic complexes in the equimolar reaction of a thio-bis-(acylating agent) and a polyamine reactant. Macrocyclic ring size is governed by such factors as the nature of the metal ion and the polyamine chain length. The conventional method involves the amidation of thio-bis-acylating agents with 0.5–2 moldes of amine reagent, preferably a polyamine, directly or mediated via promoters such as carbodiiments ($RN=C=NR$).

It has been further discovered that other useful thio-bis-(acylating agents) comprising (i) thio-bis-(alkenyl diacid/anhydride/ester) prepared via the dehydrochlorination of adducts of olefin diacids with sulfur halides and (ii) dithio-bis-(alkyl diacid/anhydride/ester) prepared by means of sulfur bridging with thiols under oxidative conditions, when subsequently reacted with an amine afford novel additives (and complexes) possessing lubricating oil dispersancy, anti-oxidation and/or friction modification properties.

DETAILED DESCRIPTION OF THE INVENTION

In the following description of this invention, the reactants, i.e., thio-bis-acylating agents, their formation via the bridging (or coupling) of alkene diacid materials with a sulfure halide or a sulfur halide equivalent such as a sulfenate ester-HCl combination reagent or a thiol-halogen combination reagent; the condensation reactions of the bridged acylating agents with amine directly or in the presence of metal templating reagents, and the utilization of the novel amide/imide products and their metal complexes are set forth below in detail.

THIO-BIS-(ACYLATING REAGENTS)

The preparation of the mono- or dithio-bis-(lactone alkanoic acid or ester), mono- or dithio-bis-(alkene dioic acid or anhydride or ester) or dithio-bis-(alkane dioic acid or anhydride or ester) acylating agents involve the sulfur halide coupling or bis-sulfenyl halide-induced coupling or the oxidative coupling of $H_2S$ or thioacid adducts of an olefin diacid. The olefin diacid is readily obtained via the reaction of an olefin or a chlorinated olefin with an unsaturated $C_4$ to $C_{10}$ dicarboxylic acid, anhydride or ester thereof, such as fumaric acid, itaconic acid, maleic acid, maleic anhydride, dimethyl fumarate, etc. The dicarboxylic acid material formed via the Ene reaction of an olefin with maleic anhydride can be illustrated as an alkenyl-substituted anhydride which may contain a single alkenyl radical or a mixture of alkenyl radicals variously bonded to the cyclic succinic anhydride group, and is understood to comprise such structures as:

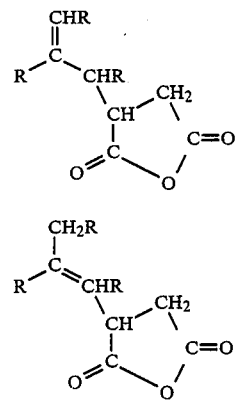

with the $\gamma,\delta$-unsaturated isomers predominating and wherein R may be hydrogen or hydrocarbyl or substituted hydrocarbyl containing from 1 to about 10,000 and more carbons with the restriction that at least one R has at least 1 carbon, preferably from about 16 to about 400 carbons and optimally from about 60 to about 100 carbons. The anhydrides can be obtained by well-known methods, such as the reaction between an olefin and maleic anhydride or halosuccinic anhydride or succinic ester (U.S. Pat. No. 2,568,876). In branched olefins, particularly branched polyolefins, R may be hydrogen, methyl or a long chain hydrocarbyl group. However, the exact structure may not always be ascertained and the various R groups cannot always be precisely defined in the Ene products from polyolefins and maleic anhydride.

Suitable olefins include butene, isobutene, pentene, decene, dodecene, tetradecene, hexadecene, octadecene, eicosene, and polymers of propylene, butene, isobutene, pentene, decene and the like, and halogen-containing olefins. The olefins may also contain cycloalky and aromatic groups. The most preferred alkenyl succinic anhydrides used in this invention are those in which the alkenyl group contains a total of from 4 to 400 carbon atoms; and, at least 16 to 400 and more preferably 60 to 100 for mineral oil systems.

Many of these hydrocarbyl substituted dicarboxylic acid materials and their preparation are well known in the art as well as being commercially available, e.g.

2-octadecenyl succinic anhydride and polyisobutenyl succinic anhydride.

With 2-chloromaleic anhydride and related acylating agents, alkenylmaleic anhydride reactants are formed. Bridging of these products with YCl$_2$ also afford useful precursors to aminated thio-bis-(lactone acid) products.

Preferred olefin polymers for reaction with unsaturated dicarboxylic acids are polymers comprising a major molar amount of C$_2$ to C$_5$ monoolefin, e.g., ethylene, propylene, butylene, isobutylene and pentene. The polymers can be homopolymers such as polyisobutylene, as well as copolymers of two or more of such olefins such as complymers of: ethylene and propylene; butylene and isobutylene; propylene and isobutylene; etc. Other copolymers include those in which a minor molar amount of the copolymers monomers, e.g., 1 to 20 mole % is a C$_4$ to C$_{18}$ non-conjugated diolefin, e.g., a copolymer of isobutylene and butadiene; or a copolymer of ethylene, propylene and 1,4-hexadiene; etc.

The olefin polymers will usually have number average molecular weights (M$_n$) within the range of 500 and about 140,000; more usually between about 700 and about 10,000. Particularly useful olefin polymers have (M$_n$) within the range of about 700 and about 5,000 with approximately one terminal double bond per polymer chain. An especially valuable starting material for a highly potent dispersant additive are polyalkenes e.g. polypropylene and polyisobutylene, having about 90 carbons. The dicarboxylic acid materials (Diels-Alder adducts) formed via the reaction of a chlorinated olefin with maleic anhydride also useful in the present invention, can be illustrated in part, by the following structures:

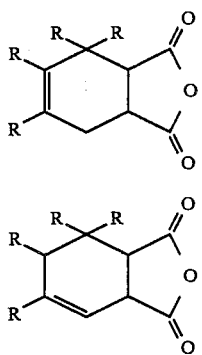

where R is as previously defined. Useful chlorinated olefins include chlorinated di-isobutylene, tri-isobutylene, polyisobutylene, tetrapropylene, polyisopropylene, and alkenes which upon halogenation characteristically afford allylic halide structures.

Hemi-ester or deacid reactants can be constructed readily form the anhydride products obtained via the Ene process by the scission of the anhydride ring with a mole of alcohol or water. Normally, the ring opening process is effected by interacting equimolar amounts of anhydride and alcohol or water at temperatures of 25° C. to about 120° C. without diluent or with a suitable solvent such as tetrahydrofuran, p-dioxane, 1,2-dimethoxy-ethane, etc. In conversions to the diacid, excess water may be added to accelerate the ring scission process. With alcohols, excess alcohol may lead to some di-ester formation, and accordingly equimolar reaction stoichiometry, is preferable. In the absence of strong acid catalysts, however, excess alcohol can be used to effect hemi-ester formation. Suitable alcohol reactants include methanol, ethanol, isopropanol, butanol or other simple monohydric alcohols which can be removed readily by evaporation or distillation.

BRIDGING REACTIONS

The bridging or coupling of the precursor acylating agents can be achieved via a choice of synthetic options including (i) addition of sulfur halides or bis-sulfenyl halides or alkyl sulfenate/HCl reagent to unsaturated diacids, hemi-esters, diesters or anhydrides, (ii) the oxidative coupling of unsaturated acids previously thiylated with H$_2$S or R$_1$C(=O)SH, where R$_1$ represents a C$_1$-C$_5$ alkyl group, or (iii) reaction of α,ω-alkanedithiols, H$_2$S, or a suitable thiylating agent, with epoxidized or halogenated alkene dioic acid or anhydride materials. Synthetic approaches (i) and (ii) are described in detail herein.

In contrast to the facile and effective modes of sulfur bridging outlined above, other possible synthetic options including the sulfurization of olefin diacid materials with elemental sulfur, and the Ene reaction of alkenyl sulfides do not provide discernable amounts of stable, sulfurbridged olefin diacid materials.

The prior art clearly teaches that the sulfurization of alkenes with elemental sulfur gives complex mixtures of unsaturated, unstable polysulfides and polymeric sulfides up to about 140° C., and at higher temperatures, ca. 170° C., the polysulfidic products owing to limited thermal stability, undergo extensive decomposition of yield hydrogen sulfide, thiols, 1,2-dithiole-3-thiones and/or thiophenes as the major products. Moreover, sulfurization of alkenylsuccinic anhydrides with elemental sulfur also generates thioanhydride products which tend to eleminate hydrogen sulfide when treated with protic reagents such as amines.

Finally, the Ene reaction of disulfides with maleic anhydrides does not engender the desired Ene product, but affords only low yields of 2-alkylthiasuccinic acid derivatives in a neither clean nor synthetically attractive reaction.

BRIDGING WITH SULFUR HALIDES

The preferred pathway to bridge acylating agents involves the reaction of sulfur halides, bis-sulfenyl halides or a sulfenate ester/HCl reagent with unsaturated diacids, hemi-esters, di-esters or anhydrides in the temperature range of −60° C. to about 100° C., optimally from about 10° C. to 50° C. If desired, solvents comprising hydrocarbons such as pentane, hexane, heptane, cyclohexane, mineral oil; halocarbons such as methylene chloride, chloroform, carbon tetrachloride, aromatics such as toluene, chlorobenzenes, xylene; ethers, such as diethyl ether and tetrahydrofuran (THF); and, acids such as acetic, propionic and trifluoroacetic acid, can be used in favorably controlling viscosity and reaction temperature. The mode of addition of reagents is dictated by convenience. Usually, the sulfur halide is added dropwise to an unsaturated diacid, ester, or acid anhydride, preferably diluted in an inert diluent. With reactive diluents, namely those containing unsaturates including aromatics, and olefins such as polyisobutylene, sufficient sulfur halide must be added to effect complete bridging of the olefin diacid reactants.

When the addition of one mole of sulfenyl halide to 2 moles of alkene dioic acid anhydride is conducted at low temperatures, e.g. −60° C. to about 20° C., a discrete YCl₂-anhydride adduct II forms as depicted in the equation with R and Y as defined earlier:

cide anhydride) (III) wherein the double bond position shown may vary depending upon reaction conditions.

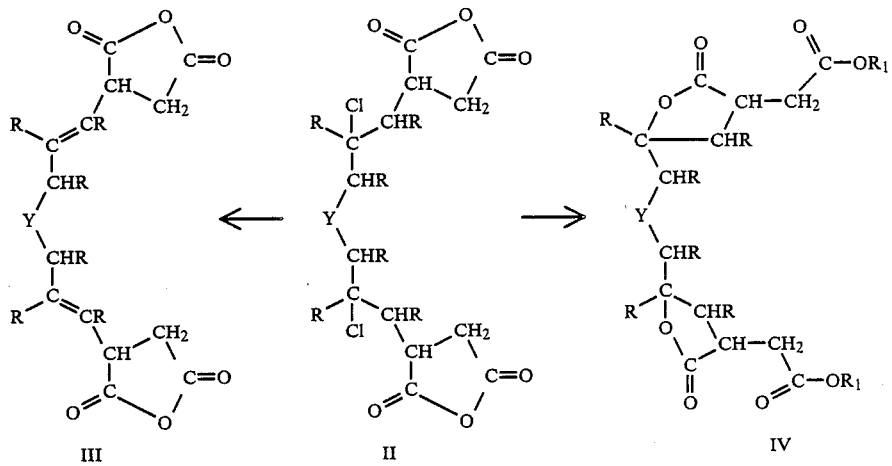

Adduct II is a key intermediate, serving as a useful thio-bis-acylating agent per se, but more importantly, as a precursor to the other thio-bis-acylating agents, III and IV. As illustrated below, solvolysis of II, in the presence of a strong acid catalyst, with $R_1OH$ ($R_1$=H-,Me,Et) affords thio-bis-(lactone acid/ester) (IV). Dehydrochlorination II with base or heating in refluxing dioxane on the other hand, affords thio-bis-(alkene dia- Increasing bridging temperature above about 50° C., and branching in the hydrocarbyl portion of the alkene dioic anhydride tend to accelerate the elimination of HCl from the YCL₂-alkene dioic anhydride adduct. Since unsaturated bridged products can be further sulfenylated with YCL₂ reagent (re-addition), it becomes necessary in some cases, to modify the theoretical 2:1 stoichiometry to effect complete bridging. Accordingly, at higher temperatures, i.e., from 50°–100° C., ratios in the range of 1.5:1 to 1:1 may be required to realize higher conversions to bridged structures due to re-addition reactions, and the partial thermal decomposition of the sulfur halide reactant at elevated temperatures. While more sulfur halide reagent becomes necessary to achieve coupling, the additional sulfur incorporated into the dispersant precursor (and occasionally the diluent) tends to endow the resulting thio-ether products with enhanced oxidative stability.

When maximal bridging with sulfur halide is desirable, high purity chlorosulfenylating reagent (distilled SCL₂), lower sulfenylating temperatures, and select thio-(bis-acylating reagents) comprising hemi-ester, and/or diacid reactants, dissolved in a minimal amount of olefinic diluent, provide useful synthetic options in realizing more efficient coupling processes. The concept of bridging hemi-ester and/or diacid reactants (which tend to be more amenable to lactonization) is depicted in the equation:

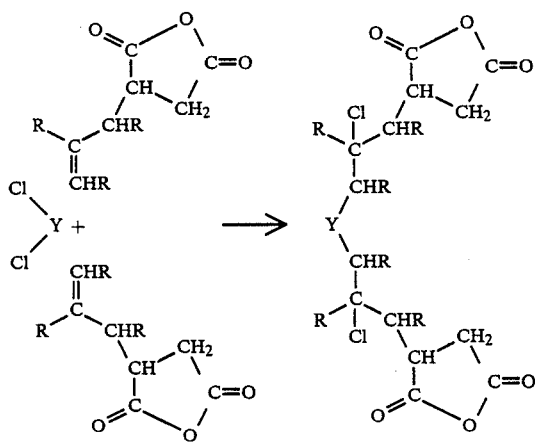

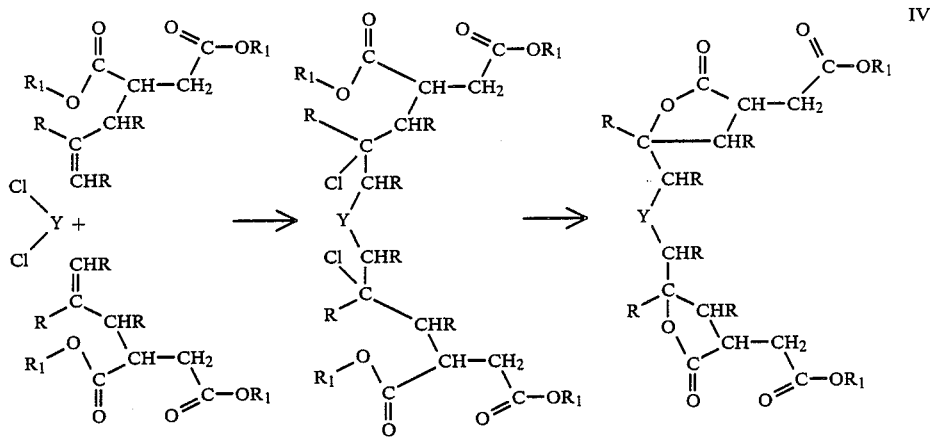

IV wherein R and $R_1$ are the same as earlier defined. The $YCl_2$ addition to the alkenyl hemi-ester, diester or di-acid previously freed of olefinic diluents by silica gel extraction, affords discrete adducts which can be lactonized via a temperature-sensitive, internal displacement of chloride by a vicinal carboxylic acid or ester group. Chloride displacement with resultant lactonization circumvents the elimination of HCl which would otherwise lead to thio-bis-(alkene dioic acid or ester) products (III).

It should be noted, however, that treatment of the latter sulfur-bridged unsaturated acylating agent with simple alcohols to effect esterification usually generates mixtures of thio-bis (lactone acid ester) and thio-bis (alkene diacid ester); however, selective conversions to thio-bis (lactone acid ester) can be achieved prior to or during esterification, by using acid catalysts comprising soluble acids such as sulfuric acid, alkyl sulfonic acids (where alkyl corresponds to a $C_1$ to $C_{60}$ aliphatic radical selected from the group consisting of open chain alkyl, isoalkyl, and cycloalkyl); alkyl aromatic sulfonic acids (where alkyl is defined as above and the aromatic groups can be derived from benzene, toluene, xylene, mesitylene and naphthalene); suitable alkyl aromatic sulfonic acids include i-dodecyl benzene sulfonic acid (Petrostep A-60, Stephan Chemical Co.), i-dodecyl benzene sulfonic acid (Ultrawet 99LS from Arco Chemical Co.) and i-tetracosyl benzene sulfonic acid (SA 119, Esso Chimie, France); Lewis acids such as $BF_3$, $BF_3$ etherate, $AlCl_3$; and resin acids including resin sulfonic acids such as Amberlyst 15 (Rohm and Haas Company, Philadelphia, Pa.) and perfluorinated resin sulfinic acids such as NAFION-H (E.I. DuPont de Nemours and Co., Inc. Wilmington, DE are suppliers of NAFION perfluorosulfonic acid products); and finally, acidic solid phase catalysts, including silica gel (activated, Grade H, mesh size 100–200 from Davison Chemical, Baltimore, MD), alumina (acid $Al_2O_3$) silica alumina, zeolite, and certain clays. Silica gel-induced lactonizations are highly useful, since it is believed that the silica gel plays a dual role as a lactonization catalyst and as a template for generating in part, macrocyclic-like products.

As indicated above, sulfur halides including $SCl_2$, $S_2Cl_2$ and alkyl sulfenate ester/HCl reagent are suitable bridging agents. Bis-sulfenyl halides derived from alkane, heteroalkane, aromatic, heteroaromatic, and heterocyclic radicals such as

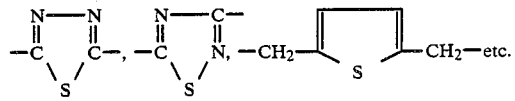

are also useful coupling agents.

Oxidation of the mono-thio ether products and reactants provides access to useful sulfoxide and sulfone derivatives. A variety of inorganic and organic oxidizing agents can be used to effect these conversions including hydrogen peroxide, peracids, hydroperoxides, e.g. t-butyl hydroperoxide, chlorine, positive halogen reagents, nitric acid, oxides of nitrogen, oxygen, ozone and metal oxides. The preferred oxidant is hydrogen peroxide usually in acetic acid and as necessary, in an aromatic an aromatic solvent, e.g. toluene. Oxidation with equimolar quantities of reactants at about 0° to 60° C. provides the sulfoxide in excellent yield. A 2:1 molar ratio of peroxide to said thio ether product produces the sulfone derivative. The peroxide oxidation of sulfides to sulfones is perferably carried out in the presence of catalytic amounts of conventional oxidation catalysts such as tungsten, molybdenum, e.g. molybdenyl acetylacetonate, or vanadium salts.

MECHANISM OF BRIDGING WITH SULFUR HALIDES

The key feature of the addition reactions of sulfur halides, preferably sulfur chlorides or bis-sulfenyl chlorides is their intrinsic ability to couple or bridge a wide variety of unsaturated acid materials in a well-defined manner; this key feature clearly distinquishes the behavior of sulflur halides from other sulfur donors such as elemental sulfur which produces only complex, unstable and ill-defined mixtures of sulfurized products. As indicated above, the sulfur halides add selectively to the point of saturation, with a 1:1 sulfenyl chloride adduct being formed initially, followed by the addition of the latter to another unsaturated acid to form a dichlorosulfide adduct as shown in the above equation.

The composition of the adduct hinges on (a) the position of the double bond in said olefin diacid material, and (b) the mode of sulfur halide addition, i.e., an electrophilic addition, as determined by steric and electronic factors. Judging from the structure of the unsaturated acid reactants from spectral evidence, it is believed that the thio-bis-(lactone acid or ester) reactants are best illustrated by the structures featuring 5-membered lactone rings as proposed in the above equations. The formation of some six-membered lactones (and even larger ring lactones), however, has been ovserved by IR spectral analysis, particularly during the alcohol or water-induced lactonization of $S_xCl_2$-olefin diacid adducts. Accordingly, 6-ring (or larger ring) lactones and other positional isomers based on the position of sulfur in the bridged structures can also be present in the products of this invention.

BRIDGING WITH THIOLS

In another embodiment of the present invention, thio-bis-(acylating agents) can be constructed via the (i) peroxide or (ii) acid-induced addition of $H_2S$ and/or thioacids to olefin diacid materials to give thiolactone acids and/or thiol-substituted diacids which are then amenable to bridging via (a) oxidative coupling with $Cl_2$, $SO_2Cl_2$, $H_2O_2$, or peracids or (b) displacement reactions with $\alpha,\omega$-alkylene dihalides, e.g. ethylene dichloride.

Alkene dioic acid materials (diacid anhydride or ester) can be readily reacted with $H_2S$ and thioacids under both heterolytic (acid-induced) and homolytic (radical-induced) conditions. Typically, the acid catalyzed reaction affords a product wherein sulfur becomes bonded to the most substituted carbon atom, as shown by the equation:

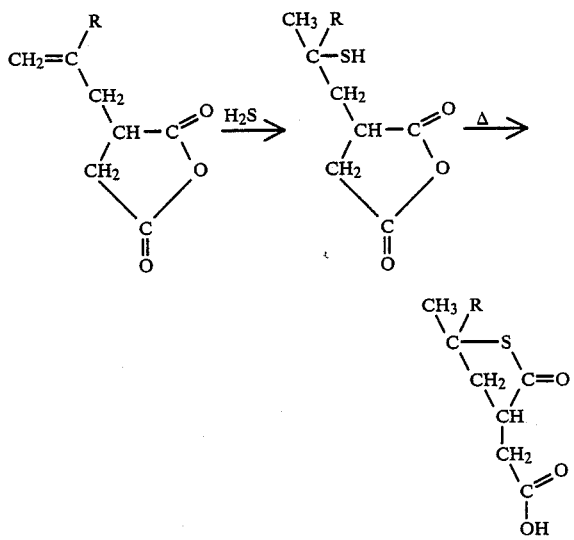

wherein R and $R_1$ are as previously defined.

Hydrogen sulfide (usually added in about a two to ten fold excess) reacts with olefin diacid materials (here the anhydride) according to the above equation at comparatively low temperatures, e.g. from about $-70°$ C. to about $25°$ C. in the presence of ca. 0.1 to about 10 wt. % of such acid catalysts as HCl, $BF_3$, or a chloride salt of Al, Zn, B, P, Sn, Ti and Sn. The aforesaid hydrogen sulfide addition can also be catalyzed with etherates, alcoholates or hydrates of $BF_3$. The $H_2S$ addition products can be isolated as the corresponding thiolactone derivatives owing to the facile lactonization of the mercapto derivative as shown in the above equation. Both the mercapto and thiolactone derivatives can be readily bridged via oxidative coupling or displacement reactions in protic solvents such as water and alcohols.

A synthesis of isomeric thiol-substituted diacid material can also be effected via the homolytic reaction of olefin diacid material with thiols and thioacids. Reactive thiols such as thioacetic acid add readily to the least substituted olefinic carbon atom in alkene dioic acid reagents in the presence of small amounts, e.g. about 0.05 to 1 wt. % of peroxides such as benzoyl peroxide, di-tert-butyl peroxide, to give a thioacyl substituted alkane dioic acid material, which is thereafter oxidized with sulfuryl chloride in methanol to the corresponding symmetrical disulfide product (V) as shown in the equation:

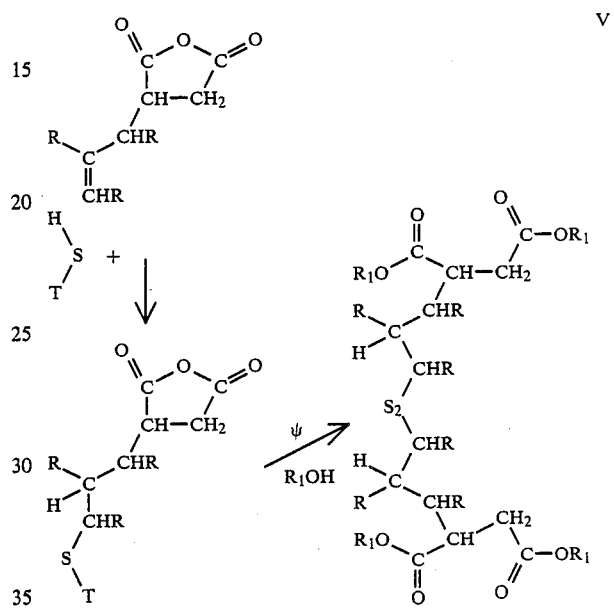

wherein T is an acyl group, e.g. acetyl; $\psi$ refers to such oxidants as $Cl_2$, $SO_2Cl_2$, and $H_2O_2$; and R and $R_1$ are the same as previously described.

As seen above, thiolactones and thiol-substituted diacid materials can be easily bridged via oxidative solvolysis using a combination of an oxidant such as air, $H_2O_2$, peroxide, chlorine or $SO_2Cl_2$, and a protic solvent such as water, or alcohol. An alternate preparative option to bridging involves a nucleophlic displacement of the thiol-substituted diacid reagent with $\alpha,\omega$-alkane dihalides including $Cl(CH_2)_nCl$, $Cl(CH_2CH_2S)_nCH_2CH_2Cl$ and $Cl(CH_2CH_2O)_nCH_2CH_2Cl$, wherein n is a number from 1 to 10, and bis-chloromethylated aromatics, heteroaromatics and heterocycles.

AMINE REACTANTS

The amine reactants useful in designing thio-bis-acylated nitrogen products of the present invention can be characterized by the general formula

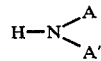

wherein A and A' represent hydrogen and/or an organic radical such as a polyalkylene polyamine group. In some cases, A+A' will represent a cyclic or macrocyclic amine or polyamine. Amines which find use include ammonia, monoamines, polyamines, polyoxyalkylene amines, and macrocyclic polyamines.

1. Monoamines

The monoamines useful in designing additives via the novel process of aminating thio-bis-acylating agents can be primary amines, i.e., the amino nitrogen is bonded to two hydrogens, or secondary amines, i.e., the amino nitrogen is bonded to only one hydrogen. Moreover, such monoamines can feature aliphatic, aromatic and-/or heterocyclic substituents. Aliphatic monoamines containing 1-30 carbons are especially preferred and include n-alkyl, isoalkyl, alicyclic, alkenyl, alkynyl and hydroxyalkyl substituents.

Examples of n-alkyl substituted monoamines include ethylamine, diethylamine, n-butylamine, di-n-butylamine, n-octyl amine, caprylylamine, caprylamine, di-n-octylamine, n-dodecylamine (tallowamine) myristylamine, pentadecylamine, margarylamine, n-hexadecylamine, n-ocadecylamine (stearylamine) and bis-n-octadecylamine. Isoalkyl-substituted amines include isopropylamine, isobutylamine, t-butylamine, 1-methyl-butylamine, 1,3-dimethyl butylamine, 3,3-dimethyl-butylamine, 2-amino-3,3-dimethylbutane, 1-ethyl-propylamine, 1,5-dimethylhexylamine, t-octylamine, 2- and 3-decylamine (Armeen L-10 a trademark for ARMAK beta-amines sold by Armak Industrial Chemicals, Chicago, Illinois), t-dodecylamine, t-tetradecylamine, and Primene-81R (a mixture of t-$C_{12}H_{25}NH_2$ to t-$C_{14}H_{29}NH_2$ having a neutralization equivalent of 191, sold by Rohm and Haas, Phil. PA), 1-methyl-heptadecyl-amine, t-octadecylamine, t-docosylamine, and Primene JM-T (a mixture of t-$C_{18}H_{37}NH_2$ to t-$C_{22}H_{45}NH_2$ with a neutralization equivalent of 336, sold by Rohm and Haas). Alicyclic amines include cyclopentylamine, cyclohexylamine, dicyclohexylamine, cyclohexanemethylamine, cyclooctylamine, cyclododecylamine and 1-adamantanamine; useful unsaturated monoamines, such as alkenylamines and alkynylamines, include allylamine, 2-methylallylamine, N-methylallylamine, diallylamine, 1-ethynylcyclohexylamine propargylamine, di-propargylamine, myristoleylamine, palmitoleylamine, oleylamine and linoleylamine (Armak).

Also included in the repertory of useful monoamines are the hydroxy substituted monoamines. Suitable hydroxy containing monoamines include 2-aminoethanol, 2-methylaminoethanol, 2-amino-1-propanol, 3-aminopropanol, 2-amino-1-butanol, 4-aminobutanol, 2-t-butylaminoethanol, 2-anilinoethanol, 2-benzylaminoethanol, 2-amino-1-phenylethanol, ephedrine, and diethanolamine. Useful aromatic amines wherein A represents an aryl, alkaryl or aralkyl group include: aniline, anisidine, toluidine, ethylaniline, N-methylaniline, 2-aminobiphenyl, 4-aminobiphenyl, benzylamine, dibenzylamine, phenethylamine, N-phenylbenzylamine, 4-phenylbutylamine, diphenylethylamine, 1-naphthylmethylamine, and tyramine.

In some cases, heterocyclic amines find use in the present invention. Suitable ring compounds preferably those containing 5 to 6 members, can be unsaturated, and may bear alkyl, alkenyl, aryl, alkaryl or aralkyl groups. Substituents may incorporate such heteroatoms as sulfur, oxygen or other nitrogen atoms in the ring system. Such heterocycles include, iter alia, thiophene, benzothiophene, thianthrene, furan, pyran, chromene, xanthene, pyrrole, imidazole, pyrazole, pyridine, pyrazine, pyrimidine, pyridazine, indole, purine, quinoline, naphthyridine, cinnoline, carbazole, acridine, thiazole, dithiazole, thiazine, phenothiazine, oxazole, furazan, chroman, pyrrolidine, imidazoline, pyrazoline, piperidine, piperazine and morpholine. Heterocyclic-bearing amines of preference encompass the amino-alkyl substituted morpholines, piperidines and piperazines.

2. Polyamines

An especially preferred class of amines for constructing highly potent thio-bis-acylated nitrogen products of the present invention are the polyamines. Such polyamines include those featuring the formula:

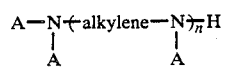

where alkylene represents a hydrocarbyl group containing about 2-6 carbon atoms in a linear or branched configuration, and n varies from 1 to 20.

Preferably, A is hydrogen or an alkyl group of up to 10 carbon atoms which may be substituted with one or two hydroxyl groups. Especially preferred are the alkylene polyamines wherein A is hydrogen or an alkyl group of up to 10 carbon atoms which may be substituted with one or two hydroxyl groups. Especially preferred are the alkylene polyamines wherein A is hydrogen or an alkyl group such as methyl. Representative alkylene polyamines include ethylene polyamines, propylene polyamines, butylene polyamine, etc., and the higher homologs of such amines and related aminoalkyl-substituted piperazines are also included. Examples of suitable polyamines include ethylenediamine (EDA), N,N'-dialkyl-EDA, (where alkyl can be methyl, ethyl, benzyl), 1,2-dianilinoethane, 1,2-diamino-2-methylpropane, 2-aminoethylpiperidine, 2-aminoethylpyrrolidine, 2-aminoethylmorpholine, 2-aminoethylpyridine, 1,3-propanediamine, N-alkyl-1,3-propanediamine (alkyl can be methyl, ethyl, propyl, cyclohexyl), N,N'-dimethyl-1,3-propanediamine, N-(3-aminopropyl) morpholine, 1,4-butanediamine, 2-butene-J,4-diamine, 1,6-hexanediamine, N,N'-dialkyl-1,6-hexanediamine (where alkyl can be methyl, ethyl butyl, benzyl), 1,8-octanediamine, 1,10-decanediamine, diethylenetriamine, (DETA) N,N-dimethyl-DETA, 1,4-dimethyl-DETA, 4-n-butyl-DETA, 1,1-4-trimethyl-DETA,4-(2-aminoethyl)-DETA, N-[2-(aminoethyl)aminoethyl]-piperidine, N[2-(2-aminoethyl)aminoethyl]morpholine, N-[2-aminoethyl)aminoethyl]-pyrrolidine, N-(3-aminopropyl)ethylene diamine (EDA), N(4-aminobutyl) EDA, spermidine, N(4-amino-2-butenyl)-EDA, 3,3'-imino-bis-propylamine, 3,3-methylimino-bis propylamine, 1,5,9-trialkyl-1,5,9-triazanonane (alkyl can be methyl, ethyl, benzyl), 6,6'-imino-bis-hexylamine, N,N',N''-trialkyl-7-aza-tridecane-1,13-diamine (alkyl can be methyl or ethyl), triethylenetetramine (TETA), 4,7-dimethyl-TETA, N,N'-bis-[2-aminopropyl]ethylenediamine, N,N'-bis-[4-aminobutyl]-EDA, N,N'-bis-[3-aminopropyl]-1,3-propanediamine, 6,10-dimethyl-2,6,10,14-tetraazapentadecane, spermine, N,N'-bis-[4-aminobutyl]-1,3-propanediamine, N,N'-bis-[4-amino-2-butenyl]-1,3-propanediamine, tetraethylenepentamine (TEPA), and mixtures of polyethylene polyamines available from Dow Chemical Co., Midland, MI; 4,8,12-triazapentadecane-1,15-diamine, pentaethylene hexamine, pentapropylenehexamine and mixtures of polypropylene polyamines available from BASF Wyandotte Corporation, Parsippany, N.J.

Also useful are the hydroxy polyamines, i.e., alkylene polyamines having one or more hydroxyalkyl groups on the nitrogen atoms, particularly those in which the hydroxylalkyl group contain 4 or less carbon atoms. Examples of suitable hydroxylalkyl-substituted polyamines include N(2-hydroxyethyl)-ethylenediamine, N,N'-bis-(2-hydroxyethyl) EDA, N,N-bis-(2-hydroxyethyl)-1,3-propanediamine, and N,N'-bis (2-hydroxy ethyl)1,6-hexanediamine.

3. Polyoxyalkylene Polyamines

Other polyamines which may be used for purposes of this invention include the polyoxyalkylene polyamines which can be characterized by the formula:

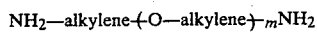

where the alkylene groups may be straight or branched chains and contain from 2 to 6 carbon atoms and m can vary from about 2 to about 40, preferably about 2 to 10. Examples of alkylene groups include —CH$_2$—CH$_2$—,—CH$_2$CH$_2$CH$_2$—,—CH$_2$CH(CH$_3$)—and —CH$_2$-CH—(CH$_2$CH$_3$)—. The polyoxyalkylene polyamines are commercially available from the Jefferson Chemical Company, Inc. (Jeffamines D-230, D-400, T-403, etc.), and Union Carbide Corporation (polyglycol diamine H-221, NH$_2$CH$_2$CH$_2$CH$_2$OCH$_2$CH$_2$OCH$_2$CH$_2$OCH$_2$CH$_2$CH$_2$NH$_2$ being one example).

4. Macrocyclic Amines (Aza Crown Compounds)

A unique class of amine reactants useful for designing cage-like thio-bis-acylated nitrogen compounds with potential as multifunctional additives is typified by the Aza crown compounds:

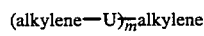
HN V
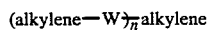

wherein U, V and W can be NH, S and/or O, n or m is an integer of 0 to about 4, alkylene is defined above, but is frequently an ethylene or trimethylene group in the above macrocyclic amines, and embraces macrocyclic polyamines (U=V=W=NH), polyether amines (U=V=W=O; U=W=O, V=NH, etc.) and polythioether amines (U=V=W=S; U=W=S, V=NH); and said macrocycles contain about 9 to about 60 atoms in the ring and depending on U, V and W, are capable of complexing with a wide spectrum of cations such as first row transition metals, the alkali metals, the alkaline earth metals most heavy metals; and the ligand to metal ratio is moost often 1:1.

Macrocyclic polyamines and their complexes having three to about eight nitrogen atoms are preferred, particularly those having four nitrogen donors in cycles containing about 12 to 16 atoms as such or complexed with a first row transition metal such as copper, cobalt, nickel, iron, etc. Examples of useful macrocyclic polyamines include 1,4,8,11-tetraazacyclotertradecand (cyclam), 1,4,7,10-tetrazacyclododecane,

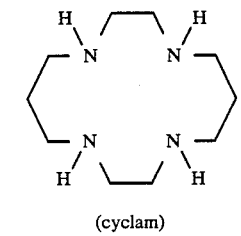

(cyclam)

1,4,7,10-tetraazacyclotridecane, 1,4,8,12-tetraazacyclopentadecane, 1,5,9,13-tetraazacyclohexadecane, and macrocyclic polyamine derivatives VIa and VIb and their metal complexes generated in the condensation reaction of mono-and dicarboxylic acid reactants, such as alkanoic acids and substituted succinic acid anhydrides, with polypropylene polyamines containing from 3 to 8 nitrogen atoms per chain, where R is as defined above, and m can assume values of 0 to about 10.

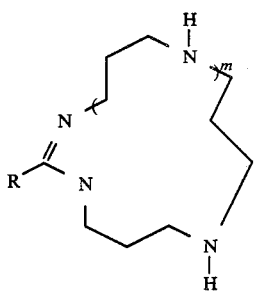

VIa

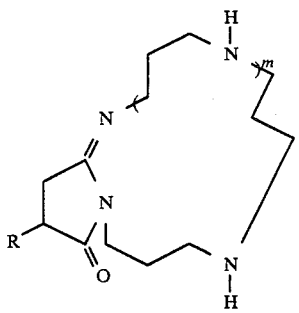

VIb

In another embodiment, mixed donor macrocyclic amines, namely, cycles which contain nitrogen-oxygen, (polyether amines) (VIIa), nitrogensulfur (polythioether amines) (VIIb), and nitrogen-oxygen-sulfur donor groups (VIIc) as depicted below, as well as their metal complexes, can be thio-bis-acylated to give a broad spectrum of valuable multifunctional additives.

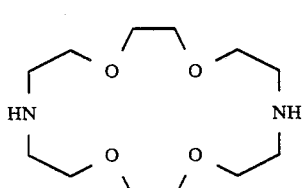

VIIa

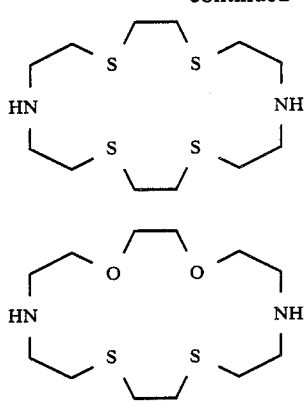

AMIDATION METHODS

A number of synthetic options for designing novel thio-bis-acylated nitrogen systems has been devised in the present invention. The structural features and activity of the thio-bis-acylated polyamine dispersants and antioxidants of this invention is contingent on the nature of the acylating reagent, the type of amine reactant, the molar proportion of these reagents involved in the amidation reaction, and the presence of certain metals in the amidated product.

Accordingly, amidation of the thio-bis-acylating reagents such as (i) thio-bis-(lactone acid/ester/anhydride), (ii) thio-bis-(hydrocarbyl diacid anhydride), and (iii) the $SCl_2$/olefin diacid anhydride reagent, can be effected via (a) a conventional amidation process or (b) a template procedure which involves amide formation in the presence of a metal template reagent, i.e., a metal ion species such as as a salt of copper, cobalt, nickel, iron, zinc, etc., to yield metal complexes.

Conventional Amidation Route

One of our preferred synthetic modes contemplates the amminolysis of (i) thio-bis-(lactone acid/ester) reagents as featured by IV with about half to two moles of amine reagent. Sometimes the conventional process can be facilitated by the use of a promoter such as a carbodiimide

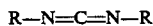

Which usually generates monomeric and/or dimeric macrocyclic anhydride derivatives of the thio-bis-(lactone acid) reactant. Typically, the reagents are mixed and heated in the presence of an azeotroping solvent (e.g., xylene) if desired, at 100°–250° C. preferably at 120°–200° C. until infrared analysis of the reaction indicates that amidation is maximal.

Amminolysis of thio-bis-(lactone acid/ester) reagents with monoamines, either primary of secondary amines, can yield depending upon reaction temperature, stoichiometry, and amine structure, various kinds of amidated products comprising amic acid (Ia, G=NA$_2$, G'=OH), amic acid amine salts (Ia, G=NA$_2$, G'=OH.HNA$_2$), or bis-amide products (Ia, G=G'=NA$_2$). In certain cases, primary mono-amines when reacted with thio-bis-(lactone acid) agents in a 1:1 molar ratio give initially amic acids which under suitable reaction conditions, can macrocyclize to the cyclic imide product (Ia in which G+G'=NA). Amidation of IV (1:1 reactant ratio) with selected polyamines, 1,3-propanediamine for example, affords a macrocyclic imide, i.e., G+G'=NCH$_2$CH$_2$CH$_2$NH$_2$ which upon heating cyclizes (via back-biting) to a bicyclic amidine structure (see Example C18). With gem-substituted polyamines such as 1,2-diamino-2-methyl propane, another cyclization pathway is observed, and thio-bis-(lactone imidazolines) are formed (see Example C17).

Secondary polyamines amidate IV to give (1:1) amic acids which upon heating (with promoter if desired) yield macrocyclic bis-amides (see Examples C21 and C22). With polyamines bearing $\alpha,\omega$-diamine functionality, e.g., polyethylene polyamine, and/or its partially acetylated derivative, the equimolar condensation reaction with thio-bis (polyisobutyl lactone acid) gives substantial amounts of macrocyclic products (Ia) wherein G+G' represents a polyamine chain bonded in both intra- and intermolecular modes depending upon reaction conditions and polyamine composition. Moreover, the 1+1 macrocycle ring size will also be governed by polyamine chain length and the presence of other species such as metal ions.

Depending on experimental conditions, the type of thio-bis-(alkyl lactone acid) reactant and polyamine structure, amidation of IV can also engender imides via lactone ring opening (lactonolysis by polyamine) to give, inter alia, products related to Ic wherein J=OH, L=H, A+A' represents a polyamine chain tending to form macrocycles via inter- and intramolecular modes.

It is noted that type IV reactants with highly substituted lactone groups, e.g., thio-bis-(polyisobutyl lactone acid) are less prone to amine-induced lactonolysis. Moreover, polyamines which are pacified via acetylation or complexation, as expected, amidate IV-type reactants with minimal lactonolysis to afford substantial amounts of thio-bis-(lactone amide) products.

In another embodiment, we contemplate the amidation of (ii), the thio-bis-(hydrocarbyl diacid) reagents III and V with about 1 to 4 moles of amine depending upon the nature of the amine and the kind of thio-bis-acylated amine product desired. With secondary monoamines, a spectrum of products ranging from mono to tetra amides can be envisioned using Formula Ib wherein G and G' would represent $R_2N-$ and OH groups, and L=J=H or L+J=a pi ($\pi$) bond. Amidation with secondary polyamines would engender macrocyclic species wherein G+G' in Formula Ib is a polyamine chain tending to bridge succinic acid groups together in both intra- and inter-molecular modes depending on reaction conditions. By contrast, primary monoamines, while forming amic acids initially, would ultimately engender imide structures illustrated by Formula Ic wherein J=L=H or J+L=a pi ($\pi$) bond. Polyamines (1:1 reactant ratio) with $\alpha$, $\omega$-primary amine functions would also give amic acids which, upon further reaction, would ultimately collapse into macrocyclic imides portrayed in Ic wherein J=L=H or J+L=a pi bond, and A+A' represents a polyamine chain again bridging via inter- and/or intramolecular modes to produce 1+1 and larger macrocycles.

In still another embodiment, amidation of (iii) sulfur halide/olefin diacid adducts (II) with secondary monoamines affords amic acids (Ib, wherein J=Cl, L=H; G=OH, and G'=NR$_2$) which can in the presence of excess base collapse via internal loss of HCl (G=OH displaces J in Ib) to generate lactone amides (Ia). To a degree, the adducts (II) in the presence of excess amine engender products similar to those afforded in the amidation of IV. However, under certain amidation conditions, II can be envisioned to collapse into other kinds of amide and imide products.

Typically, dispersant formation is carried out by adding about one mole of amine, preferably polyamine, per 0.5 to 1 mole of thio-bis-(lactone acid or ester) or thio-bis-(hydracarbyl diacid anhydride) with or without an inert diluent, in the presence of a promoter if necessary, and heating the mixture at 50°–240°, preferably 80°–180° C. until reaction is complete by infrared analysis of the product as indicated by maximal adsorptions for amide and/or imide functionality.

Variations, however, in the molecular weight and composition of the sulfur-bridged acylating agent, as well as the molecular weight and chain length of the polyamine may be necessary, depending upon utility, since these factors sensitively affect the hydrophilic-lipophilic balance, solubility and the viscosity of the additive.

For example, it has been found that thio-bis-acylated nitrogen dispersants obtained from the reaction of one mole of bis-thio-(alkyl lactone acid) (IV) or a dehydrohalogenated $S_xCl_2$— olefin diacid anhydride adduct (III), (derived from polyisobutenyl succinic anhydride with $M_n = 1050$ and a Saponification number of 78) with one mole of polyamine (viz., tetra-ethylene pentamine) feature outstanding dispersant properties.

The superior stability and dispersant properties exhibited by the aminetreated sulfur-bridged lactone acid and sulfur-bridged hydrocarbyl diacid materials of the present invention over the prior art compositions, namely adducts of polyisobutenyl succinic anhydride and amines such as polyamines, may be related in part to the presence of sulfide functionality and in part to the macrocyclic and macrocyclic-like configurations assumed by the polar heteroatoms in some of the dispersant molecules.

In another embodiment of the present invention, one can sometimes achieve the design of thio-bis-acylated nitrogen compounds by first reacting an olefin diacid anhydride with a mono- or polyamine to afford the imide and/or the amic acid derivatives which are subsequently bridged via treatment with chlorosulfenylating agent such as sulfur chloride which under suitable conditions can effectively add to the double bond of the olefin diacid imide and/or amic acid species. In the case of polyamine-treated olefin diacid anhydrides, the amic acid and/or imide precursors must be pre-treated with a metal salt, or an acylating agent, or a reagent such as acid, e.g., acetic acid, which can completely pacify those basic sites present in the adduct which would ordinarily, decompose the chlorosulfenylating agent in the subsequent sulfur-bridging step.

Metal Assisted Cyclizations

While the conventional approach to amidation provides access to a wide spectrum of novel macrocyclic and macrocyclic-like amide and/or imide products, the optional metal template procedure offers synthetic route to the metal complexes of the macrocyclic ligands produced in the equimolar reaction of polyamine and thio-bis-acylating agents. In the metal-assisted process, the cation species tends to enhance yields of macrocycles by forming a template about which the sulfur-bridged acylating agent and polyamide molecules condense into a macrocyclic species which is isolated as its metal complex. It is thought that complex formation with either or both reactants favors intramolecular amide formation relative to the intermolecular process which affords polymer product. Factors such as metal ion size, and the chain length of the polyamine will dictate the relative yields of 1:1, 2:2 and larger macrocyclic complexes formed in the equimolar reaction of the thio-bis-acylating agent and polyamine. In general, the overall yields of cyclic products are magnified at the expense of linear oligomer as a consequence of the directive influence of the metal ion (template effect). A variety of metal ions particularly those selected from the first row transition metals including iron, cobalt, nickel, copper, chromium, manganese, are effective template reagents; other useful metal ions include molybdenum, tungsten, ruthenium, palladium, platinum, cadmium, lead, silver, mercury, anitmony, and bismuth.

The templating action of the above metal species can be realized by (1) adding the metal salt directly to the reaction mixture comprizing equimolar amounts of the thio-bis-acylating agent and polyamine reagent, or by (2) pre-reacting the metal ion with one of the reactants to (i) form a metal carboxylate of the thio-bis-acylating agent or (ii) a metal complex of the polyamine reagent and subsequently effecting amidation of the metal containing mixture. In another embodiment, a metal complex of the amic acid and/or imide derivative of an olefin diacid reactant is first formed and then bridged with a chlorosulfenylating agent such as a sulfur chloride. Accordingly, in harmony with synthetic option (1), metal-assisted cyclizations are effectuated by simply adding a molar amount of a metal salt, e.g., cupric acetate, to an equimolar mixture of a thio-bis-acylating agent, e.g., thio-bis-(lactone acid) and a polyamine and heating the mixture in a suitable diluent such as tetrahydrofuran or xylene at about 50°–180° C. until the amidation process appears complete by infrared analysis.

As disclosed above, macrocyclic formation via option (2) can be accomplished using several synthetic variations including (i) the reaction of a metal carboxylate salt of a thio-bis-(lactone acid) with a polyamine; (ii) the reaction of a metal-polyamine complex with a sulfur bridged acylating agent such as a thio-bis-(lactone acid) (IV) or a dehydrochlorinated $SCl_2$-alkene diacid (III) or (V) or (iii) the process of forming a metal complex of an amic acid or imide prepared from two moles of an alkenylsuccinic anhydride and a mole of polyamine, and subsequently bridging the neutralized or pacified amic acid and/or imide with a sulfur halide.

Judging from gel permeation chromatography measurements on the products of these processes, it is evident that the presence of a metal ion during amidation tends to increase the yield of macrocycles over linear products from competing linear oligomeric processes. The ability to influence the mode of amide and/or imide formation with metal salts provides a versatile approach to the design of amide and/or imide complexes with superior performance characteristics.

USE OF AMINATED THIO-BIS-(ALKYL LACTONE ACID) AND THIO-BIS-(HYDROCARBYL DIACID MATERIALS AS ADDITIVES IN OLEAGINOUS COMPOSITIONS

The oil-soluble sulfur-bridged amide and/or imide products and their metal complexes of the invention can be incorporated in a wide variety of oleaginous compositions. They can be used in lubricating oil compositions, such as automobile crankcase lubricating oils, automotive transmissions fluids, ets., generally within the range of about 0.01 to 20 Wt. %, e.g., 0.1 to 10 Wt. %, preferably 0.3 to 3.0 Wt. %, of the total composition. The lubricants to which the thio-bis-acylated nitrogen products can be added include not only hydrocarbon oils derived from petroleum but also include synthetic lubricating oils such as polyethylene oils; alkyl esters of dicarboxylic acid; complex esters of dicarboxylic acid; complex esters of dicarboxylic acid, polyglycol and alcohol; alkyl esters of carbonic or phosphoric acids; polysilicones; fluorohydrocarbon oils, mixtures of mineral lubricating oil and synthetic oils in any proportion, etc.

When the products of this invention are used as multifunctional additives having detergent and antirust properties in petroleum fuels such as gasoline, kerosene, diesel fuels, No. 2 fuel oil and other middle distillates, a concentration of the additive in the fuel in the range of 0.001 to 0.05 Wt. %, based on the weight of the total composition, will usually be employed.

When used as an antifoulant in oleaginous, e.g., mineral oil streams in refinery operations to prevent fouling of process equipment such as heat exchangers or in turbine oils, about 0.001 to 2 Wt. % of the inventive additive, preferably a polyamine-treated thio-bis-(alkene dioic acid) (III) will generally be used.

The additive may be conveniently dispensed as a concentrate comprising a minor proportion of the additive, e.g., 20 to 90 parts by weight, dissolved in a major proportion of a mineral lubricating oil, e.g., 10 to 80 parts by weight, with or without other additives being present.

In the above compositions or concentrations, other conventional additives may also be present including dyes, pour point depressants, antiwear agents such as tricresyl phosphate or zinc dialkyldithio phosphates of 3 to 8 carbon atoms in each alkyl group, antioxidants, such as N-phenyl-α-naphthylamine, tert-octylphenol sulfide, 4,4'-methylene bis-(2,6-di-tert-buytl phenol), viscosity index improvers such as ethylene-propylene copolymers, polymethacrylates, polyisobutylene, alkyl fumarate-vinyl acetate copolymers and the like, deemulsifiers such as polysiloxanes, ethoxylated polymers and the like.

SYNTHESIS OF ALKENE DIACID REACTANTS

A wide spectrum of alkene diacid materials, amenable to sulfur bridging reactions, can be designed via the reaction of maleic anhydride with an olefin or chlorinated olefin. Both routes to alkenylsuccinic anhydrides involve heating the olefin or chloro-olefin reactaft and maleic anhydride together in the presence of catalytic amounts of inhibitor at about 180°–260° C. for 1–24 hours until sufficient adduct is formed. Depending on availability and cost of starting materials, a 1.1–2 fold excess of either reactant can be employed to increase the rate of adduction and yield of alkenyl succinic anhydride. When excess maleic anhydride is employed, varying amounts (10–40% yields) of alkenyl di-, tri-, and poly-succinic anhydrides accompany the mono-adduct together with minor amounts (5–25% yields) of unreacted olefin. Since the mono-adduct is the preferred species for the purpose of this invention, it is advantageous to employ excess olefin in adductions with maleic anhydride. High molar ratios (1.5–10) of olefin to maleic anhydride afford substantial yields (50–80%) of olefin diacid products comprising Ene structures as

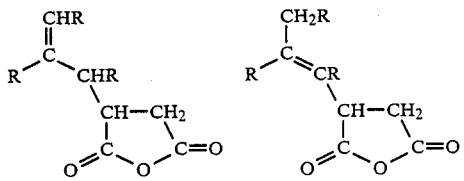

By way of contrast, the reaction of chloroalkenes and maleic anhydride proceeds via an elimination rearrangement pathway to give in part, Diels Alder products comprising such structures as:

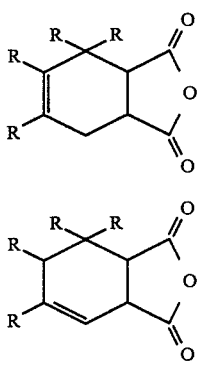

the R group on the Ene or Diels-Alder adducts may be hydrogen, or hydrocarbyl each having from 1 to 400 carbons. The most preferred alkenyl succinic anhydrides are those derived from such olefins and chloroalkenes as isobutylene, diisobutylene, chloro diisobutylene, n-octene, tetraproplyene, n-octadecene, polypropylene, polyisobutylene ($M_n$ 800 and 1050) and chloropolyisobutylene ($M_n$ 800 and 1050). The monochloro olefins, judging from spectral and chemical behavior, are predominantly allylic in character.

The $C_4$–$C_{18}$ olefins and chloro diisobutylene are reacted with maleic anhydride (excess alkene used), at atmospheric pressure or when required, as with isobutylene, and diisobutylene, under pressure (120°–260° C.) for 4–16 hours. The alkenyl succinic anhydride products from $C_4$–$C_{18}$ olefins and chloro diisobutylene were vacuum distilled and heart cuts were taken for sulfur bridging to give model thio-bis-(acylating agents) essentially free of bridged alkenyl di-, and tri-succinic acid anhydrides.

The polyolefin diacid anhydrides were usually prepared by heating about 1–2 moles of maleic anhydride with about 1 mole of polyolefin at about 200°–280° C. in the presence of an inhibitor (1–2 Wt. % of PARABAR 441) at 1–200 psi for 8–16 hours. The degree of functionalization was assessed by the (i) saponification number of the polyalkene diacid anhydride, and (ii) chromatographic analysis (on silica gel) of polyolefin diacid for active ingredient present in the reaction mixture. Judging from the saponification numbers and chromatographic analyses for active ingredient, it appears that most polyalkenyl succinic anhydrides contained modest amounts (5–20 wt. %) of bis- and tri-succinic anhydrides and 10–30 wt. % of unreacted polyalkenes.

In the light of the compositional data for the polyalkenyl succinic anhydrides, the present invention also teaches the sulfur halide-induced bridging of alkenyl bis- and tris-succinic anhydrides present in the various polyisobutenyl succinic anhydrides (PIBSA) and chloro-PIBSA reactants. Accordingly, when reference is made to sulfur bridged PIBSA reactants and products, the presence of bridged PIB(SA)$_y$ (where PIB refers to polyisobutenyl, SA refers to succinic anhydride and y is 2,3 or more) is implied in most cases.

The alkenyl succinic anhydride reactants used in designing the thio-bis-(acylating) agents of the present invention are featured below:

tion mixture was allowed to warm up to room temperature and stirred for a few hours. The methylene chloride was removed by rotoevaporation at 50° C. for 2 hours. Thbe concentrate featured an infrared spectrum with af intense anhydride carbonyl absorption band at about 5.67 microns and a gel permeation chromogram with a single peak corresponding to the bridged product.

| | | | | ASA | |
|---|---|---|---|---|---|
| Process | Olefin | Olefin Mol Wt (1) | Alkenyl Succinic Anhydride (ASA) | Sap. Number (2) | Mw (1) |
| Ene | Isobutylene | 56 | Isobutenyl-SA (IBSA) | 720 | 154 |
| | Di-isobutylene | 112 | Di-isobutenyl-SA (DIBSA) | 553 | 210 |
| | n-octene | 112 | n-octenyl-SA (NOSA) | 550 | 210 |
| | tetraisobutylene | 168 | tetraisobutenyl-SA (TBSA) | | 268 |
| | octadecene | 252 | octadecenyl-SA (OSA) | 310 | 375 |
| | polypropene | | polypropenyl-SA (PPSA) | 92 | 623 |
| | polyisobutylene | | polyisobutenyl-SA | | |
| | | 758 | (PIBSA) | 84 | 776 |
| | | 812 | PIBSA | 112 | 757 |
| | | 1050 | PIBSA | 72 | 1080 |
| Diels-Alder | Cl—Diisobutylene | 146 | Cl—DIBSA (3) | | |
| | Cl—polyisobutylene (4.1% Cl) | 800 | Cl—PIBSA (4) | 80 | 751 |
| | | | Cl—PIBSA | 112 | 771 |
| | Cl—polyisobutylene (4.0% Cl) | 1010 | Cl—PIBSA | 103 | 1044 |

ALKENYL SUCCINIC ANHYDRIDE (ASA) PRECURSORS TO THIO-BIS-(ACYLATING AGENTS)

(1) Polyolefin and polyalkenylsuccinic anhydride molecular weights (Mn) determined by Gel Permeation Chromotography (GPC).
(2) Saponification number according to AM-S 500.23.
(3) 3,3,4,5-tetramethyl-1,2,3,6-tetra-hydrophthallic anhydride.
(4) For convenience, Ene and Diels-Alder PIBSA will be identified as PIBSA and Cl—PIBSA, respectively.

A. SYNTHESIS OF MODEL THIO-BIS-(ACYLATING AGENTS)

In the following examples, synthetic procedures are described for bridging the Ene and Diels-Alder products depicted above and their diacid, hemi-ester and diester analogs. Various modes of bridging as a function of bridging agent, bridging temperature, and reactant ratio will be outlined in detail. Moreover, a number of examples will also be put forth to illustrate the conversion at the $S_xCl_2$-olefin diacid adducts into other useful thio-bis-(acylating agents) including bridged alkene diacid anhydrides, and alkyl lactone acids, and esters.

In the first seven examples, the coupling (or bridging) of a model alkene diacid reactant, i.e., isobutenyl succinic anhydride (IBSA) with several bridging agents including $SCl_2$, $S_2Cl_2$, and $SeCl_4$ using various solvents and temperatures; and the conversion of $S_xCl_2$-IBSA adducts into lactones, sulfoxides and sulfones will be elaborated.

EXAMPLE A1

Adduct of $SCl_2$ and Isobutentyl Succinic Anhydride (IBSA)

Two tennis mole (30.8 g) of isobutenylsuccinic anhydride (IBSA) were dissolved in 100 ml of methylene chloride and 0.1 mole (10.3 g) of $SCl_2$ were added dropwise at 0° C. while under a nitrogen blanket. The reaction was very exothermic, but no HCl evolution was observed. When the addition was completed, the reac-

EXAMPLE A2

Adduct of $SCl_2$ and IBSA at 100° C.

About 77 g (0.5 mole) of isobutenyl succinic anhydride were dissolved in a very small amount of THF (10 ml) and heated slowly to 100° C. Then, 0.35 mole (40 g) of $SCl_2$ were added dropwise for a period of one half hour. When the addition was completed, the reaction mixture was kept at 100° C. for half an hour while stirring under a nitrogen blanket and then nitrogen sparged at 100° C. for another half hour. The infrared spectrum of the product featured a strong anhydride carbonyl absorption band at 5.65 microns; GPC analysis indicated that the product was completely bridged.

EXAMPLE A3

6,6'-Thio-Bis-(5-Methyl-3,5-Carbolactone-Hexanoic Acid)

Two tenths mole (30.8 g) of isobutenyl succinic anhydride (IBSA) was dissolved in 100 ml of THF and 0.1 mole (10.3 g) of $SCl_2$ were added at 0° C. The reaction mixture was warmed up to room temperature and stirred for four hours. Then, 0.2 mole (3.6 g) of water was added and the reaction mixture was refluxed for several hours to assure complete lactonization. Infrared analysis of the reaction product revealed complete conversion to the desired thio-bis-(lactone acid).

In the same manner, 6,6'-dithio-bis-(5-methyl-3,5-carbolactone-hexanoic acid) was prepared via the reaction of IBSA and S₂Cl₂ according to the procedure described above.

EXAMPLE A4

6,6'-Thio-Bis-(5 Methyl-3,5-Carbolaconte-Hexanoic Acid Via Isobutenyl Succinic Acid Two tenths mole (30.8 g) of IBSA were dissolved in 100 ml of THF and mixed with 0.2 mole (3.6 g) of water. The reaction mixture was refluxed until infrared analysis indicated complete conversion to the diacid product. Then, the solution was cooled to room temperature and 0.1 mole (ea. 10.3 g) of SCl₂ was added dropwise for a period of half an hour. An exothermic reaction took place and gas evolution was observed. The mixture was refluxed in THF for 4 hours to assure complete conversion. The infrared analysis of the product confirmed the presence of the desired thio-bis (lactone-acid).

EXAMPLE A5

Sulfoxide of the SCl₂-IBSA Adduct

Two tenths mole (ca 30.8 g) of isobutenyl succinic anhydride were dissolved in 100 ml methylene chloride. The resulting solution was stirred at 0° C. and then bridged via the dropwise addition of 10.3 g (ca 0.1 mole) of SCl₂. After the addition was completed, the reaction mixture was allowed to stir at room temperature for a few hours.

To the above adduct, 20.2 g (0.1 mole) of 85% metachloroperbenzoic acid was added spoonwise for a period of one hour. An external cooling bath was provided to keep the reaction about room temperature. After the addition was completed the clear solution was stirred at room temperature for several hours. During this period the chlorobenzoic acid which precipitated out of solution was filtered. The filtrate was cooled to 0° C. and more acid was filtered. This operation was repeated several times until the infrared spectrum of the filtrate showed the absence of metachlorobenzoic acid.

The CH₂Cl₂ solution was dripped into a large volume of ether and a white solid formed. The mass spectrum of the product featured a substantial peak at m/e 356 for the dehydrochlorinated bridged sulfoxide product.

EXAMPLE A6

Sulfone of the SCl₂-IBSA Adduct

Oxidation of the SCl₂-IBSA adduct described in Example A5 with 0.2 mole of m-chloroperbenzoic acid afforded the desired sulfone derivative.

EXAMPLE A7

Adduct of Selenium (IV) Chloride and IBSA

Three tenths (ca 46.2 g) of IBSA were dissolved in 100 ml of chloroform and 25 g (0.11 mole) of selenium (IV) chloride were added at room temperature while under a nitrogen blanket. The exothermic reaction was maintained about 20° C. via an external cooling bath. No HCl evolution was observed. When the addition was completed, the reaction mixture was allowed to stir at room temperature for 12 hours - the chloroform was rotoevaporated at 100° C. for an hour. The GPC analysis of the residue showed substantial bridging.

The following examples illustrate the (1) sulfenylation of diisobutenyl succinic acid, anhydride, DIBSA hemi-ester, and diester with SCl₂ and S₂Cl₂ at ambient and 100° C. temperature, with and without solvent using reactant ratios of 1:1 and 2:1; and (2) conversions of the S$_x$Cl₂-olefin diacid adducts to thio-bis-(alkyl lactone acids and esters) and thio-bis-(alkene diacids and diesters).

EXAMPLE A8

Dehydrochlorinated Adduct of SCl₂ and Diisobutenylsuccinic Anhydride

Three-tenths mole (63 g) of diisobutenylsuccinic anhydride (DIBSA) dissolved in 100 ml of methylene chloride was bridged with 0.15 mole (15.5 g) of sulfur dichloride (SCl₂) by adding the SCl₂ dropwise to the anhydride at about room temperature. External cooling was needed to maintain the exothermic bridging process at about 25° C. The reaction mixture was maintained over nitrogen for 2 days, and subsequently rotoevaporated at about 50° C. for 2 hours. The concentrate featured an IR spectrum with an intense carbonyl absorption band at about 5.67 microns and analyzed for 58.92% carbon, 7.44% hydrogen, 7.84% sulfur and 4.17% chlorine. Theory requires 55.07% C, 6.93% H, 6.12% S, and 13.56% Cl.

EXAMPLE A9

Dehydrochlorinated Adduct of S₂Cl₂ and Diisobutenylsuccinic Anhydride

A tenth-mole (21.0 g) of diisobutenylsuccinic anhydride in 150 ml of chloroform and 0.05 mole (6.8 g) of sulfur monochloride in 150 ml of HCCl₃ were simultaneously added dropwise to 200 ml of chloroform at about 25° C. After addition, the mixture was stirred at ca 25° C. for 2 days and concentrated by rotoevaportion at ca 25° C.

The concentrate analyzed for 10.31% chlorine and featured a gel chromatogram dominated by a peak corresponding to the S₂Cl₂-diisobutenylsuccinic anhydride adduct. Refluxing the adduct in dioxane for 24 hours gave a concentrate consisting primarily of 5,5'dithio-bis-(4-neopentyl-3(4)-pentene-1,2-dicarboxylic acid anhydride) which analyzed for 2.12% chlorine. A plausible structure for the thio-bis-(alkene diacid anhydride) product, in part, is shown below:

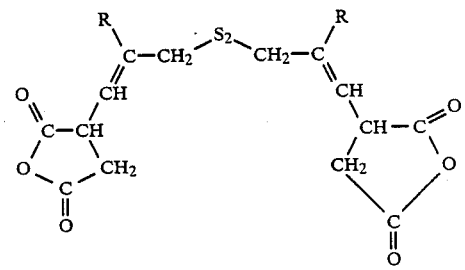

R = neo-pentyl

In a similar manner, diisobutenylsuccinic anhydride (0.05 mole) was sulfenylated with an equimolar amount of sulfur monochloride (S₂Cl₂). The gel chromatogram of the solvent-free product showed a dominant peak ascribable to the sulfur-bridged anhydride product.

EXAMPLE A10

High Temperature Reaction of SCl₂ with Diisobutenylsuccinic Anhydride

Two-tenths mole (42 g) of diisobutenylsuccinic anhydride being stirred at ca 100° C. under a nitrogen atmosphere, was treated dropwise with 0.1 mole (10.3 g) of sulfur dichloride. The reaction temperature (100° C.) was maintained by the controlled addition of $SCl_2$. Following the completion of $SCl_2$ addition, the stirred mixture was maintained at 100° C. using external heating. Gel chromatography of the product revealed that a substantial portion (ca 66%) of the anhydride was bridged by the $SCl_2$. Complete bridging could be achieved by the further addition of $SCl_2$ to the mixture.

EXAMPLE A11

Adduct of $SCl_2$ and Diisobutenylsuccinic Anhydride via Equimolar Reaction

Bridging of 0.05 mole (10.5 g) of diisobutenylsuccinic anhydride (dissolved in 50 ml of $CH_2Cl_2$) was effected by the dropwise addition of an equimolar amount (0.05 mole, 5.2 g) of $SCl_2$ to the anhydride at ca 25° C. The concentrated product featured an IR spectrum with a strong anhydride carbonyl absorption band at 5.67 microns and a gel chromatogram with an intense band corresponding to the bridged anhydride product.

EXAMPLE A12

6,6'-Thio-Bis-(5-Neopentyl-3,5-Carbolactone-Hexanoic Acid)

Two tenths mole (42.0 g) of diisobutylene succinic anhydride (DIBSA) was dissolved in 100 ml of THF and 0.1 mole (10.3 g) of $SCl_2$ were added. During addition, the reaction temperature climbed to about 35° C. and HCl evolution occured. The mixture was refluxed for four hours and then heated to 100° C. (THF distilled off) for two more hours to effect complete dehydrohalogenation.

The residue was cooled and dissolved in THF and 0.2 mole of water and two drops of concentrated sulfuric acid were added. The mixture was refluxed for several hours. Infrared analysis revealed complete conversion to the desired thio-bis-lactone acid pictured below.

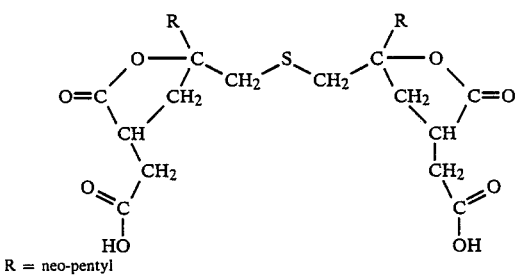

R = neo-pentyl

EXAMPLE A13

6,6'-Dithio-Bis-(5-Neopentyl-3,5-Carbolactone-Hexanoic Acid)

A tenth mole (21 g) of diisobutenylsuccinic acid was prepared via hydrolysis of the corresponding anhydride in refluxing tetrahydrofuran (THF). After IR analysis indicated complete conversion to said diacid, the reaction temperature was elevated to 95° C. by distilling off a sufficient volume of THF solvent. While maintaining a temperature of ca 95°–100° C., 0.05 mole (6.9 g) of sulfur monochloride was added dropwise to the stirred solution. HCl evolution was noted. Rotoevaporation of the reaction mixture gave a concentrate of the product which featured an IR spectrum dominated by an intense lactone carbonyl absorption band at 5.68 microns. The gel chromatogram of the residue show a large band ascribable to the desired sulfur-bridged lactone acid.

EXAMPLE A14

6,6'-Thio-bis-(5-Neopentyl-3,5-Carbolactone-Hexanoic Acid)

Two tenths mole (42.0 g) of DIBSA was dissolved in 100 ml of THF and 0.1 mole (10.3 g) of $SCl_2$ were added. During addition the reaction temperature climbed to about 35° C. and HCl evolution occurred. The mixture was refluxed for four hours and then heated to 100° C. (THF distilled off) for two more hours to effect complete dehydrohalogenation.

The residue was cooled and dissolved in THF and 0.2 mole of water and two drops of concentrated sulfuric acid were added. The mixture was refluxed for several hours. Infrared analysis revealed complete conversion to the above titled thio-bis-(lactone acid).

SULFUR BRIDGED LACTONE ESTER REACTANTS

EXAMPLE A15

Dimethyl 6,6'-Thio-Bis-(5-Neopentyl-3,5-Carbolactone-Hexanoate)

A tenth mole of mono-methyl diisobutenylsuccinate was dissolved in 100 ml of xylene and 0.05 mole of $SCl_2$ was added dropwise to the stirred xylene and rotoevaporated for three hours at 90° C. IR analysis revealed that the hemi-ester/$SCl_2$ adduct was completely converted to the desired thio-bis-lactone methyl ester. A plausible structure for the sulfur-bridged bis-lactone is shown below:

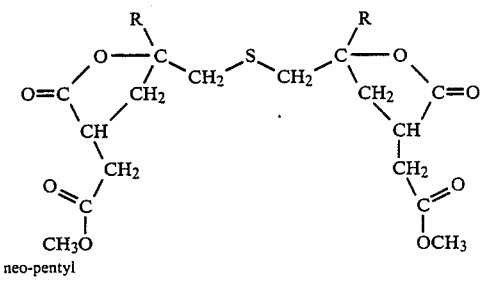

R = neo-pentyl

EXAMPLE A16

Tetramethyl 5,5'-Dithio-Bis-(4-Neopentyl-3,4-Pentene-1,2-Dicarboxylate)

A tenth mole (25.6 g) of dimethyl diisobutenyl succinate in 100 ml $CH_2Cl_2$ was treated dropwise with 0.05 mole (6.8 g) of $S_2Cl_2$ at room temperature. After addition, the reaction mixture was stirred at room temperature for several hours and rotoevaporated at 50° C. for 2 hours. The concentrate featured a gel chromatogram with a dominant peak consistent with the sulfur-bridged ester product, dithio-bis-(alkenylsuccinic acid dimethyl ester), corresponding to a $M_n$ of about 400. Heating the adduct at 225° C. for 2 hours afforded a material with a gel chromatogram similar to that prior to heating. Clearly, the thermolytic conditions imposed on the bridge structures failed to cleave the sulfur-linked acid esters, and demonstrates the stability of the S-bridged esters towards the thermal conditions imposed during the esterification of the bridged structures.

The following examples illustrate the bridging of diisobutenyl succinic anhydride (DIBSA) via successive thiolation and oxidation reactions.

EXAMPLE A17

Tetramethyl 4,4'-Dithio-Bis-(4-Neopentyl-1,2-Pentane-Dicarboxylate)

Two tenths mole (42 g) of diisobutenylsuccinic anhydride was dissovled in 200 ml of $CH_2Cl_2$ and cooled to −70° C. Ten grams of gaseous hydrogen sulfide were then condensed into the reactor at −70° C. The stirred reaction mixture was subsequently treated with gaseous $BF_3$ (1 bubble/sec) for 3 hours at −70° C. The clear colorless solution turned yellow after 1 hour, and upon warming to room temperature, assumed a dark red color.

The solvent was removed and the reaction mixture heated to 120° C. for 1 hour. IR analysis of the mixture showed the presence of thiolactone acid. Further reaction with methanol at 80° C. for 1 hour gave the thiolactone ester shown which was dissolved in ether, washed several times with aqueous $NaHCO_3$, and dried over $MgSO_4$.

Vacuum distillation of the residue afforded 29 g of a fraction, b.p. 128°–130° C. (0.04 mm), which featured an IR spectrum with strong carbonyl absorption bands at 5.73 and 5.86 microns and a proton spectrum consistent with a 5-ring thiolactone ester. Elemental analyses showed 60.59% carbon, 8.53% hydrogen and 12.00% sulfur. Theory requires 60.42% C, 8.58% H and 12.41% sulfur. The proposed structure for the thiolactone ester is featured below:

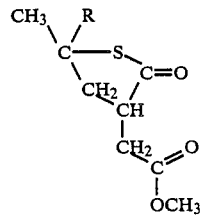

R = neo-pentyl

Oxidation of said thiolactone ester with a mole equivalent of t-butyl hypochlorite in methanol afforded the desired dithio-bis-ester product in high yields.

EXAMPLE A18

Tetremethyl 5,5'-Dithio-Bis-(4-Neopentyl-1,2-Pentane-Dicarboxylate)

A tenth mole (7.6 g) of thioacetic acid and 0.05 mole (10.5 g) of diisobutenylsuccinic anhydride were dissolved in 30 ml of ether and stirred at room temperature overnight. Distillation of the mixture freed of solvent gave a fraction (8.0 g) boiling at 180°–185° C. (0.1 mm). The IR spectrum of the product recrystallized from ether/pentane (m.p. 72°–73° C.) featured intense anhydride and thiol ester carbonyl absorption bands at 5.64 and 5.95 microns. The crystalline product analyzed for 59.03% C, 7.57% H and 10.99% S. Theory requires 58.73% C, 7.57% H and 11.20% S. The proton and carbon magnetic spectra were consistent with the structure of the thioacetyl anhydride intermediate as shown below:

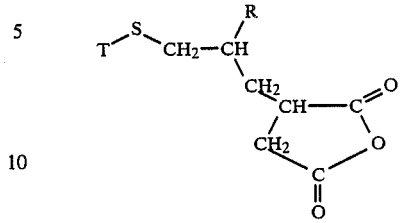

wherein R is neopentyl and T is $CH_3C=O$.

Oxidation of said thioacetyl anhydride was smoothly effected via the dropwise addition of 0.02 mole (2.7 g) of sulfuryl chloride to ca 50 ml of a methanol solution of 0.02 mole (5.72 g) of the thioacetyl anhydride. The addition produced an exotherm and the reaction temperature peaked at ca 50° C. The mixture was stirred at ambient temperatures for about an hour. Gel permeation chromatography (GPC) of the reaction mixture indicated that oxidation coupling was ca 80% complete; accordingly, additional $SO_2Cl_2$ (ca 0.5 g) was added until the GPC of the reaction mixture showed only a product peak. Upon standing, the reaction mixture crystallized. The solids recrystallized from ether/pentane melted at 82°–83° C. and, featured: an IR spectrum with a dominant carbonyl band at 5.72 microns, a proton spectrum with a double methyl proton signal centered at 6.3 tau, and a mass spectrum with a molecular ion peak at 578. The data are completely consistent with the bridged structure shown below. The product analyzed for 58.24% carbon, 8.48% hydrogen, 10.99% sulfur, and 22.24% oxygen. Theory requires: 58.09% C; 8.70% H; 11.08% S and 22.11% O.

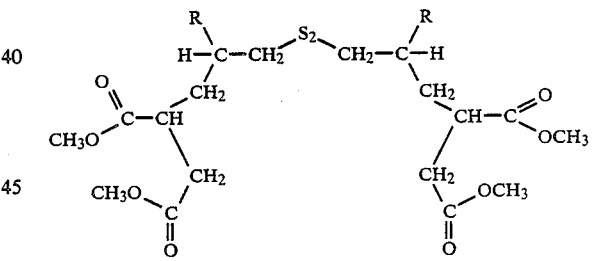

wherein R is neopentyl.

The following examples describe unsuccessful attempts to prepare stable bridged derivatives of Ene and Diels-Alder adducts (DISBA and Cl-DIBSA) via sulfurization with elemental sulfur. Also illustrated is the attempted ENE reaction of alkenyl disulfide with maleic anhydride, which afforded 2-alkylthiasuccinic acid anhydride rather than the desired thio-bis-(acylating agent).

EXAMPLE A19

Sulfurized Diisobutenyl Succinic Anhydride

A mixture of 10.5 g and (0.05 mole) of diisobutenylsuccinic anhydride (DIBSA) and elemental sulfur (0.05 mole, 1.6 g) was heated to 205° C. and maintained at this temperature with magnetic stirring for 5 hours. IR analysis of the reaction mixture showed the appearance of a strong absorption band at 5.9 microns (ascribable possibly to thioanhydride) and a shift in the C=C absorption band from 6.05 to 6.22 microns (attributable possibly to a sulfur-induced isomerization of the C=C double bond). Gel permeation chromatography (GPC) featured an intense peak maximum corresponding to that observed for diisobutenylsuccinic anhydride. A peak in the gel chromatogram corresponding to sulfur-bridged diisobutenylsuccinic anyhdride products, i.e., thio-bis-(diisobutyl succinic anhydride) was conspicuously absent.

EXAMPLE A20

Sulfurization of Cl-Dibsa

A mixture of 3,3,4,5-tetramethyl-1,2,3,6-tetrahydrophthallic anhydride (3.6 g, 0.017 mole), 0.27 g (0.0085 mole) of sulfur and 20 ml of dichlorobenzene was heated to reflux for about 72 hours. The product was freed of dichlorobenzene by rotoevaporation; the gel chromatography of the residue revealed a peak maximum which coincided with the starting material.

EXAMPLE A21

Reaction Product of Diisobutenyl Sulfide and Maleic Anhydride

A half mole (144 g) of diisobutenyl disulfide (prepared via addition of $S_2Cl_2$ to 2,4,4-trimethyl-2-pentene) and a mole (98 g) of maleic anhydride were combined and heated gradually to about 170° C. and maintained at this temperature (with stirring) for 3 hours. The clear, orangecolored reaction mixture turned pitch black during heating, and solids began to deposit on the walls of the reactor. Only part (ca 115 g) of the hot reaction mixture could be decanted. The black, resinous-like mass adhering to the reactor weighed ca 127 g. Vacuum distillation of the decanted reaction mixture afforded about 14 g of product, b.p. 115–120 (0.5 mm). The IR spectrum of the distillate featured characteristic carbonyl absorption bands for an anhydride product and analyzed for 18.15% sulfur.

The following examples relate to the bridging of Diels-Alder adducts with $SCl_2$ and $S_2Cl_2$ and the conversion of the $S_xCl_2$-olefin diacid anhydride to the corresponding thio-bis-(lactone acid).

EXAMPLE A22

Two tenths (30.4 g) mole of cis-1,2,3,6-tetrahydrophthalic anhydride (cis-4-cyclohexene-1,2-dicarboxylic anhydride) was dissolved in chloroform (200 ml) and 0.1 mole (10.3 g) of $SCl_2$ were added dropwise to the well stirred solution at room temperature. The $SCl_2$ addition increased the temperature to 53° C. and the addition was completed at about 53° C. Midway during $SCl_2$ addition the solution turned hazy and some solids separated from solution. After addition the mixture was allowed to cool and the solids (20 g) were isolated by filtration. The solid product featured an IR spectrum with strong anhydride carbonyl absorption, melted at 177°–178° C., and analyzed for 46.88% C, 4.22% H, 7.68% S, and 14.93% Cl. Theory for the adduct ($C_{16}H_{16}Cl_2O_6S$) requires 47.18% C, 3.96% H, 7.87% S, and 17.41% Cl.

About 10.2 g (0.025 mole) of the adduct of cis 1,2,3,6-tetrahydrophthalic anhydride and $SCl_2$ were dissolved in 100 ml of THF and mixed with 1 g of water and two drops of concentrated sulfuric acid. The mixture was refluxed in THF for four hours, then the THF was distilled off and replaced by p-dioxane. The dioxane solution was refluxed for about 24 hours. The dioxane was stripped and the residue was dissolved in a mixture of methylene chloride and ether. A white solid separated. The solid featured an infrared spectrum consistent with the desired lactoneacid product.

EXAMPLE A23

A mole (152 g) of cis-1,2,3,6-tetrahydrophthalic anhydride (cis-4 cyclohexane-1,2-dicarboxylic anhydride) was dissolved in 400 ml of chloroform and 0.50 mole (68 g) of sulfur monochloride were added dropwise to the well stired solution at room temperature. Initially the $S_2Cl_2$ addition did not produce an exothermic reaction, but the reaction temperature rose to about 33° C. by the end of the addition, the solution was allowed to stir at room temperature for 8 hours, some solid separated during this period. The solid was filtered and yielded 166 g of a white crystalline material which melted at 154°–156° C. and analyzed for 44.03 wt. % C, 4.12 wt. % H, 14.75 wt. % S and 15.43 % Cl. The solid product featured an IR with strong anhydride carbonyl absorption. The filtrate was evaporated obtaining an oily residue with an infrared analysis and GPC similar to the solid product.

EXAMPLE A24

About 11.0 g (0.025 mole) of the adduct of cis 1,2,3,6-tetrahydrophthalic anhydride and $S_2Cl_2$ were dissolved in 100 ml of THF and mixed with 1 g of water and two drops of concentrated sulfuric acid. The mixture was refluxed in THF for four hours, then the THF was distilled off and replaced by p-dioxane. The dioxane solution was refluxed for about 24 hours. The dioxane was stripped and the residue was dissolved in a mixture of methylene chloride and ether. A white solid separated. The solid featured an infrared spectrum consistent with the desired lactone acid product.

EXAMPLE A25

Sulfenylation of Cl-Dibsa with $SCl_2$

Approximately 2.08 g (ca 0.01 mole) of 3,3,4,5-tetramethyl-1,2,3,6-tetrahydrophthallic anhydride were dissolved in 50 ml of anhydrous ether and stirred at room temperature under a nitrogen blanket. Then, 0.5 g (ca 0.005 mole) of $SCl_2$ were added dropwise. No HCl evolution was observed. The reaction mixture was stirred at room temperature overnight and then added dropwise into a large volume of pentane. It yielding 1.2 g of a white solid which showed to be the sulfur-bridged product of the nitrogen, producing 1.4 g of an oily substance. The GPC of the oily material showed mainly sulfur-bridged anhydride product.

In the ensuing examples, the bridging of n-octenyl-succinic anhydride (NOSA), diacid, hemiester and silica gel-bound NOSA with such sulfenylating agents as $SCl_2$, $S_2Cl_2$, $Se_2Cl_2$, 1,2-ethane-bis-sulfenyl chloride, 1,3,4-thiadiazole-2,5-bis-sulfenyl chloride, and a novel alkyl sulfenate ester-HCl combination reagent using various experimental conditions, are elaborated.

Methods for converting the $S_xCl_2$—NOSA adducts to thio-bis (lactone acids and esters) are also described.

EXAMPLE A26

Adduct of $SCl_2$ and n-Octenylsuccinic Anhydride

Three moles (630 g) of n-octenylsuccinic anhydride (NOSA) were diluted in a liter of $CH_2Cl_2$ and stirred at room temperature. Then 1.5 moles (154 g) of $SCl_2$ in 500 ml of $CH_2Cl_2$ were added dropwise. The exothermic reaction peaked to 50° C. initially and external cooling was applied to maintain reaction temperature at about 25° C. No HCl evolution occured. After stirring the reaction mixture for an hour after the SCl₂ addition, the solvent was removed by evaporation with a mild stream of nitrogen. The solid that separated from solution during solvent evaporation was isolated (40 g) and after being recrystallized from CH₂Cl₂, melted at 149°–150° C. and analyzed for 55.45% C, 7.17% H, 5.73% S and 11.4% Cl. The adduct, C₂₄H₂₆O₆SCl₂, requires 55.06% C, 6.93% H, 6.13% S, and 13.55% Cl. The infrared spectrum featured an intense anhydride absorption at 5.67 microns, and a proton spectrum consistent with the structure shown below.

The concentrate obtained from the supernatant weighed 745 g and featured an IR spectrum similar to that shown for the solid. The yield of anhydride-SCl₂ adduct was virtually quantitative. A structure for one of the dominant bridged isomers formed in the SCl₂-anhydride reaction is depicted below:

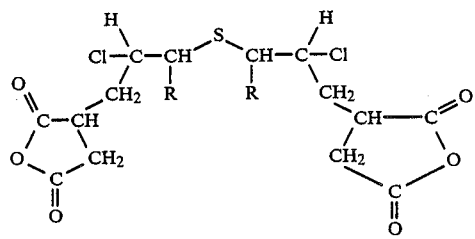

R = C₅H₁₁ (n-pentyl)

EXAMPLE A27

S₂Cl₂-n-Octenylsuccinic Anhydride (NOSA) Adduct

A mole (210 g) of n-octenylsuccinic anhydride was dissolved in a liter of ether and a half mole (67.5 g) of sulfur monochloride (S₂Cl₂) was added dropwise to the stirred solution at room temperature. An exothermic reaction occured and the addition was completed under refluxing conditions. The reaction mixture was stirred overnight and then concentrated by rotoevaporation at 500° C. for 2 hours. The product featured an IR spectrum with a prominent anhydride carbonyl band at 5.65 microns, and analyzed for 49.33% C, 6.04% H, 10.7% S and 12.6% Cl. Theory for the S₂Cl₂-n-octenylsuccinic anhydride adduct (C₂₄H₃₆Cl₂O₆S₂) requires 51.88% C, 6.53% H, 11.54% S, and 12.76% Cl.

EXAMPLE A28

6,6'-Thio-Bis-(3,5-Carbolactone-Undecanoic Acid)

228 g (1.0 mole) of n-octenyl succinic acid, prepared via the hydrolysis of NOSA at 80° C., were dissolved in 200 ml of tetrahydrofuran (THF) and stirred at room temperature while 52 g (0.5 mole) of SCl₂ were added dropwise. The reaction was exothermic and HCl evolution was observed during and after the addition which took about one hour. When the addition was completed, the reaction mixture was allowed to stir at room temperature overnight; a white solid formed upon standing. The solid was filtered, collected and dried (43 g). The infrared analysis of the white powder showed it to be desired thio-bis-(lactone acid) which analyzed for 59.81% C, 7.68% H, 26.42% O, and 6.52% S (theory requires: 59.23% C, 7.87% H, 26.30% O and 6.59% S). The filtered reaction mixture was then refluxed in THF for a few hours to effect complete reaction. Further work-up of the reaction mixture afforded more white solids amounting to a quantitative yield of product. In accord with expectations, GPC analysis featured a single band with a peak maximum of $M_n$ 480; and mass spectral analysis revealed a molecular ion at m/z 486, in harmony with the proposed structure shown below:

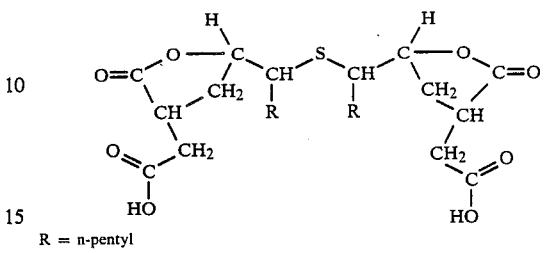

R = n-pentyl

EXAMPLE A29

Adduct of 1,2-Ethane-Bis-Sulfenyl Chloride and N-Octenylsuccinic Anhydride

A tenth mole (21.0 g) of n-octenylsuccinic anhydride dissolved in 100 ml of methylene chloride was bridged with 0.05 mole (8.2 g) of 1,2-ethane-bis-sulfenyl chloride via the dropwise addition of the latter to the anyhride at 0° C. over a 15-minute period. The reaction mixture was stirred overnight and rotoevaporated. The IR spectrum of the concentrate featured a strong anhydride carbonyl absorption band at 5.65 microns. The gel permeation chromatogram of the product featured a single peak corresponding to the bridged adduct.

Treatment of the adduct product with a tenth mole of water at 70° C. for an hour afforded the corresponding lactone acid, 6,11-dipentyl-3,5,14,12-bis-carbolactone-7,10-dithiahexadecane-1,16-dioic acid in quantitative yield. The IR spectrum of the lactone product featured strong lactone and carboxylic acid carbonyl absorption bands at 5.68 and 5.88 microns.

EXAMPLE A30

Adduct of Selenium (I) Chloride and Nosa

Three tenths mole (63.0 g) of NOSA were dissolved in 100 ml of CHCl₃ and 34.5 (0.15 mole) of selenium (I) chloride were added dropwise at room temperature. The reactor mixture was stirred at room temperature for 24 hours. The CHCl₃ solution was rotoevaporated until constant weight and the residue showed by GPC a maximum peak corresponding to the bridged product.

EXAMPLE A31

Dimethyl 6,6'-Thio-Bis-(3,5-Carbolactone-Undecanoate)

A half-mole of the adduct of SCl₂ and n-ocetylsuccinic anhydride was added to 500 ml of xylene containing 32 g of methanol. The mixture was allowed to stir overnight and heated to reflux for about four hours. The product was then rotoevaporated for three hours at 70°–80° C. The final produced featured an IR spectrum with intense lactone and ester carbonyl absorption at 5.63 and 5.78 microns, and analyzed for 60.48% carbon, 8.30% hydrogen, and 6.48% sulfur. The thio-bis-lactone ester (C₂₆H₄₂O₈S) requires 60.67% C, 8.23% H and 6.23% S.

The same ester lactone was easily prepared via the addition of SCl₂ to the mono-methyl ester of n-octenyl succinic acid.

EXAMPLE A32

Dimethyl
6,6'-Dithio-Bis-(3,5Carbolactone-Undecanoate)

Four-tenths mole of the adduct of $S_2Cl_2$ and n-octenylsuccinic anhydride and 0.8 mole (25.6 g) of methanol were dissovled in 200 ml of chloroform and stirred at room temperature for four days, refluxed in 16 hours, and rotoevaporated at 80° C. for three hours. The product showed an IR spectrum with intense lactone and ester carbonyl bands and analyzed for 57.19% carbon, 7.93% hydrogen, and 10.54% sulfur. Theory for the methyl ester product ($C_{26}H_{42}O_8S_2$) requires 57.11% carbon, 7.74% hydrogen and 11.73% sulfur.

The same lactone ester could be readily prepared via the addition of $S_2Cl_2$ to the monomethyl ester of n-octenylsuccinic acid.

EXAMPLE A33

6,6'-Dithio-Bis-(3,5-Carbolactone-Undecanoic Acid)

A half-mole (114 g) of n-octenylsuccinic acid (prepared via hydrolysis of n-octenylsuccinic anhydride at 80°) in 500 ml of chloroform was treated dropwise with a quarter mole (37.8 g) of sulfur monochloride ($S_2Cl_2$) at room temperature. The mixture was then reluxed for several hours (strong HCl evolution). The mixture was then refluxed for several hours (strong HCl evolution). Infrared analysis of the reaction mixture showed the presence of the desired lactone acid. The corresponding monothio product can be prepared in the above-described manner with $SCl_2$.

EXAMPLE A34

Thio-Bis-(Lactone Acid) via Addition of $SCl_2$ to Silica Gel-Bound N-Octenysuccinic Anhydride About 42 g (0.2 mole) of NOSA were dissolved in 200 ml of n-octane admixed with about 200 g of silica gel. An infrared spectrum of the octane layer showed that all of the NOSA had been adsorbed to the silica gel. Then, 10.3 g (0.1 mole) of $SCl_2$ were added dropwise to the slurry, and an exothermic reaction took place. The mixture was stirred at room temperature for 2 hours and 3.6 g (0.2 mole) of water were added. The well-stirred mixture was refluxed in octane for about 8 hours. The n-octane was decanted and the silica gel was extracted three times with 200 ml aliquots of THF (tetrahydrofuran). The THF was evaporated and a semisolid product was obtained. The infrared and MS spectral data fully confirmed that the product was the desired 6,6'-thio-bis-(3,5 carbolactone-1-undecanoic acid).

EXAMPLE A35

Thio-Bis-(Lactone Ester) via the HCl-Induced Reaction of Diisopropoxy Disulfide with NOSA About 42 g (0.2 mole) of NOSA were dissolved in 100 ml of THF and stirred at room temperature under a nitrogen blanket, while 18.2 g (ca 0.1 mole) of diisopropoxy disulfide were added. Then, hydrogen chloride gas was slowly bubbled into the stirred solution at room temperature for about 3 minutes. An exothermic reaction took place upon the addition of gaseous HCl. The reaction mixture was stirred at room temperature for a few minutes and then refluxed in THF with one drop of concentrated sulfuric acid for about 8 hours. The THF was stripped and an oily residue was obtained. The residue featured an infrared spectrum characteristic of the sulfur bridge lactone ester. GPC analysis indicated complete bridging.

EXAMPLE A36

Bridging of NOSA via Sulfenylation with 1,3,4Thiadiazole-2,5-Bis-Sulfenyl Chloride Two-tenth mole (42 g) of n-octenyl succinic anhydride (NOSA) were dissolved in 100 ml of $CHCl_3$ and 0.1 mole (21.9 g) of 1,3,4-thiadiazole 2,5-bis-sulfenyl chloride in 100 ml of chloroform were added dropwise for a period of 15 minutes. An external cooling bath was provided to keep the addition at room temperature. The reaction mixture was then stirred at about 25° C. overnight. The solution was filtered and the filtrate was concentrated with a stream of nitrogen. The oily residue featured an infrared spectrum with strong anhydride carbonyl absorption band at 5.65 microns. GPC analysis revealed that complete bridging had been achieved. Spectral analyses were in full accord with the desired thio-bis-(acylating agent).

In the examples that follow, the surfur bridging of tetrapropenylsuccinic anhydride (TPSA) and octadecenylsuccinic anhydride (OSA) and its diacid analog, with $SCl_2$ and $S_2Cl_2$ using various temperatures and solvents, will be described.

EXAMPLES A37

Adduct of $S_2Cl_2$ and Tetrapropenylsuccinic Anhydride

A mole (266.4 g) of tetrapropenylsuccinic anhydride dassolved in 300 ml of $CH_2Cl_2$ and a half mole (68 g) of sulfur monochloride in 200 ml of $CH_2Cl_2$ were added dropwise and simultaneously into a reactor containing 500 ml of $CH_2Cl$ at about 25° C. and then the reaction mixture was stirred overnight. Removal of solvent by evaporation gave a concentrate containing 4.73% chlorine and featuring an infrared spectrum with an intense anhydride carbonyl absorption band at 5.65 microns. Rotoevaporation of the concentrate at 100° C. for 4 hours gave an adduct which analyzed for 3.19% chlorine and gave a gel permeation chromatogram characterized by a dominant band for the sulfur-bridged anhydride product.

EXAMPLE A38

Dehydrochlorinated Adduct of $SCl_2$ and N-Octadecenyl Succinic Anhydride (OSA)

Two hundred grams (0.57 mole) of n-octadecenylsuccinic anhydride were dissolved in 150 ml of chloroform. The resulting solution was stirred at room temperature and then bridged via the dropwise addition of 29.4 g (0.286 mole) of sulfur dichloride. The bridging event was sufficiently exothermic to reflux the chloroform diluent. Evolution of HCl gas was noted during the $SCl_2$ addition. Refluxing was continued for several hours after addition by applying external heating to the reactant. Rotoevaporation of the mixture for 2 hours at 100° C. afforded the S-bridged anhydride adduct. Gel permeation chromatography revealed that coupling with $SCl_2$ was virtually complete. The S-coupled anhydride adduct featured an intense carbonyl absorption band at 5.68 microns and analyzed for 4.65% sulfur and 3.88% chlorine. The chlorine analysis indicates that the adduct had undergone extensive dehydrochlorination.

EXAMPLE A39

Adduct of $S_2Cl_2$ and Octadecenylsuccinic Anhydride

Two hundred grams (0.57 mole) of n-octadecenyl succinic anhydride dissolved in 150 ml of chloroform was bridged via the dropwise addition of 38.6 g (0.286 mole) of sulfur monochloride ($S_2Cl_2$) at room temperature. The bridging reaction caused a gradual exotherm (solvent began refluxing) accompanied by the evolution of HCl. Rotoevaporation at 100° C. for several hours gave a concentrate which featured a gel permeation chromatogram consistent with the expected sulfur-bridged anhydride adduct product. The adduct analyzed for 6.99% sulfur, and 5.29% chlorine, and featured an IR spectrum dominated by an anhydride carbonyl absorption band at 5.67 microns.

The chlorine analysis is consistent with a mixture comprising the dichlorosulfide, mono-chlorosulfide and unsaturated sulfide products.

EXAMPLE A40

6,6'-Thio-Bis-(3,5-Carbolactone-Heneicosanoic Acid)

Two-tenths mole (73.6 g) of octadecenylsuccinic acid was dissolved in 500 ml ether and a tenth mole (10.3 g) of $SCl_2$ was added dropwise to the stirred ether solution at about 25° C. The addition was exothermic (ether refluxed) and HCl evolution occurred. The mixture was refluxed for about 8 hours. Upon cooling solids separated from solution. The solid product featured an infrared spectrum with prominent lactone and carboxylic acid carbonyl absorptions at 5.62 and 5.82 microns, melted at 158°–163°, and analyzed for 69.01% C, 10.17% H, 4.37% S and 16.74% O. Gel permeation chromatography revealed that coupling of the diacid with $SCl_2$ was virtually complete to the lactone acid structure. Theory for the thio-bridged lactone acid ($C_{44}H_{78}O_8S$) requires 68.88% C, 10.25% H, 4.18% S and 16.69% O.

Further refluxing the supernatent gave four more crops of product with a combined weight of 50 g. The yields were quantitative. The proposed structure for the title thio-bis-(lactone alkanoic acid) is illustrated below:

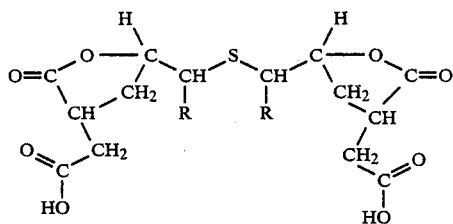

wherein R is $n-C_{15}H_{31}$.

EXAMPLE A41

6,6'-Dithio-Bis-(3,5-Carbolactone-1-Heneicosanoic Acid)

Two-hundred grams (0.54 mole) of n-octadecenyl succinic acid were dissolved in a liter of $CHCl_3$ and 36.7 g (0.272 mole) of sulfur monochloride ($S_2Cl_2$) were added dropwise to the stirred solution at room temperature. The exothermic process was accompanied by virgorous HCl evolution. After refluxing the mixture for about 8 hours, the solution was cooled and solids separated. Filtration gave 19 g of solid (m.p. 131°–136° C.) which featured an IR spectrum with intense carbonyl bands at 5.62 and 5.72 microns, and analyzed for 66.42% C, 9.63% H, and 8.22% S. Theory for the adduct ($C_{44}H_{78}O_8S_2$) requires 66.12% C, 9.84% H, and 80.2% S. Rotoevaporation of the supernatant gave a solid product in high yield.

In the following examples, the preparation of anhydride derivatives of thio-bis-(lactone acids) is described.

EXAMPLE A42

6,6'-Thio-Bis-(3,5-Carbolactone-Undecanoic Acid) Anhydride

About 12.3 g (ca 0.025 mole) of Example A28 were slurried in 100 ml of methylene chloride at room temperature and 5.2 g (ca. 0.025 mole) of N,N'-dicyclohexylcarbodiimide (DCD) were added. The DCD addition produced an exothermic reaction and a clear solution. Shortly thereafter, a white solid separated from solution. The reaction mixture was stirred at room temperature for half hour to assure complete conversion. The solid was filtered and collected. It showed to be dicyclohexyl urea. The filtrate was blown down with nitrogen to an oily residue ester. A quantitative yield of cyclic anhydride was obtained. The infrared spectrum of the solid showed strong absorption bands characteristic of lactone anhydride products. It analyzes for 60.21 Wt. % C, 7.69 Wt. % H and 6.78 Wt. % S. Theory requires 61.51 Wt. % C, 7.74 Wt. % H and 6.84 Wt. % S. GPC analysis of the macrocyclic anhydride revealed a peak maximum at Mn of 344; mass spectral analysis using chemical ionization shows a parent ion (protonated) at m/z=469.

EXAMPLE A43

6,6-Dithio-Bis-(3,5-Carbolactone-Undecanoic Acid) Anhydride

About 12.7 g (ca 0.025 mole) of lactone acid obtained via hydrolysis of Example A27 were slurried in approximately 100 ml of methylene dichloride and mixed with 5.2 g (0.025 mole) of dicyclohexyl carbodiimide (DCD) and stirred at room temperature for about an hour. The dicyclohexyl urea by-product was separated by filtration and the filtrate was evaporated with a mild stream of nitrogen. The oily reisdue was dissolved in methylene chloride ether and a white solid slowly formed upon standing. The infrared and elemental analyses of the solid corresponded to the desired cyclic lactone anhydride product.

In the same manner, 143 g (ca. 0.185 mole) of Example 40 were treated with 38.1 g (ca. 0.185 mole) of DCD in 500 ml of methylene dichloride. After separation of the dicyclohexyl urea by-product, the filtrate upon work-up, afforded a high yield of 6,6'-thio-bis-(3,5carbolactone-heneicosanoic acid anhydride).

B. SYNTHESIS OF MACRO THIO-BIS-(ACYLATING AGENTS)

The following Examples describe the sulfenylation of polyisobutenyl succinic acids and anhydrides with $SCl_2$ and $S_2Cl_2$ to give thio-bis-(acylating agents), including thio-bis-(lactone acid/ester) and thio-bis-(alkene diacid anhydride) reagents.

Several examples also teach the use of solid phase synthesis wherein silica gel-bound PIBSA is successively (a) bridged via sulfenylation with sulfur halide and (b) lactonized to afford the thio-bis-(lactone acid) product.

EXAMPLE B1

Thio-Bis-(Polyisobytyl Lactone Acid)

Approximately 130 g of polyisobutenyl succinic acid, $M_n776$, prepared via hydrolysis of PIBSA having a Sap. No. of ca 84 were dissolved in 400 ml of chloroform and 0.05 mole (5.3 g) of $SCl_2$ was added dropwise to the stirred solution. After refluxing the mixture overnight, two drops of sulfuric acid were added, the solvent was stripped off, and the mixture heated at about 100° C. overnight. The product featured an infrared spectrum with strong carbonyl absorption bands in the 5.6–5.8 micron region and analyzed for 1.69% sulfur and 0.09% chlorine. The IR spectrum of the diethylamine-treated product revealed a strong lactone carbonyl band at 5.63 microns.

EXAMPLES B2

Thio-Bis-(Polyisobutyl Lactone Acid)

Ca. 0.1 mole (130 g) of PIBSA ($M_n$) of 776 having a Sap. No. of ca. 84 was dissolved in 100 ml of dioxane and 0.05 mole (5.3 g) of $SCl_2$ was added dropwise to the well-stirred solution at ca. 25° C. The mixture was then refluxed for four hours (HCl evolution noted). At this point, 4 g of water acidified with three drops of concentrated sulfuric acid were added and the mixture was further refluxed for 24 hours. The mixture was filtered through basic Celite and rotoevaporated at 90° C. for several hours. The concentrate featured an IR spectrum with strong absorption bands in the 5.6–5.8 micron region, and analyzed for 1.55% sulfur and 0.09% chlorine.

EXAMPLE B3

Dithio-Bis-(Polyisobutyl Lactone Acid)

Five hundred grams (0.385 moles) of PIBSA having an ($M_n$) of 775 and a Sap. No. of 84 were dissolved in 60 ml of methylene chloride and cooled to 0° C. While stirring at 0° C. under a nitrogen blanket, 26 g (0.192 moles) of sulfur monochloride were added dropwise over a period of half hour. The reaction mixture was allowed to warm up to room temperature and stirred for about ten hours.

One-half of this product was diluted in 100 ml of p-dioxane and 6.9 g of water (ca. 0.38 moles) were slowly added. The reaction mixture was refluxed for ten hours in the presence of a catalytic amount of sulfuric acid (HCl evolution occurred during reflux). Thereafter, the solvent was removed by rotoevaporation and the mixture further heated to 130°–140° C. for one hour. The product featured an infrared spectrum with strong absorption bands in the 5.6–5.8 micron region (lactone acid) and analyzed for 2.43 Wt. % sulfur and 0.05 Wt. % Cl. The IR spectrum of the diethylamine treated product revealed a strong lactone carbonyl band at 5.63 microns.

EXAMPLE B4

Dithio-Bis-(Polyisobutenylsuccinic Anhydride)

About 200 g (ca 0.154 moles) of PIBSA having a $M_n$ of 1080 and a Sap. No. of 72 were dissolved in 100 ml of methylene chloride. While stirring at room temperature under a nitrogen blanket, 10.4 g (0.077 moles) of sulfur monochloride were added dropwise for a period of 15 minutes. The reaction mixture was allowed to stir at room temperature overnight.

One-half of the above adduct was heated to 150° C. for approximately 4 hours. Analytical data on the dehydrohalogenated residue showed 2.08 Wt. % sulfur and 0.15 Wt. % chlorine.

EXAMPLE B5

Approximately 100 g of the adduct described in the first paragraph of Example B4 were dissolved in 50 ml of THF and 3 g of water and two drops of sulfuric acid. The reaction mixture was refluxed in THF for about four hours and then heated to 120° C. for ten hours after the THF distill off. The product featured an infrared spectrum with strong carbonyl absorption bands in the 5.6–5.8 microns region which are characteristic of the lactone acid products. It analyzed for 2.08 Wt. % S.

Approximately 30 g (ca. 0.01 mole) of the dithio-bis-(polyisobutyl lactone acid) were dissolved in 30 g of mineral oil solvent 150 neutral and heated to 150° C. Then, 2.2 g (ca. 0.01 mole) of PAM were added dropwise and the reaction mixture was nitrogen sparged for two hours. The filtered product showed an infrared spectrum characteristic of the dithio-bis (polyisobutyl lactone imide). It analyzed for 1.28 Wt. % N.

EXAMPLE B6

Adduct of $SCl_2$ and Silica Gel Extracted PIBSA

About 600 g of dilute ene PIBSA having a saponification number of 66 were dissolved in 6.3 liters of pentane. The solution was mixed with 1800 g of silica gel and stirred at room temperature for about 12 hours. The pentane layer was decanted and the silica gel was washed twice with one liter aliquots of pentane.

The PIBSA bound silica gel was subsequently extracted with two liters of boiling THF. Rotoevaporation at 80° C. for two hours afforded 542 g of a polyisobutylene free PIBSA residue which featured a saponification number of 92.9, and a Mn of 1090 by vapor phase osmometry.

About 145 g (ca. 0.145 mole) of a PIBSA prepared as described above and showing a saponification number of 92.9, were dissolved in 200 ml of THF and stirred at room temperature under a nitrogen blanket. Then 7.5 g (ca. 0.073 mole) of a freshly distilled $SCl_2$ were added dropwise for a period of ten minutes. The reaction mixture was stirred at room temperature for 12 hours. The THF was distilled off and the residue was refluxed in p-dioxane for 12 hours. Rotoevaporation of the p-dioxane solvent gave a residue which featured an IR spectrum with a strong anhydride carbonyl absorption band at 5.65 microns, a gel permeation chromatogram having a maximum peak at 1323. The analytical data showed 1.53 Wt. % S and 0.66 Wt. % Cl.

EXAMPLE B7

Thio-Bis-(Polyisobutyl Lactone Acid) Via Sulfenylation of Silica Gel-Bound PIBSA with $SCl_2$ About 300 g of ene PIBSA described in Example B6 were dissolved in 300 ml of THF and stirred at room temperature under a nitrogen blanket. Then 15.45 g (0.15 mole) of freshly distilled $SCl_2$ were added dropwise for a period of ten minutes. The reaction mixture was stirred at room temperature for 12 hours. Thereafter 7.2 g (ca. 0.4 mole) of water were added and the reaction mixture was refluxed in THF. Then, 50 g of Amberlyst were added and the reaction mixture was heated to 120° C. for four hours. Rotoevaporation of the mixture under high vacuum at 100° C. for four hours gave a residue which featured an infrared spectrum consistent with the desired thio-bis-lactone acid product. The residue analyzed for 1.53 Wt. % S.

EXAMPLE B8

Bridging of Silica Gel-Bound Cl-PIBSA with $SCl_2$

About 100 g of Diels-Alder PIBSA having a $M_n$ of 751 and a saponification number of 80 were dissolved in 500 ml of pentane and mixed with 300 g of silica gel. The mixture was stirred at room temperature for about 12 hours and the pentane phase was decanted. The silica gel was washed twice with 500 ml of pentane and the pentane fraction was evaporated. About 54 g of PIBSA were left on the silica gel. Then, 500 ml of heptane were added and the mixture was well stirred while 3.3 g (ca. 0.027 mole), (85% purity) of sulfur dichloride were added dropwise. The mixture was stirred at room temperature for one hour. A gel chromatogram of sulfur-bridged PIBSA sample desorbed from silica gel with THF featured a maximum peak at $M_n$ 606. The GPC of the starting PIBSA exhibited a maximum peak at 465. The reaction mixture containing 2 grams of water, was then refluxed in heptane for 12 hours. Thereafter, the heptane was decanted and the silica gel was extracted with 500 ml of THF twice, giving 22 g of partially lactonized bridged product which featured a GPC with a maximum peak at $M_n$ 550. The silica gel was then extracted twice more with 500 ml of hot THF to yield 15 g of a lactone acid product which featured a gel chromatogram with maximum peak at $M_n$ 580.

EXAMPLE B9

Thio-Bis-(Polyisobutenylsuccinic Anhydride)

Approximately 200 g (ca. 0.154 moles) of PIBSA ($M_n$ of 776 having a Saponification No. of 84) were charged into a 500 ml reaction flask and dissolved in 100 ml of p-dioxane. While stirring at room temperature under nitrogen blanket, 7.9 g (ca. 0.077 mole) of $SCl_2$ were added dropwise for about ten minutes. An exothermic reaction was observed during the addition. Then, the reaction mixture was refluxed in p-dioxane for four hours until the HCl evolution ceased. The solvent was rotoevaporated under high vacuum at 100° C. until constant weight. It analyzed for 1.92 Wt. % S and 0.62 Wt. % Cl.

EXAMPLE B10

Dithio-Bis-(Polyisobutenylsuccinic Anhydride)

About 676 g (ca. 0.71 moles) of a PIBSA (prepared via the reaction of chloro polyisobutylene and maleic anhydride), having a $M_n$ of 771 and a Saponification No. of 118 were dissolved in one liter of $CH_2Cl_2$. The solution was stirred at room temperature while 49 g (ca. 0.36 mole) of $S_2Cl_2$ were added dropwise for a period of one hour. The reaction mixture was stirred at room temperature for about 12 hours. The solvent was nitrogen sparged and the residue was rotoevaporated under high vacuum at 100° C. for four hours. The dithio-bis-(alkenyl succinic anhydride) analyzed for 2.71 Wt. % S and 1.00 Wt. % Cl.

C. AMIDATION OF MODEL THIO-BIS-ACYLATING REAGENTS

In the ensuing examples, synthetic procedures are outlined for the amidation of model thio-bis-(lactone acid and ester) reactants and sulfur halide-olefin diacid adducts via primary and secondary monoamines to give amic acid, amic acid salt, and bis-amide products. The use of carbodiimide as a promoter in achieving more facile amidations is also illustrated. Finally, the formation of macrocyclic imides in the amidation of thio-bis-(lactone acid) reagents with certain primary amines is also described.

EXAMPLE C1

Amic Acid Formation: N-t-Butyl 6,6'-Thio-Bis-(3,5-Carbolactone-Undecanoic Acid) Mono-Amide About 12.3 g (ca. 0.025 mole) of 6,6'-thio-bis-(3,5-carbolactone-undecanoic acid) were dissolved in 100 ml of methylene dichloride and stirred at room temperature. Thereafter, 10.3 g (ca. 0.05 mole) of N,N'-dicyclohexylcarbodiimide were added and the reaction mixture was allowed to stir at room temperature for ten minutes while N,N'-dicyclohexylurea precipitated from solution. Infrared analysis of the filtered reaction mixture revealed that the lactone acid had been completely converted to the desired macrocyclic anhydride. At this point, 1.83 g (ca. 0.025 mole) of t-butylamine were added and the reaction mixture was refluxed in methylene chloride solution for 2 hours. Rotoevaporation of the filtered reaction mixture gave a residue which featured an infrared spectrum with characteristic absorption bands for a lactone amic acid product.

EXAMPLE C2

Amic Acid Amine Salt Formation: N-Di-Octadecyl 6,6'-Dithio-Bis-(3,5-Carbolactone-Heneicosanoic Acid) Mono-Amide Di-Octadecylamine Salt About 11 g (ca. 0.014 mole) of 6,6'-dithio-bis(3,5-carbolactone-heneicosanoic acid) (Example A41) were dissolved in 100 ml of xylene and combined with 14.6 g (ca. 0.028) mole of $C_{18}H_{37})_2NH$ (95%) purchased as Armeen 2HT from Armak Corp. of Chicago, Ill. The mixture was heated to reflux and the water of reaction was collected in a Dean-Stark trap. After refluxing for six hours at 140° C., the reaction mixture was cooled to room temperature. The white solid that precipitated out of solution was islolated by filtration (20 g).

The infrared spectrum of the solid featured absorption bands ascribable to the title amic acid amine salt and analyzed for 77.20% C, 12.46% H and 1.89% N. Theory requires 76.32% C, 12.50% H and 1.55% N. The gel permeation chromatogram of the product featured a peak maximum at Mn 1347.

The clear filtrate obtained in the above work-up procedure was cooled, and a second solid separated from solution. Filtration of the mixture gave 5.2 g of a white solid (Mn=1151 by GPC) which featured an infrared spectrum consistent with the free amic acid.

EXAMPLE C3

Bis-Amide Formation: N,N'-Bis-Di-Octadecyl 6,6'-Dithio-Bis-(3,5-Carbolactone-Heneicosanamide)

Approximately 9 g (ca. 0.0113 mole) of Example A41 were dissolved in 100 ml of xylene and mixed with about 11.7 g (ca. 0.0225 mole) of $(C_{18}H_{37})_2NH$ (Armeen 2HT purchased from Armak Corp., Chicago, Ill.). The reagents were heated in boiling xylene for one hour, and then the xylene was distilled off. The residue was heated to 200°-240° C. for one hour to maximize bis-amide formation. A solid product was obtained, which recrystallized from acetone-xylene as a fine, white powder.

The recrystallizate featured an infrared spectrum with prominent lactone and amide absorption bands at 5.68 and 6.10 microns, and analyzed for 78.38% C, 12.49% H and 1.59% N. Theory for the title compound requires 77.16% C, 12.42% H and 1.55% N. The recrystallized product featured a gel permeation chromatogram with a single peak having a maximum at Mn 1555.

EXAMPLE C4

6,6'-Thio-Bis-(3,5-Carbolactone-Undecanamide)

About 1.23 g (ca. 0.0025 mole) of Example 42 were dissolved in 50 ml of methylene dichloride and stirred at room temperature while ammonia was bubbled into the solution for about five minutes. Then, 0.52 g (0.0025 mole) of dicyclohexyl carbodiimide were added, and the reaction mixture was heated to reflux in methylene dichloride for ten minutes. The reaction mixture was filtered hot to remove the dicyclohexyl-urea by-product. The filtrate yielded a crystalline white solid upon cooling. The infrared spectrum of the solid showed strong absorption bands for the title thio-bis-(lactone amide). The product analyzed for 59.37 Wt. % C, 8.32 Wt. % H and 5.73 Wt. % N. Theory requires 59.48 Wt. % C, 8.32 Wt. % H and 5.78 Wt. % N. The mass spectrum of the bis-amide featured a parent ion at $M/z=484$.

EXAMPLE C5

5,5'-Thio-Bis-(3,5-Carbolactone-Undecananilide)

About 24.3 g (ca. 0.05 mole) of 6,6'-thio-bis(3,5 -carbolactone-undecanoic acid) were dissolved in 100 ml of xylene and stirred at room temperature under a nitrogen blanket. Then, 9.3 g (0.10 mole) of aniline were added dropwise for a period of 10 minutes. Upon completion of the addition, the reaction mixture was refluxed in xylene, until water evolution ceased. The xylene solution was heated for a total of 24 hours at 140° C. to ensure complete conversion. While the clear solution was cooling to room temperature a white solid precipitated out. A quantitative yield of solid was obtained. The infrared spectrum of the white solid featured strong carbonyl absorption bands at 5.7 and 6.1 microns, ascribable to lactone and amide functionality. The solid analyzed for 66.86 Wt. % C, 7.48 Wt. % H, 4.40 Wt. % N and 5.32 Wt. % S. Theory requires 67.9 Wt. % C, 7.54 Wt. % H, 4.40 Wt. % N and 5.03 Wt. % S. The mass spectrum of the product showed a parent ion at $m/z=635$.

EXAMPLE C6

N,N'-Bis-[2,2'-Oxydiethyl] 6,6'-Thio-Bis-(3,5-Carbolactone-Undecanamide)

A tenth mole (51.3 g) of the adduct of $SCl_2$ and n-octenyl succinic anhydride was dissolved in 100 ml of xylene, and 0.2 mole (6.4 g) of methyl alcohol was added to the well-stirred solution. The reaction mixture was refluxed for four hours. Evolution of HCl gas was observed. The infrared spectrum of the xylene solution featured strong absorption bonds for the desired lactone-ester. Them, 0.2 mole (17.4 g) of morpholine were added, and the reaction mixture was refluxed in xylene for about 20 hours. Rotoevaporation of the mixture for an hour at 100° C. gave an oil residue which featured an infrared spectrum consistent with the title thio-bis-(alkyl lactone amide). The residue analyzed for 62.44% C, 8.37% H, 4.45% N and 4.60% S. Theory requires 61.50% C, 8.39% H, 4.48% N and 5.10% S.

The title compound of Example C6 can also be prepared via the direct amminolysis of a sulfur chloride-olefin diacid adduct as shown in the following example.

EXAMPLE C7

A tenth mole (ca. 55.6 g) of the adduct of $SCl_2$ and n-octenylsuccinic anhydride was dissolved in 100 ml of toluene and the resulting solution added dropwise to a reaction flask containing 0.4 mole (ca. 34.8 g) of morpholine in 200 ml of toluene. The addition was very exothermic and external cooling bath was used to keep the reaction temperature about 20° C. The reaction mixture was stirred at room temperature and then heated to reflux in toluene for four hours. The reaction mixture was diluted with THF, and the morpholine hydrochloride was removed by filtration. The filtrate was evaporated to give a residue which featured prominent lactone and amide carbonyl absorption bands at 5.62 and 6.10 microns consistent with the proposed lactone amide structure.

EXAMPLE C8

N,N'-Bis-(2,2'-Oxydiethyl) 6,6'-Thio-Bis-(5-Methyl-3,5-Carbolactone-Hexanamide)

A tenth mole (ca. 41.1 g) of the adduct of $SCl_2$ and isobutenylsuccinic anhydride described in Example A1 was dissolved in 100 ml of THF, and then added dropwise (exothermic reaction) to a reactor containing a solution of 0.4 mole (ca. 34.8 g) of morpholine in 200 ml of THF. After addition, the mixture was heated to reflux in THF for about 6 hours and and then filtered to remove the morpholine hydrochloride. The filtrate was dropped into a large excess of pentane and a white solid formed. The solid analyzed for 5.65 Wt. % N and 6.02 Wt. % S. The lactone-amide requires 6.03 Wt. % N and 6.90 Wt. % S. The infrared spectrum of the solid featured prominent lactone and amide carbonyl absorption bands at 5.62 and 6.10 microns, in harmony with the proposed title compound.

EXAMPLE C9

A tenth mole (51.3 g) of adduct described in Example A26 was dissoved in 100 ml of chloroform and 0.2 mole (14.6 g) of diethylamine were added dropwise to the stirred solution at room temperature. The exothermic reaction peaked at about 50° C., and external cooling was applied to maintain reaction temperature at about 10° C. The cooling bath was removed, and the reaction mixture was refluxed for two hours. Evolution of HCl gas occurred. The mixture was rotoevaporated for an hour at 80° C., and the residue diluted with 200 ml of ether. Filtration removed the $Et_2NH.HCl$ by-product. The filtrate was washed with aqueous $Na_2Co_3$ (5% soln.) and dried over $Na_2CO_3$. Rotoevaporation of the ether solution gave a residue which featured an IR spectrum with prominent lactone and amide carbonyl absorption bands at 5.62 and 6.10 microns, and analyzed for 63.73% C, 9.36% H, 4.69% N, and 5.37% S. Theory for the title thio-bis-lactone amide ($C_{32}H_{56}N_2O_6S$) requires 64.39% C, 9.45% H, 4.69% N and 5.37% S.

The ensuring examples illustrate the formation of macrocyclic imide structures via the amidation of thio-bis-(lactone acid) reactants with a mole of primary amine.

EXAMPLE C10

N-Benzyl 2,4,10,8-Dicarbolactone-5,7-Di-n-Pentyl-6-Thia-Undecane-1,11-Di-Carboximide About 24.3 g (ca. 0.05 mole) of 6,6-thio-bis-(3,5-carbolactone-undecanoic acid) were dissolved in 100 ml of xylene and stirred at room temperature under a nitrogen blanket. Then, 5.8 g (ca. 0.05 mole) of benzylamine were added and the reaction mixture was slowly heated to reflux for one hour. About 1.8 ml of water were collected in a Dean-Stark trap during this period. The clear solution was then rotoevaporated under high vacuum at 100° C. until constant weight. The oily residue featured an infrared spectrum with prominent lactone and imide absorption bands at 5.68 and 5.9 microns, respectively. The gel permeation chromatogram of the macrocylic imide showed a single peak at Mn=390 (uncorrected) and featured a mass spectrum with a strong parent ion at m/z 557 in harmony with Structure VIII proposed below.

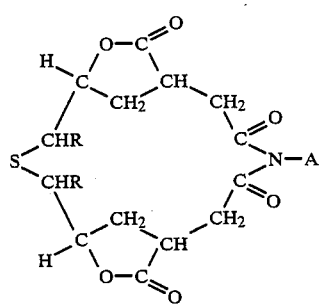

R = n-pentyl
A = Benzyl

VIII

EXAMPLE C11

N-3(1-Morpholino)Propyl 2,4:10,8-Dicarbolactone-5,7-Di-n-Pentyl-6-Thia-Undecane-1,11-Dicarboximide About 24.3 g (ca. 0.05 mole) of 6,6'-thio-bis-(3,5-carbolactone-undercanoic acid) were dissolved in xylene and combined with 7.2 g (ca. 0.05 mole) of N(3-aminopropyl morpholine). The reaction mixture was heated to reflux and after one hour, 1.8 ml of water were collected. The reaction mixture was cooled to room temperature and poured into a large volume of pentane. A white solid precipitated from solution. The solid featured an infrared spectrum with lactone and amide absorption bands at 5.68 and 5.9 microns and analyzed for 60.12% C, 8.41% H, 4.53% N and 5.28% S. Theory requires 62.63% C, 8.42% H, 4.71% N and 5.39% S. Its mass spectrum featured a parent ion at M/z=594 which agrees with the proposed cyclic imide product (Formula VIII, A=3(1-morpholinopropyl).

EXAMPLE C12

N-n-Octadecyl 2,4:11,9-Dicarbolactone-5,8-Di-n-Pentadecyl-6:7-Dithia-Dodecane-1,12-Dicarboximide Twenty grams (ca. 0.025 mole) of Example A41 were dissolved in 100 ml of xylene and combined with 6.7 g (ca. 0.025 mole) of n-$C_{18}H_{37}NH_2$ (purchased as Armeen HT from Armak Corp. of Chicago, Ill.). The mixture was heated at reflux temperature for about 1½ hours. Rotoevaporation of the reaction mixture under high vacuum at 100° C. afforded an oily residue in high yield.

The residue featured an infrared spectrum with prominent lactone and imide absorption bands at 5.68 and 5.9 microns, and analyzed for 1.31% N. Theory requires 1.36% N. Its gel permeation chromatogram featured a single peak having a maximum at Mn=1024.

EXAMPLE C13

N-2-Hydroxyethyl 2,4:10,8-Di-Carbolactone-5,7-Di-n-Pentyl-6-Thia-Undecane-1,11-Dicarboximide Approximately 12.1 g (ca. 0.025 mole) of 6,6'-thio-bis-(3,5-carbolactone-undecanoic acid) were dissolved in 100 ml of xylene and 1.5 g (ca. 0.025 mole) of 2-ethanolamine were added. The reaction mixture was heated to 145° C. for two hours to achieve complete imidation (by IR analysis). At the end of the second hour, the xylene solution was poured into a large volume of pentane, and a white solid precipitated from solution. The product showed an IR spectrum with characteristic lactone and imide carbonyl absorption bands, a mass spectrum with a molecular ion at M/z=511; and analyzed for 59.68% C, 8.05% H, 2.79% N, 22.74% O and 7.14% S. Theory requires 61.05% C, 8.02% H, 2.74% N, 21.92% O and 6.26% S.

EXAMPLE C14

Thio-Bis-Acylation of N-Methyl-Ethanolamine

About 24.3 g (ca. 0.05 mole) of 6,6'-thio-bis-(3,5-carbolactone-undecanioc acid) were dissolved in 100 ml of xylene and 3.75 g (ca. 0.05 mole) of N-methylethanolamine were added dropwise. The reaction mixture was heated at 140° C. for about 3 hours to effect complete amidation and esterification (monitored by infrared analysis). Thereafter, the xylene solution was diluted with 500 ml of pentane and a quantitative yield of a crystalline white solid was obtained. The white powder featured an infrared spectrum with prominent lactone, ester and amide carbonyl absorption bands and analyzed for 62.19% C, 7.95% H, 2.61% N, 21.02% O and 6.56% S. It requries 61.17% C, 8.19% H, 2.66% N, 21.33% O and 6.10% S. The mass spectral analysis of this white solid revealed a strong molecular ion at M/z 252, in harmony with a macrocyclic ester-amide structure. GPC analysis showed macrocyclic ester-amide, but in addition suggested, the presence of 2+2, 3+3 and higher molecular weight cyclic and linear oligomers.

In the following examples, preparative methods are described for the conventional amidation of thio-bis-acylating agents with polyamines, acetylated polyamines, macrocyclic polyamines, and oxyalkylene polyamines, directly or mediated via a promoter such as a carbodiimide.

In addition, synthetic options for designing complexes via the metal template method are also elaborated upon. Variations in the mode of metal complex formation are illustrated by describing (a) the amidation of metalated thio-bis-acylating agent, (b) the thio-bis-acylation of a metal complex of the polyamine and (c) the formation of complexes via addition of a metal salt subsequent to amidation.

EXAMPLE C15

N,N'-Ethylene-Bis-[2,4:10,8-Dicarbo-Lactone-5,7-Di-n-Pentyl-6-Thia-Undecane-1,11-Dicarboximide]

About 24.3 g (ca. 0.05 mole) of 6,6'-thio-bis (3,5-carbolactone-undecanoic acid) were slurried in 100 ml of xylene and stirred at room temperature under a nitrogen blanket. Then, 1.5 g (ca. 0.025 mole) of ethylene diamine were added and the reaction mixture was heated to reflux for about 5 hours to achieve complete amidation (monitored by IR analysis). Rotoevaporation gave an oily residue which was dissolved in 100 ml of acetone. Dilution of the acetone solution with 300 ml of pentane caused a white solid to precipitate from solution. The solid featured an infrared spectrum with strong lactone and amide carbonyl absorption bands and analyzed for 59.42% C, 8.09 H, 3.11% N, 6.43% S. Theory for the title compound requires 62.08% C, 8.33% H, 2.90% N and 6.62% S. GPC analysis of the product reveals a single peak with a maximum at Mn 1348.

EXAMPLE C16

Equimolar Rraction of Ethylene Diamine and Thio-Bis-(Lactone Acid)

Reacting 24.3 g (0.05 mole) of 6,6'-thio-bis-(3,5-carbolactone-undecanoic acid with an equimolar amount of ethylene diamine (3 , 0.05 mole) in 100 ml boiling xylene causes lactonolysis with concerted imidation (IR analysis). The product is precipitated as a white solid from xylene by addition of the xylene solution to a liter of pentane/ether (1:1 by volume). The product analyzed for 5.18% N and 6.44% S (theory for the 1:1 adduct requires 5.50% N and 6.27% sulfur), featured a gel chromatogram with a peak maximum at Mn=1900, and a mass spectrum with a peak at m/z=492.

EXAMPLE C17

Lactone-Imidazolines Via Reaction of Gem-Substituted Ethylene Diamines with Thio-Bis-(Lactone Acid) Reagents Refluxing a mixture of 24.3 g (0.05 mole) of 6,6'-thio-bis-(3,5-carbolactone-undecanoic acid) and 8.8 g (0.1 mole) of 1,2-diamino-2-methylpropane in 100 ml xylene for 12 hours (ca. 3 g water collected) gave a product which featured an IR spectrum with absorption bands ascribable to lactone and imine functionality.

Dilution of the xylene solution in 500 ml pentane afforded a granular solid analyzing for 8.68% N and featuring a mass spectrum with a parent ion at m/z=590 corresponding to the bis-(lactone imidazoline) product featured below:

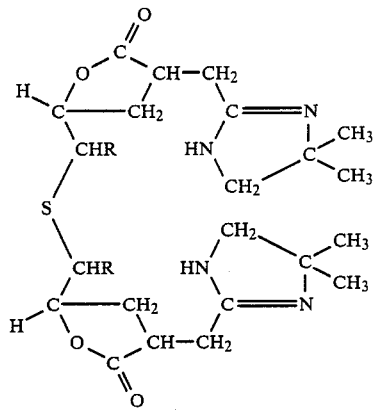

R = n-pentyl

The equimolar reaction of 6,6'-thio-bis-(3,5-carbolactone-undecanoic acid) (12.3 g, 0.025 mole) and 1,2-diamino-2-methylpropane (2.2 g, 0.025 mole) was promoted with 10.3 g (0.05 mole) dicyclohexylcarbodiimide (DCD) in methylene chloride solution. The exotherm produced upon amine addition to the thio-bis-lactone acid and DCD reactants in solution, caused refluxing.

The mixture was refluxed for 12 hours and then diluted with 200 ml of pentane. A white solid separated from solution. The product analyzed for 63.5% C, 9.05% H and 6.31% N, and featured a GPC having a peak maxima at Mn=512 and 888 corresponding to lactone imidazoline and bis-imide products.

EXAMPLE C18

Macrocyclic Imine Derivatives Via 1,3-Propanediamine and Thio-Bis-(Lactone Acid) Reagents Equimolar amounts of 6,6'-thio-bis-(3,5-carbolactone-undecanoic acid) (0.05 mole) and 1,3-propanediamine (0.05 mole) were heated together in boiling xylene (100 ml) until water evolution ceased (12 hours). Dilution of the cooled mixture with 500 ml ether gave a solid having an IR spectrum with prominent bands due to lactone, imide and C=N functionality and analyzing for 5.60% sulfur. The product featured a gel chromatogram with a peak having a maximum at Mn=364 uncorrected and a mass spectrum with a parent peak at M/z=506 in harmony with the structure shown below:

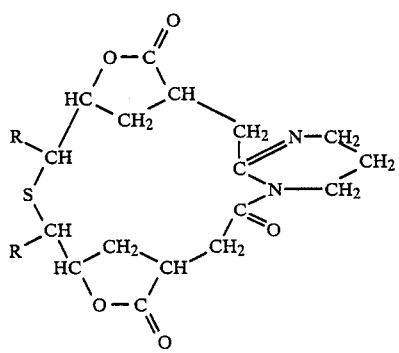

R = n-C$_5$H$_{11}$

Similar results were obtained in the related reaction of 1,3-propanediamine and the 6,6'-dithio-bis-(3,5-carbolactone-undecanoic acid). The resulting product featured a similar IR profile; showed a GPC having a peak maximum at Mn=434.

In the 1:2 reaction of thio-bis-(lactone acid) and 1,3-propanediamine in refluxing toluene, the lactone ring is cleaved (lactonolysis observed by IR analysis) by the amine reagent to generate an imide product.

EXAMPLE C19

Macrocyclic Amides Via Amidation of Thio-Bis-(Lactone Acid Reagents) with N,N'-Dimethyl-Ethylene Diamine A tenth mole (ca. 54.6 g) of Example A31 were dissolved in 100 ml of xylene and 8.8 g (0.1 mole) of N,N'-dimethyl ethylenediamine were added dropwise. The reaction mixture was heated to reflux in a flask equipped with a Dean Stark trap. After three hours, 3.6 ml of methanol were collected and the xylene was removed by rotoevaporation. The residue was dissolved in 50 ml of THF and added dropwise to a liter of pentane. The yellow solid that precipitated was filtered and collected. A high yield of thio-bis-(lactone amide) was obtained. The solid product featured an infrared spectrum with prominent lactone and amide absorption bands at about 5.68 and 6.10 microns; and disclosed a mass spectrum with a parent ion at M/z=528, and analyzed for 60.91% C, 8.73% H, 5.07% N, and 5.28% S. Theory for the macrocycle lactone-amide requires 62.42% C, 8.61% H, 5.20% N, and 5.95% S. GPC analysis shows peak maxima at Mn=521 and 931 indicating the formation of substantial amounts of 1:1 and 2:2 macrocyclic species; the mass spectrum of the product features a parent ion at m/z=538 thus confirming the presence of some 1:1 macrocycle.

EXAMPLE C20

Macrocyclic Amides Via Equimolar Reaction of N,N'-Dimethyl-1,6-Hexandeiamine with Thio-Bis-(Lactone Acid) Reagents About 12.3 g (ca. 0.025 mole) of Example A42 were slurried in 100 ml of methylene dichloride with 10.3 g (0.050 mole) of dicyclohexyl carbodiimide (DCD) and stirred at room temperature for ten minutes. Thereafter, 3.5 g (ca. 0.025 mole) of N,N'-dimethyl-1,6-hexanediamine were added dropwise. After the exotherm ceased, the reaction mixture was allowed to stir at room temperature for ten hours. The dicyclohexylurea was filtered off and the filtrate was dripped slowly into a large volume of pentane. A white solid precipitated from solution. The solid showed an infrared spectrum with absorption bands characteristic of a lactone amide product and analyzed for 64.12 Wt. % C, 9.11 Wt. % H, 4.73 Wt. % N and 4.77 Wt. % S. Theory for the 1:1 adduct requires 64.62 Wt. % C, 9.15 Wt. % H, 4.71 Wt. % N and 5.38 Wt. % S. Analysis of the crude product by GPC suggests the presence of macrocyclic species, viz. the 1:1 adduct (ca. 25 mole %), and a substantial number of larger macrocylic species being present in the oligomeric mixture.

When the above reaction was effected without DCD as promoter, a lactone amide product was obtained with identical IR and elemental analyses, but revealed an Mn of 594 by GPC (calculated Mn for 1:1 macrocycle is 594). The products obtained with and without DCD both featured mass spectra with a strong parent ion at M/z=594.

EXAMPLE C21

N,N-Dimethyl-N,N'-(7-Methyl-7-Aza-Tri-Decane-1,13-Diyl) 6,6'-Thio-Bis-(3,5-Carbolactone-Undecanamide)

About 12.3 g (ca. 0.025 mole) of Example A28 were stirred in 100 ml of methylene dichloride and 10.3 (ca. 0.05 mole) of dicyclohexyl carbodiimide were added. The reaction mixture was stirred at room temperature for ten minutes and 6.42 g (ca. 0.025 mole) of N,N'N''-trimethyl-7-aza-tridecane-1,13-diamine were added dropwise for five minutes. An exothermic reaction took place. The reaction mixture was stirred at room temperature for ten hours. The dicyclohexylurea by-product was filtered off, and the filtrate then dripped into a large volume of pentane. A white solid formed. The solid showed an infrared spectrum with prominent lactone and amide carbonyl absorption bands at 5.65 and 6.05 microns and analyzed for 66.40% C, 9.52% H, 5.92% N and 4.52% S. Theory for the 1:1 macrocycle requires 66.63% C, 9.82% H, 5.94% N and 4.00% S. The gel permeation chromatogram of the product featured a single peak having a maximum at Mn=522; the data indicate that the major product is the 1:1 macrocyle as featured by the structure:

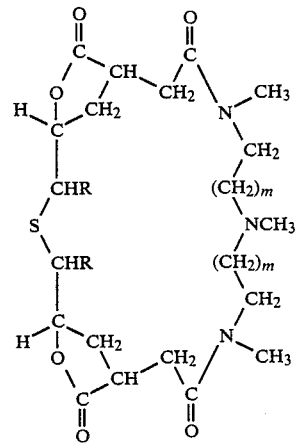

R = n-pentyl
m = 5

EXAMPLE C22

Macrocyclic Amides Via the Equimolar Reaction of 6,10-Dimethyl-2,6,10,14-Tetra-Azapentadecane with Thio-Bis-(Lactone Acid)

About 12.3 g (ca. 0.025 mole) of 6,6'-thio-bis-(3,5-carbolactone-undecanoic acid), were slurried in 100 ml of methylene dichloride and 10.3 g (ca. 0.05 mole) of dicyclohexylcarbodiimide were added. A clear solution was obtained momentarily accompanied by an exotherm, and a white solid precipitated out of solution. The reaction mixture was stirred at room temperature for ten mintues and then 6.1 g (ca. 0.025 mole) of 6,10-dimethyl-2,6,10,14-tetrazapentadecane were added dropwise. An exothermic reaction was observed during the addition. When the exothermic ceased, the reaction mixture was allowed to stir at room temperature for four hours. The dicyclohexylurea was filtered off and the filtrate was dripped into a large volume of pentane. A white solid precipitated from solution. The solids showed an infrared spectrum consistent with the desired thio-bislactone amide product and analyzed for 64.15% C, 9.28% H and 7.69% N. Theory requires 64.12% C, 9.30% H, and 8.08% N. GPC analysis of the white solid showed a single peak with a maximum at Mn=501. The accumulated data are consonant with the structure depicted below:

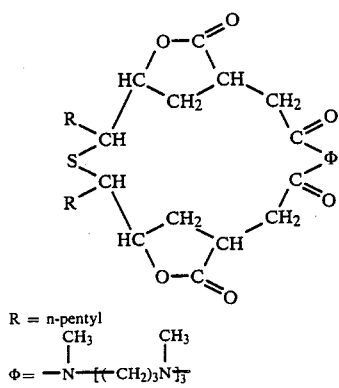

R = n-pentyl

Φ= —N—[(—CH₂)₃N]₃—
        |              |
        CH₃         CH₃

EXAMPLE C23

Carbodiimide-Promoted Amidation of Thio-Bis-(Lactone Acid) with N,N'-Bis-(3-Aminopropyl) Ethylene Diamine About 12.3 g (ca. 0.025 mole) of 6,6'-thio-bis-(3,5-carbolactone-undecanoic acid) and 10.3 g (ca. 0.050 mole) of N,N'-dicyclohexylcarbodiimide were combined in 100 ml of methylene chloride. The reaction mixture was stirred at room temperature for ten minutes. Then, 4.4 g (ca. 0.025 mole) of N,N'-bis-(3-aminopropyl)-ethylene diamine were added. The addition of the amine produced an exothermic reaction. When the exotherm subsided, the reaction mixture was refluxed in methylene chloride for eight hours. The N,N'-dicyclohexylurea was filtered off, and the filtrate was dripped slowly into a large volume of anhydrous ether. Fifteen grams of the white powdery solid were obtained. The infrared analysis of the solid featured absorption bands characteristic of products bearing lactone, imide and amide functionality. The product analyzed for 58.35% carbon, 9.20% hydrogen, and 9.5% nitrogen, and displayed a GPC with a peak maximum at Mn=527, a result which is consonant with a 1:1 macrocyclic species.

EXAMPLE C24

Amidation of Thio-Bis-(Lactone Acid) with Pentapropylene Hexamine

About 12.3 g (ca. 0.025 mole) of 6,6'-thio-bis-(3,5-carbolactone-undecanoic acid) and 10.3 g (ca. 0.050 moles) of N,N'-dicyclohexylcarbodiimide were combined in 100 ml of methylene chloride. The reaction mixture was stirred at room temperature for ten minutes to assure complete conversion of the thio-bis (lactone acid) to the macrocylic anhydride as described in Example A42. Then, 7.6 g (ca. 0.025 moles) of the polyamine, pentapropylenehexamine (BASF Wyanotte Corp.), were added dropwise for a period of ten minutes, and the heterogeneous reaction mixture was refluxed in methylene dichloride for eight hours. The N,N'-dicyclohexylurea that formed was filtered off, and the clear filtrate was dripped into a large volume of anhydrous ether. Fifteen grams of a white powdery solid were obtained. The infrared analysis of the solid featured absorption bands ascribable to thio-bis-lactone imide and amide type products which mixture analyzed for 58.62% carbon, 9.48% hydrogen, and 10.25% nitrogen.

Acetylation of the thio-bis-acylated polyamine afforded a solid product which showed a GPC with a peak maximum at Mn=1046.

EXAMPLE C25

Amidation of Acetylated Thio-Bis-(Lactone Acid) Monamide

About 24.3 g (ca. 0.05 mole) of 6,6'-thio-bis-(3,5-carbolactone-undecanoic acid) and 10.3 g (ca. 0.05 mole) of N,N'-dicyclohexylcarbodiimide were conbined with 100 ml of chloroform and stirred at room temperature for one half hour. The insoluble N,N'-dicyclohexylurea which formed was filtered. Then, 15.1 g (ca. 0.050 mole) of pentapropylene hexamine was added dropwise to the mixture over a period of ten minutes. After addition, the reaction mixture was stirred at room temperature for an hour. The infrared spectrum of the chloroform solution featured strong absorption bands characteristic of a lactone-substituted amic acid.

About 9.24 g (ca. 0.012 moles) of the above amic acid of 6,6'-thio-bis-(3,5-carbolactone-undecanoic acid), and pentapropylenehexamine dissolved in 100 ml of chloroform were treated with 4.9 g (ca. 0.048 moles) of acetic anhydride. The reaction mixture was refluxed in chloroform for eight hours. Then, the clear solution was dripped into a large volume of anhydrous ether. A white solid precipitated out of solution (yield: 9.6 grams). The infrared spectrum of the solid featured absorption bands ascribable to lactone imide and amide type products. It anaylzed for 59.74% carbon, 9.47% hydrogen and 10.85% nitrogen, and showed Mn=1657 by vapor phase osmometry in n-butanol.

EXAMPLE C26

Amidation of Thio-Bis-(Lactone Acid) with an Acetylated Polyamine (1,5,8,12-Tetraazadodecane)

About 30.6 g (ca. 0.3 moles) of acetic anhydride were dissolved in 100 ml of xylene and 8.7 g (ca. 0.05 mole) of 1,5,8,12-tetraazadodecane were added dropwise for a period of five minutes. The addition produced an exothermic reaction. The reaction mixture was then stirred at room temperature for one half hour. Thereafter, 24.3 g (ca. 0.05 mole) of 6,6'-thio-bis-(3,5-carbolactone-undecanoic acid) were added, and the reaction mixture was refluxed for six hours. At the end of the sixth hour, the xylene was evaporated with a stream of nitrogen and the residue was dissolved in acetone. The clear acetone solution was dripped into ether and a yellowish solid precipitated. The infrared spectrum of the solid shows absorption bands ascribable to lactone amide. The solid featured a gel chromatogram with a maximum peak at Mn=510, which confirms the macrocyclic structure and analyzed for 59.23% C, 8.26% H, 6.86% N and 3.68% S. Theory requires 60.58% C, 8.13% H, 7.07% N and 4.04% S for the tetra-acetate derivative.

EXAMPLE C27

Complex Formation Via Amidation of Copper Salt of Thio-Bis-(Lactone Acid) with Polyamine (1,5,8,12-Tetraazadodecane)

About 12.3 g (ca. 0.025 mole) of 6,6'-thio-bis-(3,5-carbolactone-undecanoic acid) and 5 g (ca. 0.025 mole) of cupric acetate were combined in 100 ml of toluene and heated to reflux for one hour. A hazy green solution was obtained. The toluene solution was cooled to room temperature and 20 ml of THF were added to obtain a homogenous bluish-green solution. Then, 4.4 g (ca. 0.025 mole) of N,N'-bis-(3-aminoproyl) ethylene diamine were added. After the exotherm subsided, the reaction mixture was refluxed in toluene for eight hours. The blue toluene solution was filtered and the filtrate was slowly dripped into a large volume of anhydrous ether. A bluish gray solid precipitated from solution. The solid analyzed for 52.22% carbon, 7.87% hydrogen, 7.55% nitrogen, and 7.35% copper. Theory for the macrocyclic complex requires 53.63% C, 7.70% H, 7.00% and 7.35% Cu.

EXAMPLE C28

Complex Formation Via Amidation of Copper Salt of Thio-Bis-(Lactone Acid) with Polyamine (6,10-Dimethyl-2,6,10,14-Tetraaza-Pentadecane)

About 27.4 g (ca. 0.05 moles) of the copper salt of 6,6'-thio-bis-(3,5-carbolactone-undecanoic acid) were dissolved in 200 ml of tetrahydrofuran (THF) and combined with 12.2 g (ca. 0.05 mole) of 6,10-dimethyl-2,6,10,14-tetra-aza-pentadecane. The addition produced an exotherm, and the reaction temperature rose to about 32° C. The reaction mixture was heated to distill off the THF. Xylene was added, and the mixture was refluxed for about eight hours. Rotoevaporation of the reaction mixture under high vacuum at 100° C. produced an oily residue which featured prominent absorption bands for lactone and amide functionality.

EXAMPLE C29

Amidation of Thio-Bis-(Lactone Acid) with Copper Complex of a Polyamine (4,7-Diaza-Decane-1,10-Diamine)

About 12.3 g (ca. 0.025 mole) of 6,6-thio-bis-(3,5-carbolactone-undecanoic acid) were slurried in 100 ml of methylene chloride at room temperature and 10.3 g (ca. 0.050 mole) of dicyclohexylcarbodiimide were added. The reaction mixture was allowed to stir at room temperature for ten minutes. Thereafter, 0.025 mole of the acetate complex of 4,7-diaza-decane-1,10-diamine dissolved in 100 ml of methylene chloride were added. The reaction mixture was stirred at room temperature for about ten hours. The blue solution was filtered and the filtrate was dripped into a large excess of anhydrous ether. A fine blue solid separated. The blue solid (18.5 g) featured an IR spectrum with prominent lactone, imide and amide absorption bands and analyzed for 52.91% C, 7.98% H, 7.87% N and 7.51% Cu. Theory for complex: 53.63% C, 7.70% H, 7.00% N, and 7.88% Cu. The gel chromatogram of the copper complex featured a peak maximum at Mn=369.

EXAMPLE C30

Amidation of Thio-Bis-(Lactone Acid) with the Copper Complex of a Polyamine (6,10-Dimethyl-2,6,10,14-Tetraazapentadecane)

About 12.2 g (ca. 0.05 mole) of 6,10-dimethyl-2,6,10,14-tetraazapentadecane were dissolved in 100 ml of tetrahydrofuran and stirred at room temperature under nitrogen. Then, 10.0 g (ca. 0.05 mole) of cupric acetate were added. The reaction mixture was stirred at room temperature for an hour and a clear, purple solution was obtained. Thereafter, 24.3 g (ca. 0.05 mole) of 6,6'-thio-bis-(3,5-carbolactone-undecanoic acid were added. The reaction mixture was heated and THF was replaced by xylene as it distilled from the reaction flask. Refluxing was continued until removal of the water of reaction was complete. Rotoevaporation at high vacuum at 100° C. produced an oily residue which featured an infrared spectrum with strong absorption bands ascribable to a lactone amide product.

EXAMPLE C31

Amidation of Thio-Bis-(Lactone Acid) Via the Copper Complex of Pentapropylene Hexamine An 0.025 mole of an amine copper complex prepared by mixing 7.55 g (ca. 0.025 mole) of pentapropylenehexamine and 5 g (ca. 0.025 mole) of copper acetate in 100 ml of chloroform was added to a reaction flask containing 12.3 g (ca. 0.025 mole) of 6,6'-thio-bis-(3,5-carbolactoneundecanoic acid) and 10.3 g (0.050 mole) of dicyclohexylcarbodiimide in 100 ml of chloroform. The reaction mixture was then refluxed in chloroform for ten hours and filtered. The filtrate was dripped into a large excess of anhydrous ether and a greenish-blue solid separated. The solid analyzed for 51.74% C, 8.15% H, 9.25% N and 6.64% Cu (theory for complex requires: 9.00% N, and 6.80% Cu) and featured an MN of 850 by vapor phase osmometry (VPO) in n-butanol (calculated Mw=933.5).

EXAMPLE C32

Amidation of Thio-Bis-(Lactone Acid) with 4,7-Diazadecane-1,10-Diamine in the Presence of Copper Acetate About 12.3 g (ca. 0.025 mole) of 6,6'-thio-bis-(3,5-carbolactoneundecanoic acid) were slurried in 100 ml of methylene dichloride and 10.3 g (ca. 0.050 mole) of dicyclohexylcarbodiimide were added. The reaction mixture was stirred for ten minutes at room temperature. Then 4.4 g (ca. 0.025 mole) of 4,7-diazadecane-1,10-diamine were added. An exothermic reaction took place with the addition. Once the exotherm subsided, the reaction mixture was stirred at room temperature for one hour and then 5.0 g (ca. 0.025 mole) of copper acetate monohydrate were added. It was refluxed in methylene dichloride for four hours. The reaction product was filtered and the filtrate was dripped into a large excess of anhydrous ether. A fine blue powder separated (yield: 19.5 g). The solid analyzed for 52.16% C, 7.88% H, 7.50% N and 7.75% Cu, and featured a gel chromatogram having a peak maximum at Mn=846. Theory for the complex requires 53.63% C, 7.70% H, 7.00% N, and 7.88% Cu.

EXAMPLE C33

Thio-Bis-Acylation of a Macrocyclic Polyamine (Cyclam)

About 4.86 g (ca. 0.01 mole) of 6,6'-thio-bis-(3,5 carbolactone-1-undecanoic acid were dissolved in 50 ml of methylene dichloride and combined with 4.1 g (ca. 0.02 moles) of N,N'-dicyclohexylcarbodiimide. The reaction mixture was stirred at room temperature for ten minutes and then 2 g (ca. 0.01 mole) of 1,4,8,11-tetraazacyclotetradecane (cyclam) were added. The methylene chloride slurry was stirred for twelve hours at room temperature. The N,N'-dicyclohexylurea was filtered, and the filtrate was dripped into a large volume of anhydrous ether causing a white solid to precipitate out of solution. The solid featured an infrared spectrum with characteristic absorption bands for a lactone amide.

In a similar manner, a variety of macrocyclic polyamines as illustrated in Formulas VIa, VIb and VIIa–VIIc, can be thio-bis-acylated with III, IV or V to yield a wide spectrum of new and useful multifunctional additives.

In the following experiments, synthetic procedures are defined for the formation of thio-bis-acylated amine products via the sulfur chloride coupling (chlorosulfenylation) of alkene diacid imides and amic acids derived from monoamines and polyamines (including macrocyclic polyamines). In the latter cases, basic nitrogen donors present in the alkene diacid imide or amic acid reactant are first pacified by acetylation or metal complexing to circumvent the rapid sulfenylation of unprotected amine sites by sulfur chloride. Once the basic amine sites in the olefin diacid-polyamine adducts are rendered inert towards sulfenylation, coupling via sulfur chloride addition to the olefinic sites in the adducts becomes feasible, e.g., in 2:1 olefin diacid-polyamine adducts, passivated by acetylation or complexation, bridging via sulfur halide can give substantial yields of acetylated macrocylic products or the macrocyclic complexes.

EXAMPLE C34

N,N'-Dimethyl 5,5'-Thio-Bis-(4-Chloro-4-Methyl-Pentane-1,2-Dicarboximide)

About 33.4 g (ca. 0.2 mole) of N-methyl isobutenyl-succinimide were dissolved in 200 ml of tetrahydrofuran. To the well stirred solution, 10.5 g (ca. 0.1 mole) of sulfur dichloride were added dropwise for a period of fifteen minutes. An exothermic reaction took place with the addition of SCl$_2$ and the reaction temperature peaked at 34° C. Once the exotherm ceased, the reaction mixture was stirred at room temperature for three days. Rotoevaporation of the mixture at 100° C. for one hour gave an oil residence which featured a gel chromatogram with a single peak corresponding to the bridged structure IX shown below. The mass spectrum showed a peak at M/z=364 which corresponds to the dehydrochlorinated product.

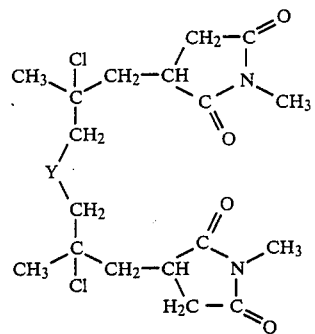

Y = S

EXAMPLE C35

N,N'-Dimethyl 5,5'-Dithio-Bis-(4-Chloro-4-Methyl-Pentane-1,2-Dicarboximide)

About 22.3 g (ca. 0.1 mole) of N-methyl diisobutenyl-succinimide were dissolved in 100 ml of anhydrous ether and 6.8 g (ca. 0.05 mole) of sulfur monochloride were added dropwise to the well-stirred solution at room temperature. After the addition was completed, the reaction mixture was allowed to stand at room temperature for several days. A white solid precipitated out of solution. The infrared spectrum of the solid featured strong imide carbonyl absorption bands for the sulfur bridged succinimide product which melted at 167°–168° C. The gel chromatogram of the product showed a single peak corresponding to the chlorine containing bridged succinimide and a mass spectrum having a base peak at m/z=508 (M-2HCl), thus confirming the structure for the title compound.

EXAMPLE C36

Addict of Sulfur Monochloride and N-Methyl Tetraisobutenyl-Succinimide

The N-methylsuccinimide of tetraisobutenylsuccinic anhydride (TBSA) was prepared by heating the amic acid precursor [formed by treating 0.1 mole (32.3 g) of TBSA with 0.13 mole (ca. 4 g) of gaseous methylamine] in refluxing xylene until imidation was complete by IR analysis (water of reaction was collected in a Dean-Stark trap).

At this point, 6.8 g (0.05 mole) of sulfur monochloride were added dropwise to the stirred xylene solution kept at ca. 25° C. (S$_2$Cl$_2$ addition induced an exotherm). Besides other confirming analytical data, clinching evidence for formation of the adduct came from GPC analysis which revealed the virtual disappearance of the reactant peak (maximum at Mn=234 uncorrected) and the appearance of the adduct peak at Mn=439 (uncorrected).

EXAMPLE C37

Adduct of Sulfur Dichloride and the Bis-Amic Acid from NOSA and N,N'-Dimethyl Hexane-1,6-Diamine The amic acid was prepared via the dropwise addition of 14.4 g (0.1 mole) of N,N'-dimethyl hexane-1,6-diamine to 0.2 mole (42 g) of n-octenyl-succinic anhydride (NOSA) dissolved in tetrahydrofuran (THF) at room temperature. The THF solution was stirred at 25° C. for an hour after amine addition, and then, 0.1 mole (10.6 g) of SCl$_2$ were added dropwise at about 25° C.

The mixture was allowed to stir at ambient temperature for 2 days, and subsequently rotoevaporated to a residue which showed an infrared spectrum consistent with a lactone amide product.

EXAMPLE C38

Adduct of Sulfur Dichloride and Acetylated Bis-Imide from N-Octenyl Succinic Anhydride (NOSA) and 1,5,8,12-Tetra-Azadodecane About 84 g (ca. 0.4 mole) of n-octenylsuccinic anhydride were dissolved in 200 ml of xylene and 34.8 g (ca. 0.2 mole) of N,N'-bis-(3-aminopropyl) ethylene diamide were added dropwise over a period of twenty minutes. After the addition was complete, the reaction mixture was refluxed to effect removal of the water of reaction. At the end of the third hour, all the water of reaction was collected. An infrared spectrum of the xylene solution showed complete conversion to the bis-imide product. Then, about 100 ml of acetic anhyride were added and the reaction mixture was refluxed for another three hours to effect complete acetylation of the remaining basic secondary amine sites. One half of the xylene solution of the bis-imide was charged into a reaction flask and freed of solvent. The residue was dissolved in 200 ml of THF and stirred at room temperature while 10.2 g (ca. 0.1 mole) of sulfur dichloride were added over a period of five minutes. Once addition was complete, the reaction mixture was allowed to stir at room temperature for ten hours. The THF solution was dripped into a large volume of pentane and a yellowish solid precipitated out of solution (yield: 72 g). The solid product analyzed for 54.82% C, 7.58% H, 7.03% N, 5.26% S and 10.18% Cl and featured a GPC with at peak maximum at $Mn = 1960$.

EXAMPLE C39

Complex of Adduct from Sulfur Dichloride and Bis-Imide of NOSA and 1,5,8,12-Tetraazadodecane One half of the bis-imide prepared above, was stripped with nitrogen and the residue was dissolved in 200 ml of THF. The THF solution was stirred at room temperature, and 19.9 g (ca. 0.1 mole) of cupric acetate were added. After a few minutes a clear greenish solution was obtained. Then, 10.2 g (ca. 0.1 mole) of sulfur dichloride were added. After the exotherm subsided, the reaction mixture was stirred at room temperature for three hours. The hazy solution was filtered and the filtrate was dripped into a large volume of pentane and a yellowish solid separated from solution. The product analyzed for 51.30% C, 7.14% H, 6.71% N, 4.78% S, 8.85% Cl and 5.4% Cu, and featured a gel chromatogram having a peak maximum at $Mn = 437$. Theory for the complex requires: 51.28% C, 7.12% H, 6.65% N, 3.8% S, 8.43% Cl.

EXAMPLE C40

Adduct of Sulfur Dichloride and Bis-Amide from Isobutenylsuccinic Anhydride and 4,7,10-Trioxa Tridecane-1,13-Diamine The bis-imide reactant was prepared by adding dropwise 22 g (ca. 0.1 mole) of 4,7,10-trioxatridecane-1,13-diamin (polyglycoldiamine (H-221) obtained from Union Carbide Corp., New York) of 30.8 g (0.2 mole) of isobutenylsuccinic anhydride dissolved in 100 mol of xylene. The mixture was refluxed until imidation was complete by IR analysis.

Sulfenylation of the unsaturated bis-imide reactants was achieved via the dropwise addition of 0.1 mole of $SCl_2$ to the xylene solution of the bis-imide at room temperature. Rotoevaporation afforded a residue which featured imide functionality by IR analysis.

EXAMPLE C41

Adducts of Sulfur Halida and Alkene-Substituted Macrocyclic Polyamines (ASMP) [From Condensation of Oligomeric Polytrimethylene-Polyamines with Olefin Monoacids and/or Olefin Diacids]

A variety of ASMP reactants (VIa and VIb where R=alkenyl) can be coupled under suitable reaction conditions providing the basic nitrogen donor atoms in the ASMP reagent are passified by acetylation, or complexation; or the coupling with sulfur halide is effected in an acid medium which precludes the nitrogen donors from interacting.

Typically, an alkene-substituted macrocyclic polyamine ASMP (prepared for example, via the condensation of equimolar amounts of isobutenylsuccinic anhydride and 3,3'-imino-bis-propylamine in refluxing xylene until 2 moles of water of reaction are removed) is dissolved in acetic acid and/or anhydride and selectively chlorosulfenylated at the olefinic function via the dropwise addition of a half-molar amount (2 ASMP: 1 $S_xCl_2$) of sulfur halide (x=1 and/or 2) to the stirred solution kept at 0° C. After addition, the mixture is refluxed for several hours, then treated with sufficient base (e.g. $Na_2CO_3$) to remove chloride ion, and finally filtered through celite. The heat product is obtained from the filtrate by rotoevaporation at 100° C. for several hours. A useful repertory of ASMP reactants (see VIa and VIb where R=alkenyl) can be obtained via acylation of such polyamines as $NH_2(CH_2CH_2CH_2NH)_mH$ wherein $m = 1-10$, and $NH_2CH_2CH_2CH_2NHCH_2CH_2NHCH_2CH_2CH_2NH_2$, with an olefin mono acid or olefin diacid.

D. AMIDATION OF MACRO THIO-BIS-ACYLATING REAGENTS

In the subsequent examples, synthetic procedures are put forth to illustrate the design of thio-bis-acylated polyamines, via the amidation of thio-bis-(polybutyl lactone acid) and thio-bis-(polybutenylsuccinic anhydride) reactants with commercial polyamines such as E-100, a product of Dow Chemicals, Midland, Michigan.

The composition of Dow E-100 is given below:

| Composition of Dow E-100 | |
|---|---|
| % Nitrogen | 33–34 |
| % Primary Amine | 11.1–11.6 |
| % Secondary Amine | 14.4–16.1 |
| % Tertiary Amine | 5.7–6.5 |
| Basic Nitrogen | 29–31 |
| Amine Hydrogen Equivalent Weight | 23–26 |
| % Acetylatable Nitrogen | 28.8–29.2 |
| % TEPA (Tetraethylene Pentamine) | 8.7–8.8 |
| % PEHA (Pentaethylene Hexamine) | 30–36 |
| % HEHA* and Highers | 55–62 |

*(Hexaethylene heptamine)

In several cases, methods are described for the formation of boron and molybdenum containing thio-bis-acylated polyamine dispersants.

EXAMPLE D1

About 26.3 g (ca. 0.01 mole) of the thio-bis-(polyisobutyl lactone acid) prepared as described in Example B1 were mixed with 2.0 g (ca. 0.01 mole) of polyamine (Dow E-100), and heated to 150° C. for two hours with stirring and nitrogen sparging. The reaction product was diluted with an equal amount of mineral oil Solvent 150 Neutral and filtered. It analyzed for 1.36 Wt. % nitrogen. It featured an infrared spectrum with strong absorption bands ascribable to lactone imide/amide product.

EXAMPLE D2

Thirty-seven grams (ca. 0.014 mole) of the thio-bis (polyisobutyl lactone acid), prepared via the hydrolysis of the adduct of poly-isobutenylsuccinic anhydride and $SCl_2$ (B2), were dissolved in 38 g of mineral oil Solvent 150 Neutral and heated to 150° C. under nitrogen. While stirring at this temperature, 1.5 g of PAM were added and the reaction mixture was nitrogen sparged for two hours. At the end of the second hour, the product was filtered and analyzed. The infrared spectrum of the diluted product showed absorption bands ascribable to lactone imide product. The latter analyzed for 0.56% S and 0.97% N.

EXAMPLE D3

Approximately 53 g (ca. 0.02 moles) of the dithio-bis-(polyisobutyl lactone acid), prepared in Example B3 were mixed with an equal weight of mineral oil (Sovent 150 Neutral), and heated to 150° C. While at this temperature, 2.1 g (ca. 0.01 mole) of PAM were added dropwise over a period of five minutes. The reaction mixture was nitrogen sparged for two hours at 150° C. and filtered. The filtered product showed an infrared spectrum consistent with a dithio-bis-(polyisobutyl lactone imide/amide) product, and analyzed for 0.97 Wt. % N and 1.36 Wt. % S.

EXAMPLE D4

About 30 g (ca. 0.014 mole) of a dithio-bis-(polybutyl lactone acid) derived from a PIBSA made via the ene process and having a Saponification Number of 107 were dissolved in 32 g of mineral oil Solvent 150 Neutral and heated to 150° C. Thereafter, 2.9 g (ca. 0.014 mole) of polyamine (Dow E-100) were added dropwise while stirring at 150° C. under nitrogen. The reaction mixture was nitrogen sparged at 150° C. for two hours and filtered. The dithio-bis-(polybutyl lactone imide) (50% a.i.) analyzed for 1.75 Wt. % N.

EXAMPLE D5

About 24 g (ca. 0.01 mole) of the thio-bis-(polyisobutyl lactone acid) prepared as in Example B7 was dissolved in 16 g of mineral oil (Solvent 150 Neutral) and heated to 150° C. Then, 2 g of Polyamine, Dow E-100, were added dropwise. Upon completion of the addition, the reaction mixture was nitrogen sparged at 150° C. for two hours and then filtered through a cake of celite 503. The filtrate featured an infrared spectrum with strong absorption bands at 5.65 and 5.9 microns ascribable to products bearing lactone and imide functionality and analyzed for 1.42 Wt. % N and 0.69 Wt. % S.

EXAMPLE D6

About 24 g of a thio-bis-(polyisobutyl lactone acid) of Example B7 were mixed with 16 g of mineral oil (Solvent 150 Neutral) and heated to 150° C. To the stirred solution, 4 g (0.002 mole) of Polyamine (Dow E-100) were added dropwise for a period of five minutes. Then, the reaction mixture was nitrogen sparged at 150° C. for two hours. The oil solution was filtered through a cake of Celite 503. The filtrate featured an IR spectrum with strong absorption bands at 5.65, 5.90 and 6.1 microns indicating the presence of lactone, imide and amide functionally. It analyzed for 2.35 Wt. % N, and 0.69 Wt. % S.

EXAMPLE D7

About 26.5 g (ca. 0.009 moles) of the dithio-bis-(polyisobutenyl succinic anhydride) prepared in Example B4 were diluted with 26 g of mineral oil (Solvent 150 Neutral) and heated to 150° C. While stirring under a nitrogen blanket at 150° C., 1.8 g (ca. 0.009 mole) of Polyamine (Dow E-100) were added dropwise for a period of five minutes. When the addition was completed, the reaction product was nitrogen sparged for two hours at 150° C. and filtered. The filtered solution featured an infrared spectrum consistent with a dithio-bis-(polyisobutenyl succinimide) product and analyzed for 1.76 Wt. % N and 0.69 Wt. % S.

EXAMPLE D8

About 24 g (ca. 0.01 mole) of a thio-bis-(polyisobutenyl succinic anhydride) of Example B6 were dissolved in 24 g of mineral oil (Solvent 150 Neutral) and heated to 150° C. while stirring under a nitrogen blanket. The 2 g (ca. 0.01 mole) of Polyamine (Sow E-100) were added dropwise. The reaction mixture was nitrogen sparged at 150° C. for two hours. At the end of the second hour, the oil solution was filtered through a filter cake of Celite 503. The infrared spectrum of oil diluted product featured strong absorption bands attributable to thio-bis-(polyisobutenyl succinimide) product. The dispersant analyzes for 1.33 Wt. % N and 0.69 Wt. % S.

EXAMPLE D9

About 24 g of the thio-bis-(polyisobutenyl succinic anhydride) of Example B6 were mixed with 14 g of mineral oil (Solvent 150 Neutral) and heated to 150° C. Then, 2 g of Polyamine (Dow E-100) were added. The reaction mixture was nitrogen sparged at 150° C. for two hours and then filtered. The filtrate featured an IR similar to Example D8 and analyzed for 1.68 Wt. % N and 0.71 Wt. % S.

EXAMPLE D10

Approximately 80 g (ca. 0.03 mole) of the adduct prepared as described B9 were dissolved in an equal weight of mineral oil (Solvent 150 Neutral) and heated to 150° C. While stirring under nitrogen, 6.34 g (ca. 0.03 mole) of Polyamine (Dow E-100) were added dropwise for a period of 15 minutes. When the addition was completed, the reaction mixture was nitrogen stripped at 150° C. for two hours. The filtered product analyzed for 1.34 Wt. % N and 0.65 Wt. % S and featured an infrared spectrum consistent with a thio-bis-(polyisobutenyl-succinimide) product.

EXAMPLE D11

About 26 g (ca. 0.01 mole) of the adduct described in Example B9 were mixed with 26 g of Solvent 150 Neutral and heated to 150° C. While stirring under nitrogen, 2.0 g (0.1 mole) of Polyamine (Dow E-100) were added dropwise for about five minutes and the reaction mixture was then nitrogen sparged at 150° C. for two hours. At the end of the second hour, the reaction product was filtered and collected. It analyzed for 1.67 Wt. % N and 0.53 Wt. % S.

EXAMPLE D12

One hundred grams (ca. 0.05 mole) of the adduct prepared in Example B10 were dissolved in 106 g of Solvent 150 Neutral and heated to 150° C. Then, 10.4 g (ca. 0.05 mole) of PAM were added dropwise for a period of 15 minutes. When the addition was completed, the reaction product was nitrogen sparged at 150° C. for two hours and filtered. The filtered solution showed an infrared spectrum consistent with a dithio-bis-(polyisobutenyl succinimide) product and analyzed for 1.69 Wt. % N and 0.97 Wt. % S.

EXAMPLE D13

Approximately 30 g (ca. 0.014 mole) of the dehydrochlorinated adduct of ene PIBSA of Sap. No. 107 and $S_2Cl_2$ were dissolved with 32 g of mineral oil and heated to 150° C. While stirring under nitrogen, 2.9 g (ca. 0.014 mole) of Polyamine (Dow E-100) were added dropwise over a period of 5 minutes. The reaction product was nitrogen sparged for two hours at 150° C. and then filtered. The filtered solution featured an infrared spectrum consistent with a dithio-bis-(polyisobutenyl imide) product and analyzed for 1.7 Wt. % N.

EXAMPLE D14

About 17 g of Example D5 were mixed with 0.4 g of boric acid and heated to 150° C. The reaction mixture was nitrogen sparged at 150° C. for two hours and filtered. The filtrate analyzed for 0.20 Wt. % Boron and 0.69 Wt. % S.

EXAMPLE D15

Approximately 30 g of the oil solution of Example D9 were mixed with 0.7 g of boric acid and heated slowly to 150° C. The reaction mixture was nitrogen sparged at 150° C. for two hours. At the end of the second hour, the product was filtered. The filtered oil solution of the borated thio-bis-(polyisobutenyl succinimide) analyzed for 0.49 Wt. % Boron, 1.68 Wt. % N and 0.56 Wt. % S.

EXAMPLE D16

About 63 g of Example D10 were heated to 150° C. and 1.42 g of boric acid were added. The reaction mixture was then nitrogen sparged for two hours at 150° C. At the end of the second hour, the product was filtered. The filtrate analyzed for 0.36 Wt. % Boron.

EXAMPLE D17

Approximately 12 g of product prepared according to the procedure outlined in Example D5 were dissolved in 100 ml of xylene and mixed with 1.8 g of 85% molybdic acid. The slurry was refluxed for ten hours and then filtered. Rotoevaporation of the filtrate at 100° C. under high vacuum afforded a dark green oil solution which analyzed for 6.28 Wt. % Mo.

EXAMPLE D18

About 24 g of the aminated thio-bis-(polyisobutyl lactone acid) described in Example D6 were dissolved in 24 g of Solvent 150 Neutral and 100 ml of xylene. Then, 3.2 g of molybdic acid were added, and the slurry was heated to reflux for ten hours. Rotoevaporation of the filtered product at 100° C. under high vacuum for four hours afforded a dark green oil solution which analyzed for 2.4 Wt. % Mo.

EXAMPLE D19

Approximately 30 g (ca. 0.015 mole) of a thio-bis-(polyisobutenyl succinic anhydride) were dissolved in 30 g of mineral oil and heated to 150° C. while stirring under a nitrogen blanket. Then 4 g (ca. 0.02 mole) of Polyamine (Dow E-100) were added dropwise. The reaction mixture was nitrogen sparged at 150° C. for two hours. At the end of the second hour, the oil solution was diluted in 100 ml of xylene and 3.2 g of molybdic acid were added. The slurry was heated to reflux for eight hours, filtered and rotoevaporated at 100° C. under high vacuum to give a product which analyzed for 4.08 Wt. % Mo.

EXAMPLE D20

According to Example I in U.S. Pat. No. 3,470,098, 100 g of an oil solution of a polyisobutenylsuccinic anhydride/tetra ethylene pentamine dispersant (molar ratio 2.1/1) containing 50 Wt. % mineral lubricating oil and 50 Wt. % dispersant, was heated with 10 g of sulphur monochloride for about one hour at 149° C. with $N_2$ blowing. At the end of this time, the resulting product was cooled and filtered. The product analyzed for 1.44% nitrogen, 5.13% S and 2.03% Cl.

EXAMPLE D21

According to Example III described in U.S. Pat. No. 3,390,086, about 100 g of a lubricating oil solution consisting of about 50 weight percent mineral lubricating oil and about 50 weight percent of a polyisobutenyl succinic anhydride/tetra ethylene pentamine dispersant (molar ratio 2.1/1) were charged to a reaction flask and heated to 143° C. over a period of 40 minutes. Elemental sulphur was added as a yellow powder over a period of 3 minutes. The temperature was held at 149°–150° C. while the sulphur was stirred into solution. After five minutes, the reaction appeared complete and the product was allowed to cool to room temperature. The oil solution analyzed for 1.51% Nitrogen and 1.63% Sulphur.

EXAMPLE D22

In accord with Example 2, described in U.S. Pat. No. 3,309,316, 200 g of a lubricating oil solution containing 50 Wt. % of polyisobutenyl succinic anhydride (Mn=980) were charged into a reaction flask and heated to 135° C. while stirring under a nitrogen blanket. Elemental sulfur (3.5 g) was added as a yellow powder over a period of three minutes. The reaction temperature was increased to 177° C. and kept at this temperature for about six hours while sulfur was stirred into said solution. At the end of the sixth hour, the oil solution was filtered. It analyzed for 1.23% Sulfur. Upon standing some sulfur precipitated out of solution.

About 70 g (ca. 0.035 mole) at the 50 Wt. % active ingredient sulfur containing PIBSA, prepared as above, were charged into a reaction flask and heated to 150° C. Then, 3.5 g (ca. 0.017 mole) of Dow E-100 Polyamine were added dropwise over a period of five minutes. The reaction mixture was nitrogen stripped at 150° C. for 2 hours. At the end of the second hour, the oil solution was filtered. The filtrate analyzed for 1.18% Nitrogen and 0.82% Sulfur.

EXAMPLE D23

A sample of Cl-PIBSA (210 g, ca. 0.21 mole) having a Sap. No. of 112 and Mn=980 by VPO, was diluted with 200 g of mineral oil (Solvent 150 Neutral) was charged into a reaction flask and heated to 150° C.

Approximately a tenth mole (ca. 20 g) of Polyamine (Dow E-100) were added dropwise over a half hour period, while the reaction mixture was sparged with nitrogen. After addition, the reaction mixture was sparged further with nitrogen for 2 hours at 150° C. Then 2.7 g of boric acid were added, and the reaction mixture was heated for another 2 hours at 150° C. The filtered polyisobutenylsuccinimide dispersant analyzed for 1.56% Nitrogen and 0.39% Boron.

EXAMPLE D24

About 10 g of a thio-bis-(polyisobutenyl lactone acid) prepared as in Example B2 were dissolved in 10 g of Solvent 150 Neutral and combined with 1.94 g of a TEPA-copper acetate complex. The mixture was heated to 150° C. for two hours while nitrogen sparging and filtered. A dark green oil solution was obtained.

EXAMPLE D25

In the same manner, 10 g of the thio-bis-(polyisobutenyl lactone acid) were diluted in 10 g of oil and reacted with 1.5 g of a molydbic acid TEPA complex. The filtered product gives a dark green solution off the desired molybdenum containing dispersant.

EXAMPLE D26

Evaluation of Products in Sludge Inhibition Bench (SIB) Test

The products of the above examples were subjected to a Sludge Inhibition Bench (SIB) Test which has been found after a large number of evaluations, to be an excellent test for assessing the dispersing power of lubricating oil dispersant additives.

The medium chosen for the Sludge Inhibition Bench Test was a used crankcase mineral lubricating oil composition having an original viscosity of about 325 SUS at 37.8° C. that had been used in a taxicab that was driven generally for short trips only, thereby causing a buildup of a high concentration of sludge precursors. The oil that was used contained only a refined base mineral lubricating oil, a viscosity index improver, a pour point depressant and zinc dialkyldithiophosphate antiwear additive. The oil contained no sludge dispersants. A quantity of such used oil was acquired by draining and refilling the taxicab crankcase at 1,000–2,000 mile intervals.

The Sludge Inhibition Bench Test is conducted in the following manner. The aforesaid used crankcase oil, which is milky brown in color, is freed of sludge by centrifuging for ½ hour at about 39,000 gravities (gs.). The resulting clear bright red supernatant oil is then decanted from the insoluble sludge particles thereby separated out. However, the supernatant oil still contains oil-soluble sludge precursors which on heating under the conditions employed by this test will tend to form additional oil-insoluble deposits of sludge. The sludge inhibiting properties of the additives being tested are determined by adding to portions of the supernatant used oil, a small amount, such as 0.5 Wt. %, on an active ingredient basis, of the particular additive being tested. Ten grams of each blend being tested is placed in a stainless steel centrifuge tube and is heated at 137.8° C. for 16 hours in the presence of air. Following the heating, the tube containing the oil being tested is cooled and then centrifuged for 30 minutes at about 39,000 gs. Any deposits of new sludge that form in this step are separated from the oil by decanting the supernatant oil and then carefully washing the sludge deposits with 15 ml of pentane to remove all remaining oil from the sludge. Then the weight of the new solid sludge that has been formed in the test, in milligrams, is determined by drying the residue and weighing it. The results are reported as milligrams of sludge per 10 grams of oil, thus measuring differences as small as 1 part per 10,000. The less new sludge formed the more effective is the additive as a sludge dispersant. In other words, if the additive is effective, it will hold at least a portion of the new sludge that forms on heating and oxidation, stably suspended in the oil so it does not precipitate down during the centrifuging.

Using the above-described test, the dispersant activity of the additive compounds according to the present invention were compared with a commercially available polyisobutenylsuccinimide dispersant (product of Example D23).

The test results are given in Table I.

TABLE I

SLUDGE DISPERSANCY TEST RESULTS

| Test Sample | Additive of Example | Mg Sludge/10 g Oil at | | |
|---|---|---|---|---|
| | | 0.5 Wt. % | 0.8 Wt. % | 1.0 Wt. % |
| I-1 | D1 | 4.51 | 0.82 | 0.66 |
| I-2 | D3 | 5.19 | 2.88 | 0.00 |
| I-3 | D5 | 3.93 | 0.33 | 0.00 |
| I-4 | D6 | 0.00 | 0.00 | 0.00 |
| I-5 | D7 | 0.00 | 0.00 | 0.00 |
| I-6 | D8 | 4.38 | 1.52 | 0.00 |
| I-7 | D9 | 2.87 | 0.56 | 0.00 |
| I-8 | D11 | 1.77 | 0.00 | 0.00 |
| I-9 | D12 | 3.60 | 0.00 | 0.00 |
| I-10 | D13 | 1.12 | 0.00 | 0.00 |
| I-11 | D23 | 5.67 | 2.74 | 1.15 |
| I-12 | Blank | 10.00 | 10.00 | 10.00 |

The results set forth in Table I show that the thio-bis-acylated polyamine dispersants prepared according to the present invention are more effective sludge dispersants than the commercial type of polyisobutenylsuccinimide dispersant, i.e., Example D23.

EXAMPLE D27

Evaluation of Products in Varnish Inhibition Bench (VIB) Test

Each test sample consisted of 10 g of lubricating oil containing 0.07 of a gram of the additive concentrate (50% active) which results in a total of 0.35 Wt. % additive present in the test sample. The test oil to which the additive is admixed was 9.93 g of a commercial lubricating oil obtained from a taxi after 2,000 miles of driving with said lubricating oil. Each ten gram sample was heat soaked overnight at about 140° C. and thereafter centrifuged to remove the sludge. The supernatant fluid of each sample was subjected to heat cycling from about 150° C. to room temperature over a period of 3.5 hours at a frequency of about 2 cycles per minute. During the heating phase the gas containing a mixture of about 0.7 volume percent $SO_2$, 1.4 volume percent NO and balance air was bubbled through the test samples and during the cooling phase water vapor was bubbled through the test samples. At the end of the test period, which testing cycle can be repeated as necessary to determine the inhibiting effect of any additive, the wall surfaces of the test flasks in which the samples were contained are visually evaluated. Flasks in which the samples were contained are visually evaluated as to the varnish inhibition. The amount of varnish imposed on the walls is rated at values of from 1 to 7 with the higher number being the greater amount of varnish. It has been found that this test correlates with the varnish results obtained as a consequence of carrying out an MS-VC engine test. The results of the VIB testing of candidate and commercial dispersants are recorded in Table II below.

TABLE II

| Test Sample | Additive of Example | VIB Rating |
|---|---|---|
| 0.5 WEIGHT PERCENT OF ADDITIVE ADDED TO TEST OIL | | |
| II-1 | D2 | 4 |
| II-2 | D6 | 4 |
| II-3 | D7 | 5 |
| II-4 | D13 | 4 |
| II-5 | D14 | 4 |
| II-6 | D20 | 10 |
| II-7 | D21 | 9½ |
| II-8 | D22 | 10½ |
| II-9 | D23 | 7 |
| II-10 | Blank | 11 |

The data in Table II illustrate the outstanding varnish-inhibition activity of the additive compounds (including a borated derivative -see Test Sample II-5) according to the present invention when compared with a commercial-type polyisobutenylsuccinimide dispersant (Example D23), and other sulfur-containing dispersants (Examples 20-22) of the prior art.

EXAMPLE D28

Evaluation of Products by Thermogravimetric Analysis (TGA)

Three of the thio-bis-acylated polyamine products of the present invention and a commercial-type succinimide dispersant (Example D23) diluted in mineral oil were evaluated by thermogravimetric analysis (TGA) for evidence of thermal stability under oxidative conditions provided by air flow across each sample heated linearly from about 50° C. to 450° C. at a rate of 6°/min. Each sample of 200 mg in a stainless steel planchette was continuously weighed and recorded as the temperature was programmed upwardly at a linear rate to provide a record of sample weight versus temperature. The results are found in Table III.

TABLE III

| Test Sample No. | Product Additive Tested | Temperature at which the indicated percentage weight loss occurred | | | |
|---|---|---|---|---|---|
| | | 10 Wt. % °C. | 50 Wt. % °C. | 70 Wt. % °C. | 90 Wt. % °C. |
| 1 | Solvent 150N Mineral Oil | 239 | 283 | 295 | 310 |
| 2 | DI | 255 | 283 | 410 | 310 |
| 3 | D3 | 265 | 355 | 405 | 435 |
| 4 | D7 | 275 | 370 | 415 | 440 |
| 5 | D23 | 250 | 350 | 405 | 410 |

The TGA data shown in Table III reveal that the compositions of the present invention are significantly more stable towards heat and oxidation than the reference commercial-type polyisobutenylsuccinimide dispersant, Ex. D23. In addition, the TGA data show that the thio-bis-acylated nitrogen containing additives of the present invention tend to stabilize the base oil, e.g. S-150N base stock oil, towards thermal oxidative degradation. Thus, the novel structural features built into the present dispersants endow these additives with enhanced thermal stability as well as the ability to inhibit oxidation of the base stock oil. It is believed that these inhibitor properties can be related in part to the presence of sulfide functionality present in the additive molecules of the present invention.

EXAMPLE D29

Evaluation of Products in Normal Four Ball Friction Tests

The molybdated dispersants of Examples D17, D18 and D19 were evaluated in a formulated oil for its effect on friction in a Roxana Four-Ball Tester. As a comparative example, an oil containing a commercial succinimide dispersant without molybdenum was run. The concentration of the molybdenum-containing dispersant was adjusted to provide 0.1% molybdenum in the oil. A total dispersant concentration of 2.5% was maintained in all tests.

The lubricant composition was:

| Component | Wt. % Active Ingredient |
|---|---|
| Dispersant | 2.5 |
| Magnesium Sulfonate (Overbased) | 0.4 |
| Zinc dinonyl phenoxy dithiophosphate | 1.0 |
| Mineral oil | 96.1 |

The Roxana Four-ball wear tested with the Brown-GE modification from Roxana Machine Works, St. Louis, Mo., was used to measure friction properties by the following procedure. The tester was assembled in the normal wear procedure as described in ASTM D2266-67 using four ¼" bearing steel balls. The tester was brought to 110° C. and run at 1200 rpm and 15 kg for a minimum of 45 minutes. If the frictional force as seen on the strip chart recorder is constant for the last 10 minutes, the speed is reduced to 25 rpm. Otherwise, the test carried on until frictional force has stabilized. The test at 25 rpm is carried out at 110° C. and 15 kg for 15 minutes or until frictional force has stabilized.

The representative compounds of the invention were evaluated by subjecting the products of Examples D17, D18 and D19 to a study of each one's utility as a lubricity enhancing and/or antiwear additive for lubricating oils by using said Testing Procedure.

The results of tests under said Testing Procedure A are set forth in Table IV.

TABLE IV

COMPARISON OF MOLYBDENUM CONTAINING DISPERSANTS FOR FRICTION REDUCTION

| Test # | Molybdate Product of Example # | Coefficient of Friction (1) | | Friction Reduction (2) | |
|---|---|---|---|---|---|
| | | 1200 rpm | 50 rpm | 1200 rpm | 50 rpm |
| IV-1 | D17 | 0.052 | 0.049 | 44 | 55 |
| IV-2 | D18 | 0.047 | 0.079 | 50 | 27 |
| IV-3 | D19 | 0.047 | 0.040 | 50 | 63 |
| IV-4 | — | 0.093 | 0.108 | — | — |

(1) 15 kg load
(2) Relative to base oil reported as IV-4

From the foregoing, it is shown that the molybdenum-containing thio-bis acylated polyamine dispersant additives of the invention provide lubricity enhancement to lubricating oils.

It is to be understood that the Examples present in the foregoing specification are merely illustrative of this invention and are not intended to limit it in any manner; nor is the invention to be limited by any theory regarding its operability. The scope of the invention is to be determined by the appended claims.

What is claimed is:

1. An acylated amine composition comprising reaction product obtained by reacting
   (i) thio- bis-hydrocarbon-substituted acylating agent selected from the group consisting of thio-bis-hydrocarbon-substituted acylating agents represented by the following formulae

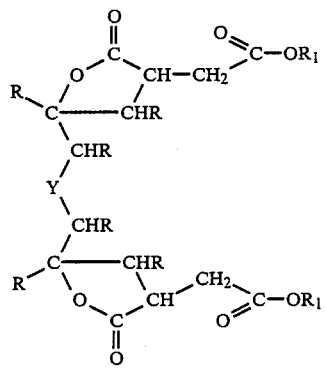

wherein: R is selected from the group consisting of hydrogen, hydrocarbyl and halo substituted hydrocarbyl containing from 1 to 10,000 carbons with the proviso that at least one R has at least four carbons; the bridging or coupling element, Y, is selected from the group consisting of S, S—S, S=O, SO$_2$, Se, S—(CH$_2$)$_z$S— where z is a number of from 2 to 10; and, R$_1$ is hydrogen or an alkyl group containing from 1 to 5 carbons; and

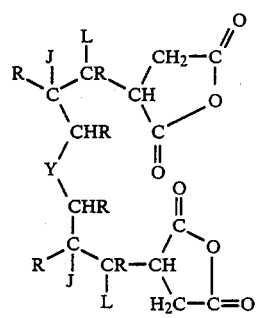

wherein: R is selected from the group consisting of hydrogen, hydrocarbyl and halo substituted hydrocarbyl containing from 1 to 10,000 carbons with the proviso that at least one R has at least four carbons; Y is selected from the group consisting of S, S—S, S=O, SO$_2$, Se, S—(CH$_2$)$_z$S— where z is a number of from 2 to 10; J is hydrogen, Cl or OH; and L is hydrogen with the proviso that (J=L) together can be a pi bond;

with (ii) from about one to about four moles of amine selected from the group consisting of amines represented by the formula

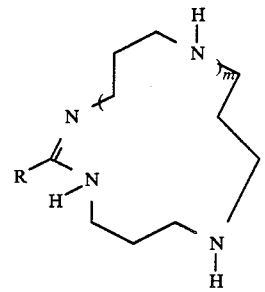

wherein: R is selected from the group consisting of hydrogen, hydrocarbyl and halo substituted hydrocarbyl containing from 4 to 10,000 carbons, and m is an integer of 0 to 10.

2. A composition according to claim 1 wherein said thio-bis-acylating agent is represented by the formula:

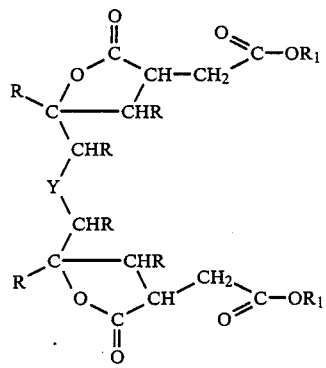

3. A composition according to claim 1 wherein said thio-bis-acylating agent is represented by the formula:

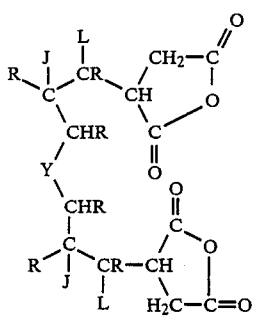

* * * * *